(12) United States Patent
Cashman

(10) Patent No.: US 8,609,708 B2
(45) Date of Patent: *Dec. 17, 2013

(54) SYNTHETIC COMPOUNDS AND DERIVATIVES AS MODULATORS OF SMOKING OR NICOTINE INGESTION AND LUNG CANCER

(75) Inventor: John R. Cashman, San Diego, CA (US)

(73) Assignee: Human BioMolecular Research Institute, San Diego, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 12/848,619

(22) Filed: Aug. 2, 2010

(65) Prior Publication Data

US 2010/0298345 A1    Nov. 25, 2010

Related U.S. Application Data

(62) Division of application No. 10/596,803, filed as application No. PCT/US2004/041924 on Dec. 10, 2004, now abandoned.

(60) Provisional application No. 60/531,696, filed on Dec. 23, 2003.

(51) Int. Cl.
*C07D 233/02* (2006.01)
*A61K 31/415* (2006.01)

(52) U.S. Cl.
USPC ........................ 514/396; 548/300.1

(58) Field of Classification Search
None
See application file for complete search history.

(56) References Cited

U.S. PATENT DOCUMENTS

2003/0100769 A1 * 5/2003 Imoto et al. ............... 548/311.1

FOREIGN PATENT DOCUMENTS

WO    WO 9803171 A2 * 1/1998

OTHER PUBLICATIONS

Liu et al The Journal of Nutrition 2003, vol. 133 (1): 173-179.*

* cited by examiner

*Primary Examiner* — Nyeemah A Grazier
(74) *Attorney, Agent, or Firm* — Edward D. Robinson; TechLaw LLP

(57) ABSTRACT

Disclosed are nicotine-related compounds that selectively inhibit cytochrome P-450 2A6 (CYP2A6), selectively inhibit cytochrome P-450 2A13 (CYP2A13), and/or selectively modulate a nicotinic acetylcholine receptor (nAChR). Also disclosed are pharmaceutical compositions comprising a compound of the invention, as well as methods of using the pharmaceutical compositions for treating or preventing a disease or disorder associated with nicotine-ingestion, or a disease or disorder amenable to treatment by selective modulation of nAChRs.

3 Claims, 21 Drawing Sheets

SYNTHETIC COMPOUNDS AND DERIVATIVES AS MODULATORS OF SMOKING OR NICOTINE INGESTION AND LUNG CANCER

CROSS-REFERENCES TO RELATED APPLICATIONS

The present application claims benefit to U.S. Provisional Application No. 60/531,696, filed Dec. 23, 2003, the entire disclosure of which is incorporated herein by reference.

FIELD OF THE INVENTION

This invention provides pharmaceutical compositions and compounds useful in methods of inhibiting cytochrome P450 2A6 and/or 2A13, reducing the use of tobacco products, reducing the exposure to nicotine and the harmful by-products associated with the use of tobacco products, and reducing the harmful health and addictive effects associated with the use of such products. The pharmaceutical compositions and compounds are also useful in treating central nervous system (CNS) diseases and disorders.

BACKGROUND OF THE INVENTION

Even though over 1.1 billion persons worldwide smoke tobacco, current therapies to reduce smoking (e.g., the nicotine patch) have a low success rate after one year. There is an urgent need to develop a specific medication that can be used in conjunction with counseling and self-help programs to decrease smoking and save lives. Despite clear evidence that smoking tobacco is the leading cause of preventable death, almost one in four American adults smoke tobacco.

The major pharmacologically active chemical in tobacco is (S)-nicotine. This (S)-nicotine is primarily responsible for the pharmacological and behavioral effects of smoking including the stimulant and addictive properties. Nicotine causes complex central nervous system, behavioral, cardiovascular, endocrine, neuromuscular and metabolic effects in humans. Nicotine is one of the most addictive substances known. After administration to humans, nicotine undergoes extensive metabolism which reduces its pharmacological activity. The majority of such nicotine is metabolized via a cytochrome P-450 2A6 (CYP2A6)-dependent pathway to form nicotine $\Delta^{1',5'}$-iminium ion. In the presence of aldehyde oxidase, nicotine $\Delta^{1',5'}$-iminium ion is converted to cotinine. While cotinine can be further metabolized, cotinine has a long half-life and is a useful marker for both nicotine exposure and is also a functional indicator of CYP2A6 activity. In humans, a similar metabolic pathway occurs in the lung and respiratory system and utilizes a related enzyme system, CYP2A13.

Tobacco users (e.g., smokers) adjust their tobacco use to maintain a certain blood and brain level of nicotine. Recently, it has been observed that individuals with a decreased ability to metabolize nicotine (so-called poor metabolizers because they possess inactive alleles that code for the prominent enzyme that metabolizes nicotine and terminates its activity) are protected from becoming dependent on nicotine and have a reduced lung cancer risk. However, most smokers are not poor metabolizers of nicotine.

Reducing nicotine intake concomittantly reduces the intake or exposure of a tobacco user or smoker to other tobacco and tobacco smoke contaminants and their metabolites. Many of the metabolites and constituents of tobacco and tobacco smoke are toxic, for instance, the highly carcinogenic tobacco-specific N-nitrosamines. Such tobacco-specific N-nitrosamines play an important role in tobacco-related human lung cancer, due to their strong ability to induce lung tumorigenesis. It has been shown that CYP2A6 is involved in the mutagenic activation of N-nitrosamines such as NNK, and that inhibition of CYP2A6 with a selective inhibitor, in turn, inhibits lung tumorigenesis in female A/J mice. In the lung, it is likely that cytochrome P-450 monoxygenases such as, e.g., CYP2A13 activate tobacco-related nitrosamines to mutagens and causes lung or other respiratory organ cancers.

The present invention meets these and other needs by providing novel compounds, pharmaceutical compositions, and methods of treatment which are useful in treating tobacco addiction, reducing tobacco consumption, and in inhibiting CYP2A6 and/or CYP2A13 activity generally and, particularly, with respect to the metabolism of nicotine by CYP2A6 and/or CYP2A13.

BRIEF SUMMARY OF THE INVENTION

In one aspect, the present invention provides novel compounds, pharmaceutical compositions, and methods of treatment directed toward inhibiting the activity of cytochrome P450 2A6 (CYP2A6) and/or 2A13 (CYP2A13) in a subject by administering compounds of Formula I. In preferred embodiments, the subject is a human. Particularly suitable compounds are those having Formula XI, XII, or XIII. Preferably, the compound is selective (based upon selectivity ratios) for CYP2A6 and/or 2A13 over at least one cytochrome P450 enzyme selected from 3A4, 2E1, 2B6, 2C9, 2C19, and 2D6. For example, in one specific embodiment, the compound selectively inhibits CYP2A6 over CYP3A4. In some further embodiments, the selectivity is at least 5-fold, 10-fold, or 20-fold over one or more of cytochrome P450 3A4, 2E1, 2B6, 2C9, 2C19, and 2D6. In still other variations, the compound is not a substrate of, or is not significantly metabolized by, CYP2A6. Typically, the biological half-time for the compound in human blood is at least 4 hours, at least 6 hours, at least 8 hours, or at least 12 hours. In certain variations, the compound of Formula I, XI, XII, or XIII is also capable of selectively modulating the activity of the nicotinic acetylcholine receptor (nAChR) (e.g., α and/or α/β nAChR).

In another aspect, the present invention provides methods of ameliorating the harmful effects (e.g., cancer) of tobacco use (e.g., smoking tobacco in cigarettes, cigars, or pipes; chewing tobacco) on health by administering a compound of Formula I or, more preferably, a compound of Formula XI, XII, or XIII, to a tobacco user. In one embodiment, the administered compound interferes with the metabolism of constituents of tobacco or tobacco smoke (e.g., nicotine, nitrosamines) so as to reduce the formation of carcinogenic metabolites.

In yet another aspect, the present invention provides a method for modulating tobacco consumption or tobacco use in a human by administering to the human a compound of Formula I, XI, XII, or XIII. The tobacco may be, for example, in the form of a chewing tobacco, a cigarette, cigar or pipe tobacco. In some embodiments, the modulating is according to the amount of the tobacco product consumed or the amount of nicotine, or another constituent of tobacco or tobacco smoke, taken into the body. In certain variations, a tobacco user is first phenotyped or genotyped with respect to cytochrome P450 and the compound is administered to users who are not poor metabolizers.

In still another aspect, the present invention provides a method of selectively modulating nicotinic acetylcholine receptors (nAChRs) in the CNS. The nAChR can be, for example, the α/β or α (e.g., 7) nAChR. In specific variations, the method is for the treatment of prevention of nicotine addiction, a neurodegenerative disease (e.g., Alzheimer's Disease or Parkinson's Disease), or a psychiatric disorder such as, e.g., anxiety, attention deficit disorder, or bipolar disorder. In yet other embodiments, selective modulation of nAChRs is used to enhance cognition or to provide a neuroprotective effect in a subject.

Definitions

Unless defined otherwise, all technical and scientific terms used herein have the same meaning as commonly understood by one of ordinary skill in the art to which this invention belongs. Although any methods and material similar similar to those described herein can be used in the practice or testing of the present invention, only exemplary methods and materials are described. For purposes of the present invention, the following terms are defined below.

The terms "a," "an," and "the" include plural referents unless the context clearly dictates otherwise.

The term "hydrido" refers to a single hydrogen.

The term "alkyl" refers to saturated aliphatic groups including straight chain, branched chain, and cyclic groups, all of which may be optionally substituted. Suitable alkyl groups include methyl, ethyl and the like, and may be optionally substituted.

The term "alkenyl" refers to unsaturated groups which contain at least one carbon-carbon double bond and includes straight chain, branched chain, and cyclic groups, all of which may be optionally substituted.

The term "alkynyl" refers to unsaturated groups which contain at least one carbon-carbon triple bond and includes straight chain, branched chain, and cyclic groups, all of which may be optionally substituted. Suitable alkynyl groups include ethynyl, propynyl, butynyl and the like which may be optionally substituted.

The term "alkoxy" refers to the ether —OR where R is alkyl, alkenyl, alkynyl, aryl, aralkyl.

The term "aryloxy" refers to the ether —OR where R is aryl or heteroaryl.

The term "alkenyloxy" refers to ether —OR where R is alkenyl.

The term "alkylthio" refers to —SR where R is alkyl, alkenyl, alkynyl, aryl, aralkyl.

The term "alkylthioalkyl" refers to an alkylthio group attached to an alkyl radical of about one to twenty carbon atoms through a divalent sulfur atom.

The term "alkylsulfinyl" refers to —S(O)R where R is alkyl, alkenyl, alkynyl, aryl, aralkyl.

The term "sulfonyl" refers to a —$SO_2$—R group where R is alkyl, alkenyl, alkynyl, aryl, aralkyl.

The term "aminosulfonyl", "sulfamyl", "sulfonamidyl" refer to —$SO_2$NRR' where R and R' are independently selected from alkyl, alkenyl, alkynyl, aryl, aralkyl.

The term "hydroxyalkyl" refers to linear or branched alkyl radicals having one to about twenty carbon atoms any one of which may be substituted with a hydroxyl group.

The term "cyanoalkyl" refers to linear or branched alkyl radicals having one to about twenty carbon atoms any one of which could be substituted with one or more cyano groups.

The term "alkoxyalkyl" refers to alkyl groups having one or more alkoxy radicals attached to the alkyl group. The alkoxy radical may be further substituted with one or more halo atoms. Preferred haloalkoxy groups may contain one to twenty carbons.

The term "oximinoalkoxy" refers to alkoxy radicals having one to about twenty carbon atoms, any one of which may be substituted with an oximino radical.

The term "aryl" refers to aromatic groups which have at least one ring having conjugated "pi" electron system and includes carbocyclic aryl, biaryl, both of which may be optionally substituted.

The term "carbocyclic aryl" refers to groups wherein the ring atoms on the aromatic ring are carbon atoms. Carbocyclic groups include phenyl and naphthyl groups which may be optionally substituted with 1 to 5 substituents such as alkyl, alkoxy, amino, amido, cyano, carboxylate ester, hydroxyl, halogen, acyl, nitro.

The term "aralkyl" refers to an alkyl group substituted with an aryl group. Suitable aralkyl groups include benzyl, and the like, and may be optionally substituted.

The term "aroyl" refers to —C(O)R where R is aryl group.

The term "alkoxycarbonyl" refers to —C(O)OR wherein R is alkyl, akenyl, alkynyl, aryl, aralkyl.

The term "acyl" refers to the alkanoyl group —C(O)R where R is, alkenyl, alkynyl, aryl, aralkyl.

The term "acyloxy" refers to the alkanoyl group —OC(O)R where R is, alkenyl, alkynyl, aryl, aralkyl.

The term "aminoalkyl" refers to alkyl which is substituted with amino groups.

The term "arylamino" refers to amino groups substituted with one or more aryl radicals.

The term "aminocarbonyl" refers to —C(O)$NRR_1$ wherein R and $R_1$ are independently selected from hydrogen, alkyl, akenyl, alkynyl, aryl, aralkyl.

The azidoalkyl refers to alkyl R which is substituted with azido —$N_3$

The term "amino" refers to —$NRR_1$ where R and $R_1$ are independently hydrogen, lower alkyl or are joined together to give a 5 or 6-membered ring such as pyrrolidine or piperidine rings which are optionally substituted.

The term "alkylamino" includes amino groups substituted with one or more alkyl groups.

The term "dialkylamino" refers to —$NRR_1$R and $R_1$ are independently lower alkyl groups or together form the rest of ring such as morpholino. Suitable dialkylamino groups include dimethylamino, diethylamino and morpholino.

The term "morpholinoalkyl" refers to alkyl R substituted with morpholine group.

The term "isocyanoalkyl" refers to alkyl R that is substituted with isocyano group —NCO.

The term "isothiocyanoalkyl" refers to alkyl R that is substituted with isothiocyano group —NCS.

The term "isocyanoalkenyl" refers to alkenyl R that is substituted with isocyano group —NCO.

The term "isothiocyanoalkenyl" refers to alkenyl R that is substituted with isothiocyano group —NCS.

The term "isocyanoalkynyl" refers to alkynyl R that is substituted with isocyano group —NCO.

The term "isothiocyanoalkynyl" refers to alkynyl R that is substituted with isothiocyano group —NCS.

The term "alkanoylamino" refers to —NRC(O)$OR_1$ where R and $R_1$ are independently hydrogen, lower alkyl, akenyl, alkynyl, aryl, aralkyl.

The term "formylalkyl" refers to alkyl R substituted with —CHO.

The term "optionally substituted" or "substituted" refers to groups substituted by one to five substituents, independently selected from lower alkyl (acyclic or cyclic), aryl (carboaryl or heteroaryl) alkenyl, alkynyl, alkoxy, halo, haloalkyl (including trihaloalkyl, such as trifluoromeyl), amino, mercapto, alkylthio, alkylsulfinyl, alkylsulfonyl, nitro, alkanoyl, alkanoyloxy, alkanoyloxyalkanoyl, alkoxycarboxy, (—COOR, where R is lower alkyl), aminocarbonyl (—CONRR$_1$, where R and R$_1$ are independently lower alkyl), formyl, carboxyl, hydroxyl, cyano, azido, keto, and cyclic ketals thereof, alkanoylamido, heteroaryloxy, and heterocarbocyclicoxy.

The term "lower" refers herein in connection with organic radicals or compounds defines such as one up to and including ten, preferably up to and including six, and more preferably one to four carbon atoms. Such groups may be straight chain, branched chain, or cyclic.

The term "heterocyclic" refers to carbon containing radicals having three, four, five, six, or seven membered rings and one, two, three, or four O, N, P, or S heteroatoms, e.g., thiazolidine, tetrahydrofuran, 1,4-dioxane, 1,3,5-trioxane, pyrrolidine, pyridyl, piperidine, quinuclidine, dithiane, tetrahydropyran, and morpholine or fused analogs containing any of the above.

The term "heteroaryl" refers to carbon containing 5-14 membered cyclic unsaturated radicals containing one, two, three, or four O, N, P, or S atoms and having 6, 10 or 14 π electrons delocalized in one or more than one rings, e.g., pyridine, oxazole, indole, purine, pyrimidine, imidazole, benzimidazole, indazole, 2H-1,2-4-triazole, 1,2,3-triazole, 2H-1, 2,3,4-tetrazole, 1H-1,2,3,4-triazolebenztriazole, 1,2,3-triazolo[4,5-b]pyridine, thiazole, isoxazole, pyrazole, quinoline, cytosine, thymine, uracil, adenine, guanine, pyrazine, picoline, picolinic acid, furoic acid, furfural, furyl alcohol, carbazole, isoquinoline, pyrrole, thiophene, furan, phenoxazine, and phenothiazine, each of which may be optionally substituted.

The term "pharmaceutically acceptable esters, amides, or salts" refers to esters, amides, or salts of FIG. 1 derived from the combination of a compound of this invention and an organic or inorganic acid.

The term "nicotine-related agent" refers to nicotine-related alkaloids, nicotine metabolites, nicotine analogues, and nicotine derivatives, such as further described herein. In particular embodiments of the present invention, a nicotine-related agent having any one of the formulas as set forth herein is not nicotine or cotinine.

The term "inhibit" means to reduce by a measurable amount, or to prevent entirely.

"Treating," "treatment," or "therapy" of a disease or disorder means slowing, stopping, or reversing progression of the disease or disorder, as evidenced by a reduction or elimination of either clinical or diagnostic symptoms, using the compositions and methods of the present invention as described herein.

"Preventing," "prophylaxis," or "prevention" of a disease or disorder means prevention of the occurrence or onset of a disease or disorder or some or all of its symptoms.

The term "subject" as used herein means any mammalian patient to which the compositions of the present invention may be administered according to the methods described herein. Subjects specifically intended for treatment or prophylaxis using the methods of the present invention include humans.

The term "therapeutically effective regime" means that a pharmaceutical composition or combination thereof is administered in sufficient amount and frequency and by an appropriate route to at least detectably prevent, delay, inhibit, or reverse development of at least one symptom or biochemical marker of a nicotine-related disorder. In certain embodiments, the "therapeutically effective regime" predisposes a subject to ingest lower amounts of nicotine and/or inhibits mutagenic activation of N-nitrosamines to in turn decrease the risk of developing cancer.

The term "therapeutically effective amount" refers to an amount of an nicotine-related agent, or a combination of a nicotine-related agent with other agent(s), is present to achieve a desired result, e.g., preventing, delaying, inhibiting, or reversing a symptom or biochemical marker of a nicotine-related disorder when administered in an appropriate regime.

DETAILED DESCRIPTION OF THE INVENTION

Figure 1:
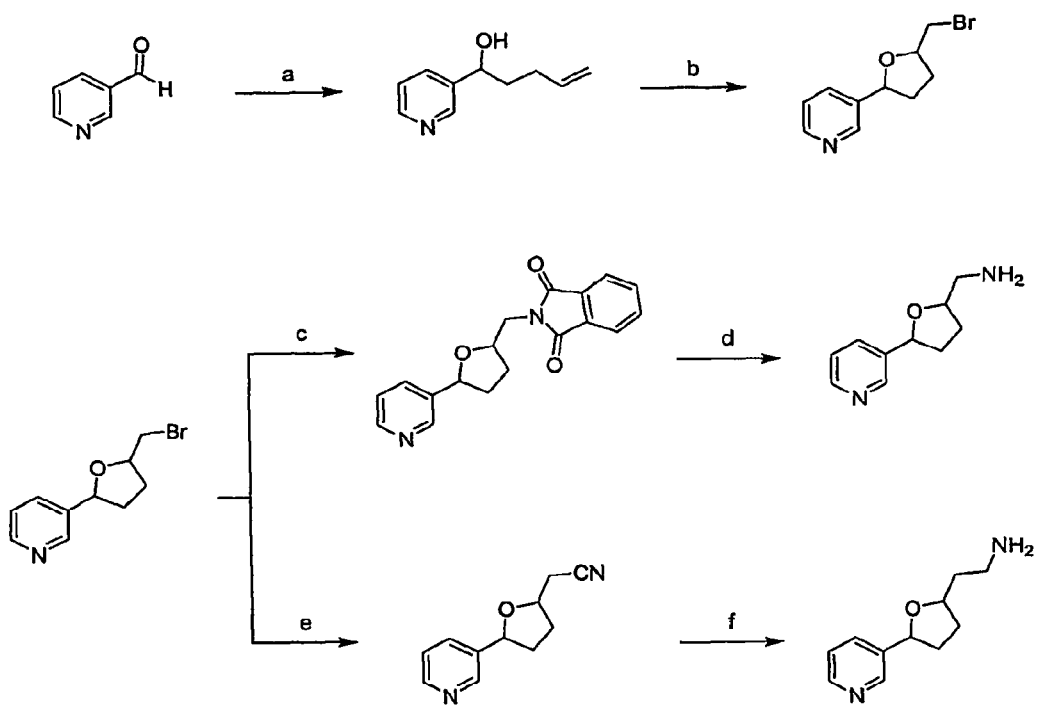
FIG. 1 depicts synthesis of substituted tetrahydrofuran analogs of nicotine as described in Example 1. (a) 1-1-butenylmagnesium bromide; (b) N-bromosuccinimide, CH$_2$Cl$_2$; (c) NaI, potassium phthilimide, DMSO; (d) NH$_2$NH$_2$, MeOH; (e) NaI, KCN, DMSO; (f) Raney Ni, H$_2$.

This invention relates to methods of reducing the risk of cancer as well as treating nicotine addiction and other CNS diseases by inhibiting the metabolism of tobacco-specific N-nitrosamines and nicotine and/or of modulating the binding and or reuptake of neurotransmitters. More specifically, this invention relates to the prophylaxis of cancer (e.g., lung cancer) and smoking and tobacco addiction through the use of small molecule nicotine-related agents and synthetic derivatives thereof. These compounds are also useful in the treatment of other CNS diseases, including, e.g., neurodegenerative diseases and psychiatric disorders (e.g., drug abuse, anxiety, attention deficit disorder (ADD), and bipolar disorder).

In one aspect, the present invention provides selective inhibitors of cytochrome P-450 2A6 (CYP2A6) and/or 2A13 (CYP2A13). In preferred embodiments, an agent of the present invention is a selective dual inhibitor of both CYP2A6 and CYP2A13.

CYP2A6 inhibitors are useful for, e.g., for reducing nicotine ingestion (e.g., smoking) and addiction. Inhibition of CYP2A6 using a compound as described herein reduces nicotine metabolism in a subject in which nicotine is present, thereby increasing blood levels of nicotine and predisposing the subject to ingest lower amounts of nicotine. CYP2A6 inhibitors as described herein are also useful for decreasing metabolism of other products, including, for example, promutagens that are activated by CYP2A6 to mutagens. For example, inhibition of CYP2A6 is useful for preventing mutagenic activation of the carcinogenic, tobacco-specific promutagen 4-(methylnitrosamino)-1-(3-pyridyl)-1-butanone (NNK), thereby decreasing the risk of developing cancer.

CYP2A13, another cytochrome P-450 monooxygenase, shows predominant expression in the respiratory tract (see, e.g., Su et al., *Cancer Res.* 60:5074-5079, 2000). CYP2A13 has been shown to present a higher activity in the metabolism of several nitrosamines than CYP2A6 when expressed in a heterologous system (see Su et al., supra). Accordingly, a selective inhibitor of CYP2A13, particularly dual inhibitors of CYP2A6 and CYP2A13, have enhanced therapeutic and prophylactic effects against disorders associated with, e.g., nicotine and tobacco ingestion.

The effects of nicotine on mood and tobacco seeking behavior are mediated by acetylcholinergic receptors in the central nervous system which respond selectively to nicotine. Accordingly, in other preferred embodiments, an agent of the present invention is a dual CYP2A6 and/or CYP2A13 inhibitor and nicotinic acetylcholine receptor (nAChR) binding agent. In certain variations, the compound selectively binds the α/β. Agents that selectively bind the nAChR modulate (e.g., blunt) nicotinic central nervous system (CNS) activity and may also be used for treatment of nicotine addiction to reduce the use and exposure to the harmful ingredients in tobacco products and their smoke.

In yet other variations of the present invention, selective modulation of α7 nAChRs are useful, for example, for various CNS associated applications. For example, selective modulation of nAChRs is useful for enhancing cognition or for inducing a neuroprotective effect in a subject in need thereof. In addition, modulation of nAChRs are useful for treatment or prophylaxis of various CNS-associated disorders and diseases, including, for example, neurodegenerative diseases (e.g., Alzheimer's Disease, Parkinson's Disease, and the like) as well as various psychiatric disorders (e.g., anxiety, attention deficit disorder (ADD), bipolar disorder, drug abuse, and the like). In particular embodiments, the nAChR is the α7 nAChR (e.g., for treatment of neurodegenerative disease such as Alzheimer's Disease or Parkinson's Disease). Depending on the application, the compound that selectively bind nAChRs to modulate the activity thereof is an agonist or an antagonist of the nAChR.

CYP2A6/CYP2A13 Inhibitors and nAChR Binding Agents

In one embodiment, the general chemical structure of the invention is represented by Formula IA:

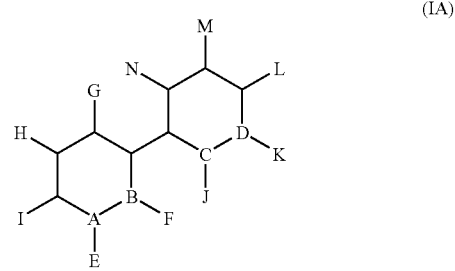

(IA)

and pharmaceutically acceptable salts, esters, amides, and other forms or prodrugs, thereof, wherein A, B, C, D, E, F, G, H, I, J, K, L, M, and N are further defined. In the foregoing, the stereochemistry will not be designated and isomers at the various centers of chirality will be included. The general structure is shown in Formula IA wherein A, B, C and D constitute part of a 5- or 6-member ring system from unsaturated, partially saturated or unsaturated heterocyclo and carbocyclic rings wherein A, B, C, D are each independently selected from the group consisting of carbon, nitrogen, oxygen and sulfur, or is absent; and wherein A, B, C, and D is optionally substituted with hydrido, acyl, halo, lower acyl, lower haloakyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl, aryl, lower axalkylthio, lower alkylsulfinyl, lower alkylsulfonyl, aminosulfonyl, lower N-arylaminosulfonyl, lower arylsulfonyl, or lower N-alkyl-N-arylaminosulfonyl; wherein aryl is selected from phenyl, biphenyl, naphthyl, and 5- or 6-membered heteroaryl and is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy; and wherein the acyl group is optionally substituted with a substituent selected from hydrido, alkyl, halo, and alkoxy.

In one embodiment of the compound of Formula IA, A is optionally substituted with hydrido, acyl, halo, lower acyl, lower haloakyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkylsulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein the acyl group is optionally substituted with a substituent selected from hydrido, alkyl, halo, and alkoxy.

In another embodiment, the substituents A together with B and C together with D are each independently part of a ring system selected from the group consisting of pyranyl, furyl, tetrahydrofuryl, tetrahydrothienyl, thienyl, oxazolyl, pyrolyl, thiazolyl, imidazolyl, isthiazolyl, isoxazoly, pyrazolyl, cyclopentyl, phenyl, and pyridyl.

E, F, G, H, I, J, K, L, M, and N are each independently selected from the group consisting of aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, aminoalkyl, imidoalkyl, alkoxycarbonyl, alkoxycarbonylalkyl, alkylamino, alkylaminoalkyl, dialkylamino, dialkylaminnalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, naphthyl, and 5- or 6-membered heteroaryl, wherein aryl is optionally substituted. In addition, two adjacent groups are optionally joined together to form a fused carbocyclic or heterocyclic ring system. For example, E and F may be part of a ring that is fused to a 5- or 6-membered ring system in Formula IA.

In one embodiment, each of the 5- or 6-membered ring system having the substituents A and B or C and D forms a heterocyclic ring system selected from the group comprising pyrrolidine, piperidine, piperazine, heptamethyleneimine, hexamethyleneimine, homopiperazine, perhydroindole, azetidine, 4-piperidinopiperidine, 1-azacycloheptane, imidazoyl, perhydroisoquioline, decahydroquinoline, 1-phenylpiperazine. 4-phenylpiperidine, 1-(fluorophenyl)piperazine, 1,3,5-hexa-hydrotriazine, morpholine, phenylmorpholine, thiomorpholine, tetrahydrothiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, —OR$_4$, —R$_5$, —OC(O)R$_6$, OC(O)NR$_7$R$_8$, —C(O)R$_9$, —CN, —SR$_{12}$, —S(O)R$_{11}$, —S(O)$_2$R$_{14}$, —C(O)OR$_{15}$, —S(O)$_2$NR$_{16}$R$_{17}$; —R$_{18}$NR$_{19}$R$_{20}$ wherein R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, and R$_{20}$ are the same or different and are branched or unbranched alkyl groups from one to eight carbon atoms or hydrogen radicals.

In another embodiment, the compounds of the present invention have the structure as shown in Formula XI:

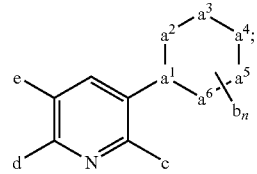

(XI)

wherein $a^1$, $a^2$, $a^3$, $a^4$, $a^5$ and $a^6$ are each independently selected from the group consisting of carbon, nitrogen, oxygen and sulfur, or is absent. In one preferred embodiment, $a^1$, $a^2$, $a^3$, $a^4$, $a^5$ and $a^6$ are part of a 5- or 6-membered, unsaturated or partially unsaturated ring system. In another preferred embodiment, $a^1$ and $a^2$ are carbon and $a^3$, $a^4$, $a^5$ and $a^6$ are absent.

$b_n$ is a substituent selected from the group consisting of hydrogen, methyl, lower alkyl, aminomethyl, N-methylaminomethyl, benzyl, oximino, amino, nitro, ethyl, formyl, bromomethyl, heteroarylaminomethyl, heteroaryl, 3-(3-methylthienyl)pyridyl, 2-(3-methyl)thienyl, 3-thienyl, CH$_3$(C=O)—, N,N-dimethylaminomethyl, aminopropyl, hydroxymethyl, pyridyl and oxo; and n is an integer from 0 to 10. Alternatively, any two substituents "b" adjacent to each other on the 5- or 6-membered ring may be taken together with the atoms to which they are attached to form a 5- or 6-membered aryl or heteroaryl ring system.

c is hydrogen or amino.

d is selected from the group consisting of hydrogen, fluoro, methoxy, amino and chloro.

e is a substituent selected from the group consisting of hydrogen, methyl, 2-(3-methylthienyl), CH$_3$O(C=O)—, bromo, ethynyl, 3-thienyl and hydroxymethyl.

In one embodiment of Formula (XI), $a^1$, $a^2$, $a^3$, $a^4$, $a^5$ and $a^6$ form a 5- or 6-member ring system selected from the group consisting of

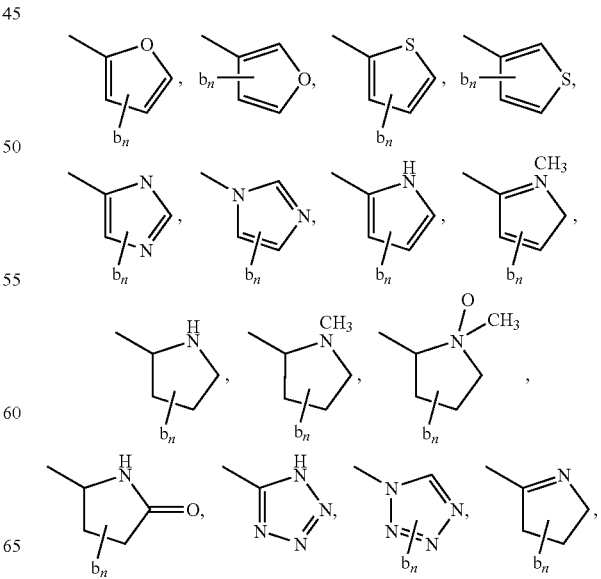

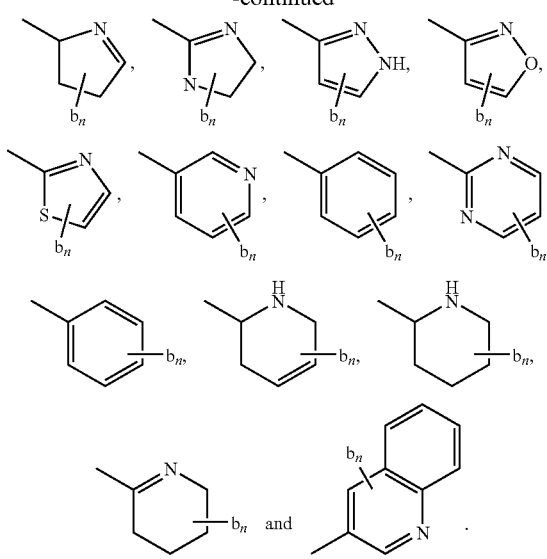

In a preferred embodiment of Formula XI, a compound of the invention has the structure according to Formula XII:

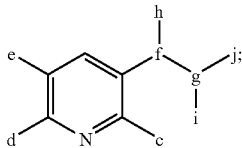

(XII)

wherein f and g are each carbon or nitrogen atom; and wherein f and g are connected to each other by a single, double or triple bond.

h and i are each independently hydrogen, lower alkyl group, or is absent; and wherein h and i together with the atoms to which they attached may optionally be combined to form a 3- to 5-membered ring.

j is selected from the group consisting of aminomethyl, N-methylaminomethyl, amino, 2-(3-methyl)thienyl, 3-thienyl, N,N-dimethylaminomethyl, heteroaryl and 3-(3-methylthienyl)pyridyl.

c is hydrogen or amino.

d is selected from the group consisting of hydrogen, fluoro, methoxy, amino and chloro.

e is a substituent selected from the group consisting of hydrogen, methyl, 2-(3-methylthienyl), CH₃O(O)—, bromo, ethynyl, 3-thienyl and hydroxymethyl.

In one embodiment, in Formula XII, the fragment

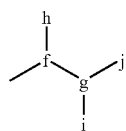

is selected from the group consisting of:

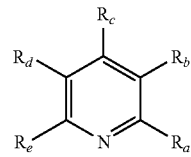

In yet other variations, the present invention provides compounds of the following Formula XIII:

(XIII)

in which Ra, Rc, and Re are independently selected from the group consisting of hydrogen, (C1-C6)alkyl, (C1-C6) alkenyl, (C1-C6)alkynyl, heteroalkyl, halo (e.g., fluoro, chlor, bromo, iodo), (C1-C6)alkoxy, amino, (c1-C6)alkylamino, hydroxy, cyano, and nitro; and $R_b$ is a 5- or 6-member unsaturated, partially unsaturated or saturated heterocyclic and carbocyclic ring system. The $R_b$ ring system is optionally substituted with hydrido, acyl, halo, lower acyl, lower haloakyl, oxo, cyano, nitro, carboxyl, amino, lower alkoxy, aminocarbonyl, lower alkoxycarbonyl, alkylamino, acylamino, lower carboxyalkyl, lower cyanoalkyl, lower hydroxyalkyl, alkylthio, alkyl sulfinyl, aryl, lower aralkylthio, lower alkylsulfinyl, lower alkylsulfonyl, aminosulfonyl, lower N-arylaminosulfonyl, lower arylsulfonyl, or lower N-alkyl-N-arylaminosulfonyl; in which the above aryl member is selected from phenyl, biphenyl, naphthyl, and 5- or 6-membered heteroaryl; and in which the above aryl member is optionally substituted with one, two, or three substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy; and wherein further the acyl group is optionally substituted with a substituent selected from hydrido, alkyl, halo, and alkoxy. The $R_b$ radical preferably has one or two ring hydrogens substituted with substituents selected from Cl, Br, I, —OR₄, —R₅, —OC(O)R₆, OC(O)NR₇R₈, —C(O)R₉, —CN, —NR₁₀R₁₁, —SR₁₂, —S(O)R₁₁, —S(O)₂R₁₄, —C(O)OR₁₅, —S(O)₂NR₁₆R₁₇; and —R₁₈NR₁₉R₂₀, wherein R₄, R₅, R₆, R₇, R₈, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals. $R_d$ is independently selected from the members of the $R_a$ and $R_b$ Markush groups as set forth above.

In one embodiment, the compound is a compound of Formula XIII in which $R_a$, $R_c$, $R_d$, and $R_e$ each hydrogen. In yet a further embodiment, the compound is a compound of Formula XIII in which $R_a$, $R_c$, $R_d$, and $R_e$ are each hydrogen and $R_b$ is a 5-membered heterocyclic or carbocyclic ring system. In another embodiment of the above, $R_a$, $R_c$, $R_d$, and $R_e$ are each hydrogen and $R_b$ is a substituted or unsubstituted 5-membered ring system having one or two heteroatoms selected from O, N, and S in the ring. In some further embodiments the ring system heteroatom is selected from O or S. In further embodiments of each of the above, the compound in not nicotine or cotinine. In yet still further embodiments, the compound is a compound of Formula XIII in which $R_a$, $R_c$, $R_d$, and $R_e$ are each hydrogen and $R_b$ is a 6-membered heterocyclic or carbocyclic ring system. In another embodiment of the above, $R_a$, $R_c$, $R_d$, and $R_e$ are each hydrogen and $R_b$ is a substituted or unsubstituted 6-membered ring system having one heteroatom selected from O, N, and S. In another embodiment of the above, $R_a$, $R_c$, $R_d$, and $R_e$ are each hydrogen and $R_b$ is a substituted or unsubstituted 6-membered ring system having two heteroatoms selected from O, N, and S.

In another embodiment of the above, the compound of Formula XIII is a compound in which $R_d$ is independently selected from the Markush group for $R_a$. In still a further embodiment, the $R_d$ and $R_b$ groups are the same. In yet still a further embodiment, the $R_d$ and $R_b$ groups are the same and $R_a$, $R_c$, and $R_e$ are each hydrogen. In yet still a further embodiment, the $R_d$ and $R_b$ groups are the same and $R_a$, $R_c$, and $R_e$ are independently selected from hydrogen, halogen, nitro, cyano, or (C1-C6) alkyl, or (C1-C6) alkoxy.

In preferred embodiments of the compounds of Formula XIII, the $R_b$ radical is an unsubstituted or substituted radical selected from, but not limited to pyrrolyl, N-methylpyrrolyl, pyranyl, furyl, tetrahydrofuryl, tetrahydrothienyl, thienyl, oxazolyl, pyrolyl, thiazolyl, imidazolyl, isothiazolyl, isoxazolyl, pyrazolyl, cyclopropyl, cyclobutyl, cyclopentyl, phenyl, pyridyl and the like. In these embodiments, the $R_b$ radical optionally may have one, two or three ring hydrogens substituted with substituents selected from Cl, Br, I, —$OR_4$, —$R_5$, —$OC(O)R_6$, $OC(O)NR_7R_8$, —$C(O)R_9$, —CN, —$NR_{10}R_{11}$, —$SR_{12}$, —$S(O)R_{11}$, —$S(O)_2R_{14}$, —$C(O)OR_{15}$, —$S(O)_2NR_{16}R_{17}$; and —$R_{18}NR_{19}R_{20}$, wherein $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals. In further still of these embodiments, $R_a$, $R_c$, $R_d$, and $R_e$ are independently selected from the group consisting of hydrogen, halogen, nitro, amino cyano, (C1-C6) alkyl, and (C1-C6) alkoxy.

In other preferred embodiments of the compounds of Formula XIII, $R_a$, $R_c$, $R_d$, and $R_e$ are independently selected from the group consisting of hydrogen, halogen, amino, mono- or -di-(C1-C6)alkylamino, nitro, cyano, (C1-C6) alkyl, and (C1-C6) alkoxy. In still other preferred embodiments, $R_a$, $R_c$, $R_d$, and $R_e$ are independently selected from hydrogen or halogen (e.g., chloro, fluoro, bromo). In yet other embodiments, $R_a$ is hydrogen. In still other embodiments, $R_c$ is hydrogen. In still other embodiments, $R_e$ is hydrogen. In still other embodiments, $R_a$, $R_c$, and $R_e$ are each hydrogen.

In other embodiments, $R_d$ is hydrogen or amino, $R_e$ is selected from the group consisting of hydrogen, fluoro, methoxy, amino, and chloro; $R_c$ is hydrogen, and $R_d$ is selected from the group consisting of hydrogen, methyl, 2-(3-methylthienyl), $CH_3O(C=O)$—, bromo, ethynyl, 3-thienyl and hydroxymethyl.

Other Embodiments of the CYP2A6/CYP2A13 Inhibitors and nAChR Binding Agents

In one embodiment of the invention, the compounds of the invention have Formula I:

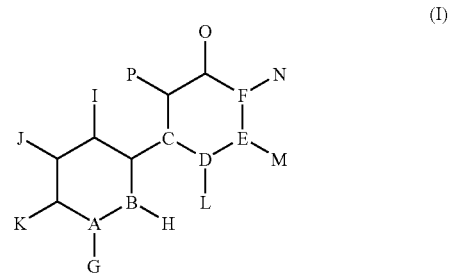

(I)

wherein A, B, C, D, E and F constitute part of a 3-, 4-, 5- or 6-member ring system of unsaturated, partially unsaturated or saturated heterocyclic and carbocyclic rings wherein the A, B, C, D, E and F ring system is optionally substituted with hydrido, acyl, halo, lower acyl, lower haloakyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkyl sulfinyl and aryl, lower aralkylthio, lower alkylsulftnyl, lower alkylsulfonyl, aminosulfonyl, lower N-arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein the acyl group is optionally substituted with a substituent selected from hydrido, alkyl, halo, and alkoxy.

Representative heterocycles which make up the central ring systems of Formula I including the A, B, C, D, E and F atoms include, but are not limited to pyrrolidine, piperidine, piperazine, heptamethyleneimine, hexamethyleneimine, homopiperazine, perhydroindole, azetidine, 4-piperidinopiperidine, 1-azacycloheptane, imidazoyl, perhydroisoquioline, decahydroquinoline, 1-phenylpiperazine. 4-phenylpiperidine, 1-(fluorophenyl)piperazine, 1,3,5-hexa-hydrotriazine, morpholine, phenylmorpholine, thiomorpholine, tetrahydrothiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, —$OR_4$, —$R_5$, —$OC(O)R_6$, $OC(O)NR_7R_8$, —$C(O)R_9$, —CN, —$NR_{10}R_{11}$, —$SR_{12}$, —$S(O)R_{11}$, —$S(O)_2R_{14}$, —$C(O)OR_{15}$, —$S(O)_2NR_{16}R_{17}$; —$R_{18}NR_{19}R_{20}$ wherein $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals.

A preferred class of compounds consists of compounds of Formula I wherein the A B, C, D, E and F ring system is a radical selected from pyranyl, furyl, tetrahydrofuryl, tetrahydrothienyl, thienyl, oxazolyl, pyrolyl, thiazolyl, imidazolyl, isothiazolyl, isoxazolyl, pyrazolyl, cyclopropyl, cyclobutyl, cyclopentyl, phenyl, and pyridyl.

G, H, I, J, K, L M, N, O and P are selected from aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups may be joined together to form a part of a fused carbocyclic or heterocyclic ring system. For example, L and M may be part of a second ring that is fused to the C, D, E, F ring.

In another embodiment, the compound having formula I can be represented by formula II:

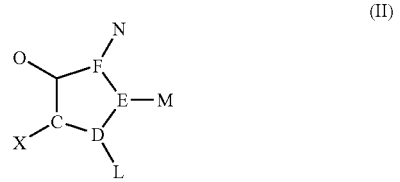

(II)

wherein C, D, E and F constitute a 5-membered ring containing carbon, oxygen, sulfur, nitrogen, or phosphorus; X is the A, B ring system defined as in formula I, and L, M, N, and O are as defined in formula I.

In a preferred embodiment, in the compound having Formula II, C is a carbon, D is an oxygen, E is a carbon and L, M, N, O and X are selected from the group consisting of aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl, and formylalkyl.

In another embodiment, the compound having Formula I is selected from the group consisting of (5-pyridin-3-yl-tetrahydro-furan-2-yl)-methylamine, 3-(5-bromomethyl-tetrahydro-furan-2-yl)-pyridine, 3-(5-ethyl-tetrahydro-furan-2-yl)-pyridine, and (5-pyridin-3-yl-tetrahydro-furan-2-yl)-methanol.

In another embodiment, in the compound having Formula II, C is a carbon, D is a sulfur, E is a carbon and L, M, N, O and X are selected from the group consisting of aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl and formylalkyl.

In another embodiment, in the compound having Formula II, C is a carbon, D is a nitrogen, E is a carbon and L, M, N, O and X are selected from the group consisting of aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl and formylalkyl.

In another embodiment, the compound having Formula I can be represented by Formula III:

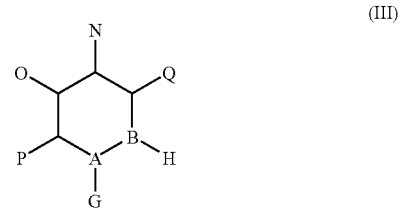

(III)

wherein A, B, G, H, N, O and P are defined as for Formula I.

In another preferred embodiment, in the compound having Formula III, A is a nitrogen, B is a carbon and Q is a 5- or 6-member unsaturated, partially unsaturated or saturated heterocyclic and carbocyclic ring wherein the ring system is optionally substituted with hydrido, acyl, halo, lower acyl, lower haloakyl, oxo, cyano, nitro, carboxyl, amino, lower alkoxy, aminocarbonyl, lower alkoxycarbonyl, alkylamino, arylamino, lower carboxyalkyl, lower cyanoalkyl, lower hydroxyalkyl, alkylthio, alkyl sulfinyl and aryl, lower aralkylthio, lower alkylsulfinyl, lower alkylsulfonyl, aminosulfonyl, lower N—arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein the acyl group is optionally substituted with a substituent selected from hydrido, alkyl, halo, and alkoxy.

A preferred class of compounds consists of compounds of Formula III wherein the Q ring is a substituted or unsubstituted radical selected from, but not limited to pyrrolyl, N-methylpyrrolyl, pyranyl, furyl, tetrahydrofuryl, tetrahydrothienyl, thienyl, oxazolyl, pyrolyl, thiazolyl, imidazolyl, isothiazolyl, isoxazolyl, pyrazolyl, cyclopropyl, cyclobutyl, cyclopentyl, phenyl, pyridyl and the like, optionally having one or two ring hydrogens substituted with substituents selected from Cl, Br, I, —OR$_4$, —R$_5$, —OC(O)R$_6$, OC(O)NR$_7$R$_8$, —C(O)R$_9$, —CN, —NR$_{10}$R$_{11}$, —SR$_{12}$, —S(O)R$_{11}$, —S(O)$_2$R$_{14}$, —C(O)OR$_{15}$, —S(O)$_2$NR$_{16}$R$_{17}$; —R$_{18}$NR$_{19}$R$_{20}$ wherein R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, and R$_{20}$ are the same or different and are branched or unbranched alkyl groups from one to eight carbon atoms or hydrogen radicals.

When the above radicals are incorporated into the parent molecule, the present invention includes all possible stereochemical arrangements of the substituents. In addition, the optional agent includes racemic or stereochemically pure compounds.

In another embodiment, the compound having Formula I is selected from the group consisting of 3-(4-methyl-thiophen-3-yl)-pyridine, 3-(1H-imidazol-4-yl)-pyridine, 3-pyrazol-1-yl-pyridine, 3-thiophen-2-yl-pyridine, [3,3']bipyridinyl and 3-thiazol-2-yl-pyridine.

In another embodiment, the compound having Formula I can be represented by Formula IV:

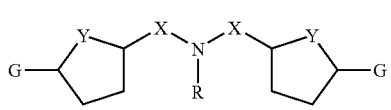

(IV)

wherein G is the A, B ring system defined as in Formula I, X is a saturated carbon chain from $C_2$-$C_8$ and Y is a carbon, oxygen, sulfur, nitrogen or phosphorus atom. R is alkyl, akenyl, alkynyl, optionally substituted aryl and aralkyl.

In another preferred embodiment, in the compound having Formula IV, X is ethylene, Y is oxygen, R is hydrogen and G is 3-pyridyl.

In another embodiment, the compound having Formula IV is bis-[2-(5-pyridin-3-yl-tetrahydro-furan-2-yl)-ethyl]-amine.

In another embodiment, in the compound having Formula IV, X is ethylene, Y is sulfur, R is hydrogen and G is 3-pyridyl.

In another embodiment, in the compound having Formula IV, X is ethylene, Y is nitrogen, R is hydrogen and G is 3-pyridyl.

In another embodiment, the compound having Formula I can be represented by Formula V:

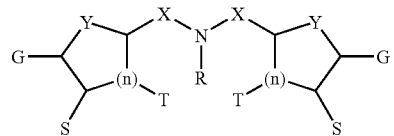

(V)

wherein G is the A, B ring system defined as in Formula I, X is a saturated carbon chain from $C_2$-$C_8$ and R is alkyl, akenyl, alkynyl, optionally substituted aryl and aralkyl. Representative heterocycles which make up the Y ring system of Formula V including the S and T substituents include, but are not limited to pyrrolidine, piperidine, piperazine, heptamethyleneimine, hexamethyleneimine, homopiperazine, perhydroindole, azetidine, 4-piperidinopiperidine, 1-azacycloheptane, imidazoyl, perhydroisoquioline, decahydroquinoline, 1-phenylpiperazine. 4-phenylpiperidine, 1-(fluorophenyl)piperazine, 1,3,5-hexa-hydrotriazine, morpholine, phenylmorpholine, thiomorpholine, tetrahydrothiophene, thiazolidine, co-thiocaprolactam, 1,4-thioxane, 1,3-dithiane, 1,4,7-trithiacyclonoriane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, —$OR_4$, —$R_5$, —$OC(O)R_6$, $OC(O)NR_7R_8$, —$C(O)R_9$, —CN, —$NR_{10}R_{11}$, —$SR_{12}$, —$S(O)R_{11}$, —$S(O)_2R_{14}$, —$C(O)OR_{15}$, —$S(O)_2NR_{16}R_{17}$; —$R_{18}R_{19}R_{20}$ wherein $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals.

A preferred class of compounds consists of compounds of Formula V wherein the Y ring system is a radical selected from pyranyl, furyl, tetrahydrofuryl, tetrahydrothienyl, thienyl, oxazolyl, pyrolyl, thiazolyl, imidazolyl, isothiazolyl, isoxazolyl, pyrazolyl, cyclopropyl, cyclobutyl, cyclopentyl, phenyl, and pyridyl.

S and T are selected from aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups may be joined together to form a part of a fused carbocyclic or heterocyclic ring system. R is alkyl, akenyl, alkynyl, optionally substituted aryl and aralkyl.

In another embodiment, in the compound having Formula V, X is ethylene, the Y ring is a furan, R S and T are hydrogen and G is 3-pyridyl.

In another embodiment, the compound having Formula V is bis-[2-(5-pyridin-3-yl-furan-2-yl)-ethyl]-amine or bis-[2-(5-pyridin-3-yl-thiophen-2-yl)-ethyl]-amine.

In another embodiment, the compound having Formula I can be represented by Formula VI:

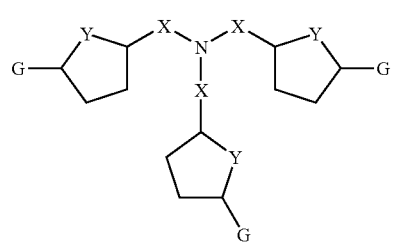

(VI)

wherein G is the A, B ring system defined as in Formula I, X is a saturated carbon chain from $C_2$-$C_8$ and Y is a carbon, oxygen, sulfur, nitrogen or phosphorus atom.

In another embodiment, in a compound having Formula VI, X is ethylene, Y is oxygen and G is 3-pyridyl.

In another embodiment, in a compound having Formula VI, X is ethylene, Y is sulfur and G is 3-pyridyl.

In another embodiment, in a compound having Formula VI, X is ethylene, Y is nitrogen and G is 3-pyridyl.

In another embodiment, the compound having Formula I can be represented by Formula VII:

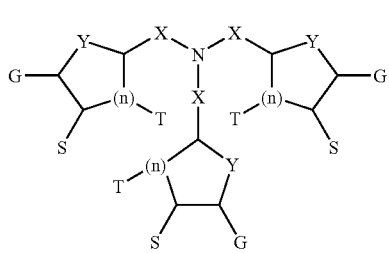

(VII)

wherein G is the A, B ring system defined as in Formula I, X is a saturated carbon chain from $C_2$-$C_8$. Representative heterocycles which make up the Y ring system of Formula VII including the S and T substituents include, but are not limited to pyrrolidine, piperidine, piperazine, heptamethyleneimine, hexamethyleneimine, homopiperazine, perhydroindole, azetidine, 4-piperidinopiperidine, 1-azacycloheptane, imidazoyl, perhydroisoquioline, decahydroquinoline, 1-phenylpiperazine, 4-phenylpiperidine, 1-(fluorophenyl) piperazine, 1,3,5-hexa-hydrotriazine, morpholine, phenylmorpholine, thiomorpholine, tetrahydrotbiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, $-OR_4$, $-R_5$, $-OC(O)R_6$, $OC(O)NR_7R_8$, $-C(O)R_9$, $-CN$, $-NR_{10}R_{11}$, $-SR_{12}$, $-S(O)R_{11}$, $-S(O)_2R_{14}$, $-C(O)OR_{15}$, $-S(O)_2NR_{16}R_{17}$; $-R_{18}NR_{19}R_{20}$ wherein $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals.

A preferred class of compounds consists of compounds of Formula VII wherein the Y ring system is a radical selected from pyranyl, furyl, tetrahydrofuryl, tetrahydrothienyl, thienyl, oxazolyl, pyrolyl, thiazolyl, imidazolyl, isothiazolyl, isoxazolyl, pyrazolyl, cyclopropyl, cyclobutyl, cyclopentyl, phenyl, and pyridyl.

S and T are selected from aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups may be joined together to form a part of a fused carbocyclic or heterocyclic ring system. R is alkyl, akenyl, alkynyl, optionally substituted aryl and aralkyl.

In another embodiment, in a compound having Formula VII, X is ethylene, the Y ring is a furan, S and T are hydrogen and G is 3-pyridyl.

In another embodiment, the compound having Formula VII is tris-[2-(5-pyridin-3-yl-furan-2-yl)-ethyl]-amine or tris-[2-(5-pyridin-3-yl-thiophen-2-yl)-ethyl]-amine.

In another embodiment, the compound having Formula I, is represented by Formula VIII:

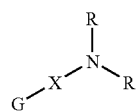

(VIII)

wherein G is the A, B ring system defined as in Formula I, R is alkyl, akenyl, alkynyl, optionally substituted aryl and aralkyl and X is selected from aminoalkyl, aralkyl, aryl, heteroaryl, heteroaralkyl, heteroaralkyloxy, aroyl, aroylalkyl, aryloxy, aryloxyalkyl, hydrido, alkyl, alkenyl, alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups may be joined together to form a part of a fused carbocyclic or heterocyclic ring system.

In another embodiment, in a compound having Formula VII, X is prop-2-ynyl, R is hydrogen and G is 3-pyridyl.

In another embodiment, the compound having Formula VIII is 3-pyridin-3-yl-prop-2-ynylamine.

In another embodiment, the compound having Formula I, is represented by Formula IX:

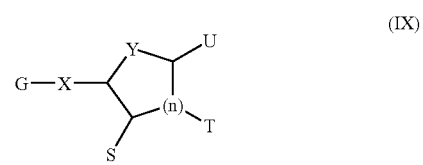

(IX)

wherein G is the A, B ring system defined as in Formula I, X is a saturated carbon chain from $C_2$-$C_8$, alkyl, akenyl, alkynyl, optionally substituted aryl and aralkyl. Representative heterocycles which make up the Y ring system of Formula IX including the S, T and U substituents include, but are not limited to pyrrolidine, piperidine, piperazine, heptamethyleneimine, hexamethyleneimine, homopiperazine, perhydroindole, azetidine, 4-piperidinopiperidine, 1-azacycloheptane, imidazoyl, perhydroisoquioline, decahydroquinoline, 1-phenylpiperazine, 4-phenylpiperidine, 1-(fluorophenyl) piperazine, 1,3,5-hexa-hydrotriazine, morpholine, phenylmorpholine, thiomorpholine, tetrahydrothiophene, thiazolidine, ω-thiocaprolactam, 1,4-thioxane, 1,3-dithiane, 1,4,7-trithiacyclononane, 1,3,5-trithiane, tetrahydropyran, tetramethyleneoxide, tetrahydropyran, 1,3,5-trioxane, oxepane and the like, optionally having one or two ring hydrogens substituted with substituents selected from Cl, Br, I, $-OR_4$, $-R_5$, $-OC(O)R_6$, $OC(O)NR_7R_8$, $-C(O)R_9$, $-CN$, $-NR_{10}R_{11}$, $-SR_{12}$, $-S(O)R_{11}$, $-S(O)_2R_{14}$, $-C(O)OR_{15}$, $-S(O)_2NR_{16}R_{17}$; $-R_{18}NR_{19}R_{20}$ wherein $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, and $R_{20}$ are the same or different and are branched or unbranched alkyl groups from one to eight carbon atoms or hydrogen radicals.

A preferred class of compounds consists of compounds of Formula IX wherein the Y ring system is a radical selected from pyranyl, furyl, tetrahydrofuryl, tetrahydrothienyl, thienyl, oxazolyl, pyrolyl, thiazolyl, imidazolyl, isothiazolyl, isoxazolyl, pyrazolyl, cyclopropyl, cyclobutyl, cyclopentyl, phenyl, and pyridyl.

S, T and U are selected from aminoalkyl, aralkyl, aryl, heteroaryl, heteroaralkyl, heteroaralkyloxy, aroyl, aroylalkyl, aryloxy, acyloxyalkyl, hydrido, alkyl, alkenyl; alkynyl, alkoxy, alkoxyalkyl, acyl, acylalkyl, acyloxy, acyloxyalkyl, halo, haloalkyl, cyano, cyanoalkyl, nitro, nitroalkyl, carboxyl, carboxylalkyl, amino, aminoalkyl, aminocarbonyl, aminocarbonylalkyl, carbamoylalkyl, carbamoylalkoxy, iminoalkyl, imidoalkyl, alkoxycarbonyl, alkoxycarbonylalkyl, alkylamino, alkylaminoalkyl, dialkylamino, dialkylaminoalkyl, arylamino, arylaminoalkyl, hydroxy, hydroxyalkyl, isocyano, isocyanoalkyl, isothiocyano, isothiocyanoalkyl, oximinoalkoxy, morpholino, morpholinoalkyl, azido, azidoalkyl, formyl, formylalkyl, alkylthio, alkylthioalkyl, alkylsulfinyl, alkylsulfinylalkyl, alkylsulfonyl, alkylsulfonylalkyl, aminosulfonyl, arylsulfonyl, N-alkyl-N-arylaminosulfonyl; wherein aryl is selected from phenyl, biphenyl, and naphthyl, and 5- and 6-membered heteroaryl, wherein aryl is optionally substituted. In addition, two adjacent groups may be joined together to form a part of a fused carbocyclic or heterocyclic ring system. R is alkyl, akenyl, alkynyl, optionally substituted aryl and aralkyl.

In another embodiment, in a compound having Formula IX, X is ethynyl, the Y ring is a substituted or unsubstituted thiophene and S, T and U are hydrogen and G is 3-pyridyl.

In another embodiment, the compound having Formula IX is 3-thiophen-2-ylethynyl-pyridine or 3-(3-methyl-thiophen-2-ylethynyl)-pyridine.

In another embodiment, in a compound having Formula IX, X is ethenyl, the Y ring is a substituted or unsubstituted thiophene and S, T and U are hydrogen and G is 3-pyridyl.

In another embodiment, the compound having Formula IX is 3-thiophen-2-ylethenyl-pyridine or 3-[2-(3-methyl-thiophen-2-yl)-vinyl]-pyridine.

In another embodiment, the compound having Formula I, is represented by Formula X:

(X)

wherein C, D and E constitute a 3-membered ring containing carbon, oxygen, sulfur, nitrogen, or phosphorus and X is the A, B ring system defined as in Formula I and I and J are defined as in Formula 1.

In another embodiment, in the compound having Formula X, C, D and E are carbons and I, J and X are selected from aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl, formylalkyl.

In another embodiment, the compound having Formula X is 2-pyridin-3-yl-cyclopropylamine.

In another embodiment, in the compound having Formula X, E is an oxygen and I, J and X are selected from the group consisting of aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl, and formylalkyl.

In another embodiment, in the compound having Formula X, C and D are carbons and E is an sulfur and I, J and X are selected from the group consisting of aminoalkyl, alkylaminoalkyl, arylaminoalkyl, dialkylaminoalkyl, aryl, aralkyl, heteroaryl, heteroaralkyl, alkyl, halo alkyl, cyanoalkyl, iminoalkyl, imidoalkyl, isothiocyanoalkyl, morpholinoalkyl, azidoalkyl and formylalkyl.

In another embodiment, in the compound having Formula X, C and D are carbons and E is an sulfur and I, J and X are selected from the group consisting of aminoalkyl, alkylaminoalkyl, arylaminoalkyl, dialkylaminoalkyl, aryl, aralkyl, heteroaryl, heteroaralkyl, alkyl, haloalkyl, cyanoalkyl, iminoalkyl, imidoalkyl, isothiocyanoalkyl, morpholinoalkyl, azidoalkyl and formylalkyl.

In another embodiment, the composition of the invention further comprises a pharmaceutically acceptable carrier.

In another embodiment, the composition having Formulas I-XII is preferably Formulated as a pharmaceutically acceptable salt, ester or amide thereof.

In yet another embodiment, the present invention provides for a method of decreasing cravings for smoking cigarettes in an animal or human comprising administering a compound of claim 1 by itself or in combination with other agents or biologically or chemically tenable material. In one embodiment, the compound used in the aforementioned method, having Formula I, is β-nicotyrine.

Pharmaceutical Compositions and Methods of Administration

The nicotine-related agents of the present invention are useful for the treatment of diseases and disorders associated with nicotine ingestion and metabolism. For example, the compounds disclosed herein are useful for the treatment of nicotine addiction (e.g., smoking cessation and reduction). In addition, the inhibition of CYP2A6 and/or CYP2A13 inhibits the mutagenic activation of promutagens such as the tobacco-specific nitrosamine, (methylnitrosamino)-1-(3-pyridyl)-1-butanone (NNK) by CYP2A6 or CYP2A13. Thus, the nicotine-related compounds of the present invention can be used for the prophylaxis of lung cell tumorigenesis caused by, e.g., N-nitrosamines.

The agents of the present invention are also useful for the treatment of CNS diseases and disorders amenable to treatment by selective modulation (e.g., stimulation or inhibition) of nicotinic acetylcholine receptors (nAChRs). Such diseases include, for example, neurodegenerative diseases (e.g., Alzheimer's Disease or Parkinson's Disease) and psychiatric disorders such as, e.g., anxiety, attention deficit disorder (ADD), bipolar disorder, and drug abuse. The compounds of the present invention are also useful for other CNS-related therapeutic applications, including, for example, inducing neuroprotective activity in a subject in need thereof (e.g., for treatment or prophylaxis of conditions associated with neurotoxicity), as well as enhancing cognition through selective stimulation of nAChRs.

Accordingly, the present invention further provides pharmaceutical compositions and methods for the treatment of nicotine-related disorders. The nicotine-related agents of the present invention can be delivered or administered to a mammal, e.g., human subject, alone, in the form of a pharmaceutically acceptable salt or hydrolysable precursor thereof, or in the form of a pharmaceutical composition wherein the compound is mixed with suitable carriers or excipient(s) in a therapeutically effective amount. In a preferred embodiment, for treating nicotine addition in a subject and when administered in an appropriate therapeutically effective regime, a sufficient amount of the nicotine-related agent is present to decrease nicotine metabolism so as to predispose the subject to ingest lower amounts of nicotine.

The nicotine-related and other active agents that are used in the methods of the present invention can be administered as pharmaceutical compositions comprising the nicotine-related alkaloid, nicotine metabolite, or nicotine analogue together with a variety of other pharmaceutically acceptable components. Pharmaceutical compositions can be in the form of solids (such as, e.g., powders, granules, dragees, tablets, or pills), semi-solids (such as, e.g., gels, slurries, or ointments), liquids, or gases (such as, e.g., aerosols or inhalants).

Suitable formulations for use in the present invention are found in, for example, *Remington's Pharmaceutical Sciences* (Mack Publishing Company, Philadelphia, Pa., 17th ed. 1985) and Langer, *Science* 249:1527-1533, 1990. The pharmaceutical compositions described herein can be manufactured in a conventional manner, e.g., mixing, dissolving, granulating, dragee-making, levigating, emulsifying, encapsulating, entrapping, or lyophilizing processes.

In preparing the formulations of the present invention, pharmaceutically recognized equivalents of each of the compounds can be alternatively used. These pharmaceutically recognized equivalents can be pharmaceutically acceptable esters, amides, or salts or pharmaceutically acceptable acid addition salts.

A pharmaceutically acceptable salt is a non-toxic metal, alkaline earth metal, or an ammonium salt commonly used in the pharmaceutical industry including, for example, a sodium, potassium, lithium, calcium, magnesium, barium, ammonium, and protamine zinc salt, which is prepared by methods well-known in the art. The term also includes a non-toxic acid addition salt, which is generally prepared by reacting the compounds of the present invention with a suitable organic or inorganic acid. Representative salts include, e.g., hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate.

A pharmaceutically acceptable acid addition salt is a salt that retains the biological effectiveness and properties of the free bases and that is not biologically or otherwise undesirable, formed with inorganic acids such as, e.g., hydrochloric acid, hydrobromic acid, sulfuric acid, nitric acid, phosphoric acid, and the like, and organic acids such as, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid, and the like (see, e.g., Bundgaard ed., *Design of Prodrugs* (Elsevier Science Publishers, Amsterdam 1985)).

The nicotine-related agents can be formulated with common excipients, diluents or carriers, and compressed into tablets, for formulated as elixirs or solutions for convenient oral administration. The nicotine-related agents can also be formulated as sustained release dosage forms and the like.

In order to exert the desired therapeutic effects associated with binding of the nicotinic acetylcholine receptor, the nicotine related agents of the present invention must reach brain cells and brain tissue, requiring their passage from the blood to the brain by crossing the blood brain barrier, comprising the microcapillary membranes of the cerebrovascular endothelium. The present invention provides methods for administering a therapeutically effective dosage regime of the nicotine-related agent to a peripheral tissue in a patient (i.e., tissues other than central nervous system tissues). This can be achieved in various ways, including oral, buccal, rectal, parenteral, intraperitoneal, intradermal, transdermal, intratracheal, and intramuscular administration. Moreover, the nicotine-related agents can be administered in a local rather than systemic manner, in a depot or sustained release formulation.

In addition, the nicotine related agents can be administered in a in a vesicle, in particular a liposome (see, e.g., Langer, supra; Treat et al., In *Liposomes in the Therapy of Infectious Disease and Cancer*, Lopez-Berestein and Fidler eds., Liss, New York, pp. 353-365, 1989).

For injection, the nicotine-related agents of the present invention can be formulated into preparations by dissolving, suspending, or emulsifying them in an aqueous or nonaqueous solvent such as, e.g., vegetable or other similar oils, synthetic aliphatic acid glycerides, esters of higher aliphatic acids, or propylene glycol; and, if desired, with conventional additives such as, e.g., solubilizers, isotonic agents, suspending agents, emulsifying agents, stabilizers, and preservatives. Preferably, for injection, the compounds of the present invention can be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the nicotine-related agent can be formulated readily by combining with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions, and the like, for oral ingestion by a subject to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Particularly suitable excipients include fillers such as, for example, sugars (e.g., lactose, sucrose, mannitol, or sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP). If desired, disintegrating agents can be added, such as the cross-linked polyvinyl pyrrolidone, agar, or alginic acid or a salt thereof such as, e.g., sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, titanium dioxide, lacquer solutions, and/or suitable organic solvents or solvent mixtures. Dyestuffs or pigments can be added to the tablets or dragee coatings for identification or to characterize different combinations of active compound doses.

Pharmaceutical preparations that can be used orally include, for example, push-fit capsules made of gelatin, as well as soft, sealed capsules made of gelatin and a plasticizer, such as, e.g., glycerol or sorbitol. The push-fit capsules can contain the active ingredients in admixture with filler such as, for example, lactose, binders (e.g., starches), and/or lubricants (e.g., talc or magnesium stearate) and, optionally, stabilizers. In soft capsules, the active compounds can be dissolved or suspended in suitable liquids, such as, e.g., fatty oils, liquid paraffin, or liquid polyethylene glycol.

For buccal administration, the compositions can take the form of tablets or lozenges formulated in a conventional manner.

For administration by inhalation, the compounds for use in accordance with the present invention are conveniently delivered in the form of an aerosol spray preparation from pressurized packs or a nebulizer, with the use of a suitable propellant, e.g., dichlorodifluoromethane, trichlorofluoromethane, dicialorotetrafluoroethane, carbon dioxide or other suitable gas, or from propellant-free, dry-powder inhalers. In the case of a pressurized aerosol the dosage unit can be determined by, for example, providing a valve to deliver a metered amount. Capsules and cartridges of, e.g., gelatin for use in an inhaler or insufflator can be formulated containing a powder mix of the compound and a suitable powder base such as, for example, lactose or starch.

Nicotine-related agents of the present invention can be formulated for parenteral administration by injection, e.g., by bolus injection or continuous infusion. Formulations for injection can be presented in unit dosage form, e.g., in ampules or in multidose containers, with an added preservative. The compositions can take such forms as, e.g., suspensions, solutions, or emulsions in oil-based or aqueous vehicles, and can contain formulator agents such as, for example, suspending, stabilizing, and/or dispersing agents.

Pharmaceutical formulations for parenteral administration include aqueous solutions of the active compounds in water-soluble form. Alternatively, suspensions of the active compounds can be prepared as appropriate oily injection suspensions. Suitable lipophilic solvents or vehicles include fatty oils (e.g., sesame oil), synthetic fatty acid esters (e.g., ethyl oleate or triglycerides), or liposomes. Aqueous injection suspensions can contain substances that increase the viscosity of the suspension, such as, for example, sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use.

Nicotine-related agents can also be formulated in rectal compositions such as suppositories or retention enemas, e.g., containing conventional suppository bases such as, for example, cocoa butter, carbowaxes, polyethylene glycols, or other glycerides, all of which melt at body temperature, yet are solidified at room temperature.

In addition to the formulations described previously, the compounds can also be formulated as a depot preparation. Such long-acting formulations can be administered by implantation (for example, subcutaneously or intramuscularly) or by intramuscular injection. Accordingly, for example, the compounds can be formulated with suitable polymeric or hydrophobic materials (e.g., as an emulsion in an acceptable oil) or ion exchange resins, or as sparingly soluble derivatives (e.g., a sparingly soluble salt).

Alternatively, other delivery systems for hydrophobic pharmaceutical compounds can be employed. Liposomes and emulsions are well-known examples of delivery vehicles or carriers for hydrophobic drugs. In some methods, long-circulating, e.g., stealth, liposomes can be employed. Such liposomes are generally described in U.S. Pat. No. 5,013,556 to Woodle et al.

The compounds of the present invention can also be administered by controlled release means and/or delivery devices. In certain variations, a pump is used (see, e.g., Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989). In other embodiments, polymeric materials are used (see, e.g., *Medical Applications of Controlled Release*, Langer and Wise eds., CRC Pres., Boca Raton, Fla., 1974; *Controlled Drug Bioavailability, Drug Product Design and Performance*, Smolen and Bull eds., Wiley, New York, 1984; Ranger and Peppas, *J. Macromol. Sci. Rev. Macromol. Chem.* 23:61, 1983; see also Levy et al., *Science* 228:190, 1985; During et al., *Ann. Neurol.* 25:351, 1989; Howard et al., *J. Neurosurg.* 71:105, 1989). Controlled release means and delivery devices are also described in, e.g., U.S. Pat. Nos. 3,845,770; 3,916,899; 3,536,809; 3,598,123; and 4,008,719.

Certain organic solvents such as, e.g., dimethylsulfoxide (DMSO) also can be employed, although usually at the cost of greater toxicity. Additionally, the compounds can be delivered using a sustained-release system such as, for example, semipermeable matrices of solid hydrophobic polymers containing the therapeutic agent. Various types of sustained-release materials have been established. Sustained-release capsules can, depending on their chemical nature, release the compounds for a few hours up to over 100 days.

The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as, e.g., polyethylene glycols.

For treatment or prophylaxis of diseases or disorders associated with nicotine ingestion (e.g., nicotine addiction or lung cancer), compounds of the present invention may also be administered by incorporating the agent into a nicotine-containing product (for example, a tobacco product such as, e.g., a cigarette). For example, in certain embodiments, a compound of the present invention is sprayed or otherwise applied onto the nicotine-containing product prior to ingestion.

Pharmaceutical compositions suitable for use in accordance with the present invention include compositions wherein the active ingredients are contained in a therapeutically effective amount. The therapeutically effective amounts for the methods of the present invention can depend on a variety of factors, including, e.g., age, body weight, general health, sex, diet, time and manner of administration, rate of excretion, drug combination, the judgment of the treating physician, and the severity of the particular affliction being treated. The amount of active agent will also depend upon the specific activity of the nicotine-related agent and whether that agent is co-administered with any other therapeutic or prophylactic ingredients.

Typically, a subject treated in accordance with the methods provided herein has been diagnosed with a disease or disorder amenable to treatment using a compound of the present invention; has been identified as at risk of a disease or disorder amenable to prophylaxis using the compound; or has otherwise been identified as a subject that will obtain a physiological benefit using the compound (e.g., cognition enhancement). In certain variations, the subject has not been diagnosed with another disease or disorder amenable to treatment using the compounds of the present invention. Further, in some embodiments, the subject is monitored during treatment for one or more symptoms associated with the disease or disorder.

EXAMPLES

The following examples are offered to illustrate, but not to limit, the claimed invention.

The numbering of specific compounds in the following examples are specific to the particular example in which it is used. Accordingly, the number assigned to a specific compound in one example does not necessarily correspond to the numbering used for the same compound in a different example.

Example 1

Chemical Synthesis of Substituted Tetrahydrofuran Nicotine Analogs

The synthesis of analogs of nicotine where the pyrrolidine ring was replaced with a substituted tetrahydrofuran ring system to mimic the parent compound were synthesized in a multistep sequence that provided the target compounds in overall acceptable yields. The synthesis is shown in FIG. 1. Generally, the bromide was derivatized with various functional groups to obtain the desired target compounds. The target compounds were fully characterized spectrally and subjected to biological evaluation. Purity was evaluated by HPLC analysis of the compounds.

Example 2

Chemical Synthesis of Substituted Heteroaryl Analogs of Nicotine

Figure 2:
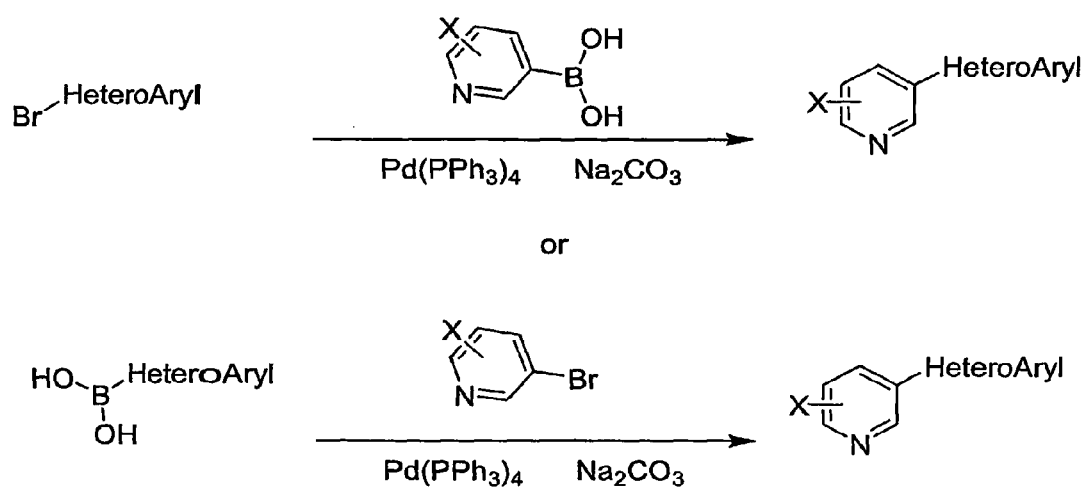
FIG. 2 depicts synthesis of substituted heteroaryl analogs of nicotine as described in Example 2.

The synthesis of analogues of nicotine where the pyrrolidine ring was replaced with a heteroaryl group to mimic the parent compound is shown in FIG. 2. The appropriate aryl bromide was treated with tetrakis(triphenylphosphine)palladium(0), sodium carbonate as the base and appropriate boronic acid for 1 hour at elevated temperature. The products were obtained after workup and column chromatography in yields ranging from 40-95%. The products were characterized by NMR and mass spectrometry and subjected to biological evaluation.

Example 3

Chemical Synthesis of Substituted Carbocyclic Analogs of Nicotine

Figure 3:
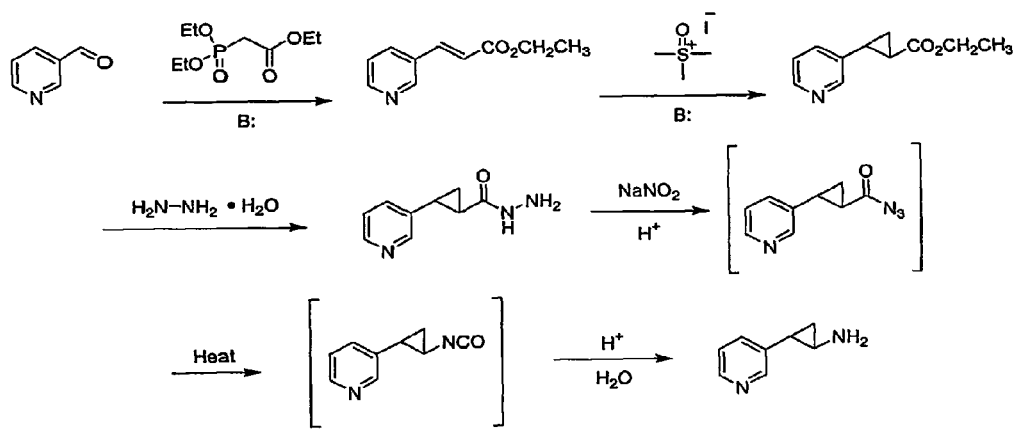
FIG. 3 depicts synthesis of substituted carbocyclic analogs of nicotine as described in Example 4.

The synthesis of analogues of nicotine where the pyrrolidine ring was replaced with a substituted cyclopropyl ring system to mimic the parent compound is shown in FIG. 3.

Example 4

Evaluation of Nicotine, Nicotine Related Alkaloids and Nicotine Metabolites as Inhibitors of CYP2A6

The work described in this example shows the feasibility of using natural nicotine, nicotine related alkaloids and nicotine metabolites as CYP2A6 inhibitors that cause selective smoking cessation and decreased lung cancer risk. S-(−)-Nicotine and 13 of the most prevalent nicotine-related alkaloids and metabolites (i.e., S-(−)-nomicotine, myosmine, β-nicotyrine, S-cotinine, S-norcotinine, S-(−)-nicotine N-1'-oxide, S-(−)-nicotine $\Delta^{1'-5'}$-iminium ion, S-(−)-anabasine, S-(−)-N-methylanabasine, anabaseine, S-(−)-anatabine, nicotelline, and 2,3'-bipyridyl) were postulated to be inhibitors of CYP2A6-mediated nicotine and N-nitrosamine metabolism and will decrease a persons likelihood to become dependent on nicotine and inhibit the onset of lung cancer. As shown in Table 1, five tobacco alkaloids (i.e., β-nicotyrine, (S)-anatabine, (S)-anabasine and 2,3'-bipyridyl) showed significant CYP2A6 inhibition with β-nicotyrine being the most potent with an $IC_{50}$ value of 2.2±0.22 μM. Using β-nicotyrine as an example, it may be feasible to increase the level of this volatile molecule in the tobacco plant by an increase in the alkaloid's biosynthetic pathway using genetic and biochemical techniques or it is possible to dope the final tobacco product with the natural compound so that it's beneficial inhibitory effects can be utilized. This may be a possible way of treating lung cancer in patients who have tried to quit using tobacco in the past and have failed.

Example 5

Evaluation of Nicotine, Nicotine Related Alkaloids, Nicotine Metabolites and Nicotine Analogs as Inhibitors of CYP2A6 Mediated Coumarin 7-Hydroxylation The inhibition of human CYP2A6-mediated 7-hydroxy coumarin formation was evaluated in the presence of 95 selected test compounds in a standard assay (Greenlee et al., *J Pharmacol Exp Ther*, 1978). Our first studies were with highly purified human CYP2A6 that provided a convenient and relatively high-throughput measure of CYP2A6 inhibition. Full dose-response $IC_{50}$ values (nine concentrations) were determined (Table 1).

Example 6

CYP3A4 Inhibition Assay (Testosterone Hydroxylase)

To gain insight into the selectivity of the synthetic compounds, nicotine, nicotine related alkaloids and nicotine metabolites for inhibition of other CYPs, we examined the major CYP present in human liver (i.e., CYP 3A4). That the CYP2A6 inhibitors showed low or no inhibitory activity against CYP3A4 suggests that the inhibitors examined selectively inhibited CYP2A6. A typical incubation mixture (final volume 0.25 mL) contained 50 mM Tris buffer (pH 7.5), 0.5 mM $NADP^+$, 2.0 mM G6P, 1 U of G6P dehydrogenase, 4.3 mg of rat cytosol and 0.6 mg DETAPAC and the inhibitor was added last as to minimize interaction with the protein. After mixing on ice, the reaction was initiated by the addition of substrate and incubated at 37° C. with shaking in air. Organic extracts were injected onto a Hitachi L-7100 system equipped with a Hitachi L-7400 UV detector. Separations were done with an Altex Ultrasphere ODS (4.6 mm×250 mm, 5 μm) column. The analytes were eluted with an isocratic solvent system consisting of water/acetonitrile/methanol (30:10:60, v/v/v) at a flow rate of 1.0 mL/min. Testosterone and 6-hydroxytestosterone were efficiently separated by this system with retention times of 7.95 and 3.94 min, respectively. Quantification of substrate and metabolite was determined from peak areas of the chromatogram and comparison with standard curves. $IC_{50}$ values were determined as described below. For each assay, the reaction was a linear function of time for 60 min and of protein concentration from 0.2 to 1 mg of protein per reaction well. (Table 1, Buters et al., *Drug. Metab. Dispos.*, 1994).

Example 7

Data Analysis

GraphPad Prism was used to convert all kinetic data into $IC_{50}$ values. Each kinetic determination was reported as the mean±SD of at least four determinations.

TABLE 1

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 1 | | 0.172 ± 0.017 | 58.72 15.33 | 347 |
| 2 | 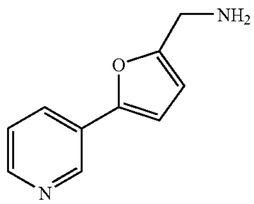 | .268 ± 0.021 | 47.17 ± 18.07 | 174 |
| 1 | | 0.172 ± 0.017 | 58.72 15.33 | 347 |
| 3 | 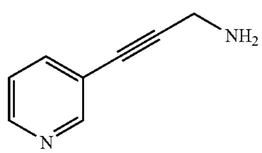 | .514 ± 0.055 | 365 128 | 710 |
| 4 | 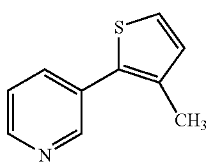 | 0.622 ± 0.087 | 5.99 ± 1.29 | 10 |
| 5 | 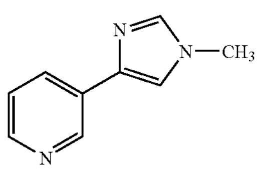 | 0.748 ± 0.1 | 261.9 ± 63.42 | 349 |
| 6 Tranylcypromine | | 0.97 ± 0.22 | N/D[b] | N/D[b] |
| 7 | 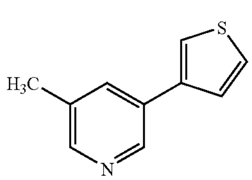 | 1.0 ± 0.29 | N/D[b] | N/D[b] |

TABLE 1-continued
Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.
| Compound ID | Chemical Structure | CYP2A6 IC$_{50}$ (μM) | CYP3A4 IC$_{50}$ (μM) | Selectivity Ratio[a] |
|---|---|---|---|---|
| 8 | 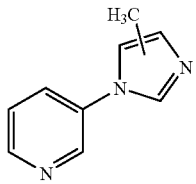 | 1.02 ± 0.23 | 109 ± 45.86 | 109 |
| 9 | 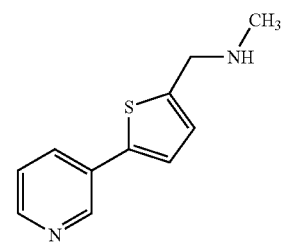 | 1.10 ± 0.13 | N/D[b] | N/D[b] |
| 10 | 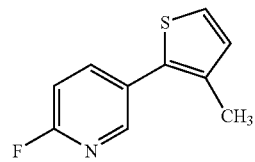 | 1.29 ± 0.14 | 39.08 ± 12.76 | 30 |
| 11 | 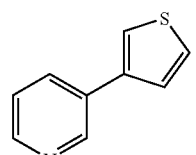 | 1.37 ± 0.23 | 55.91 ± 19.17 | 40 |
| 12 | 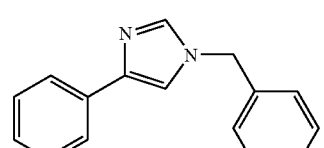 | 1.39 ± 0.19 | N/D[b] | N/D[b] |
| 1 | 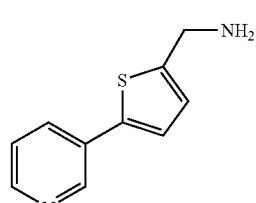 | 0.172 ± 0.017 | 58.72 15.33 | 347 |
| 13 | 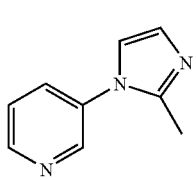 | 1.50 ± 0.35 | 152 ± 70 | 101 |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 14 | 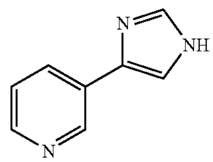 [SMILES: c1cncc(-c2c[nH]cn2)c1] | 1.51 ± 0.31 | 139.9 ± 140.3 | 93 |
| 15 | 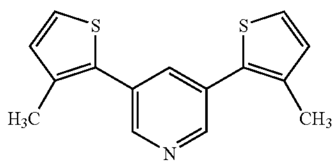 [SMILES: Cc1ccsc1-c1cncc(-c2sccc2C)c1] | 1.63 ± 0.65 | N/D[b] | N/D[b] |
| 16 | 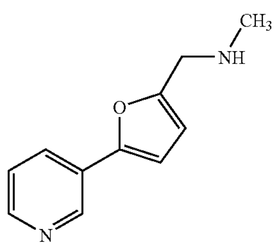 | 1.65 ± 0.33 | N/D[b] | N/D[b] |
| 17 | 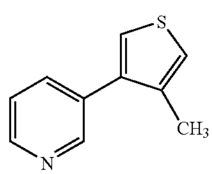 | 1.85 ± 0.5 | <25 | <13 |
| 18 | 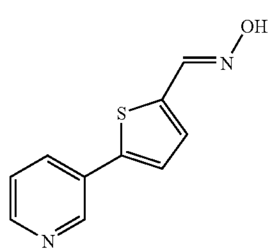 | 1.93 ± 0.33 | 12.98 ± 3.253 | 7 |
| 19 β-Nicotyrine | 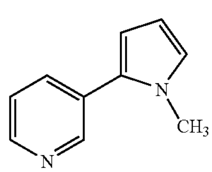 | 2.2 ± 0.22 | N/D[b] | N/D[b] |
| 20 | 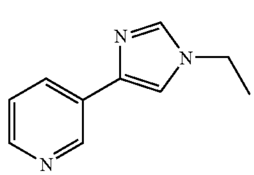 | 3.14 ± 0.33 | N/D[b] | N/D[b] |

TABLE 1-continued
Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.
| Compound ID | Chemical Structure | CYP2A6 IC$_{50}$ (μM) | CYP3A4 IC$_{50}$ (μM) | Selectivity Ratio[a] |
|---|---|---|---|---|
| 21 | 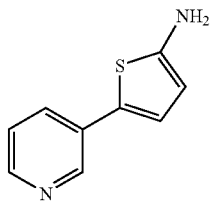 | 3.51 ± 0.28 | 1.59 ± 1.63 | 0.45 |
| 1 | 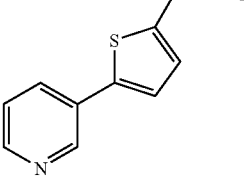 | 0.172 ± 0.017 | 58.72 15.33 | 347 |
| 22 | 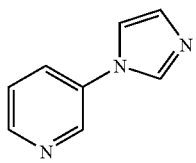 [SMILES: c1cncc(-n2ccnc2)c1] | 3.74 ± 0.78 | 77.54 ± 14.62 | 20 |
| 23 | 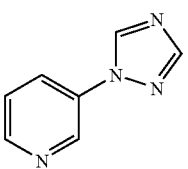 [SMILES: c1cncc(-n2cncn2)c1] | 4.2 ± 0.8 | N/D[b] | N/D[b] |
| 24 | 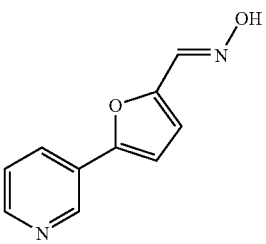 [SMILES: O/N=C/c1ccc(-c2cccnc2)o1] | 4.24 ± 0.49 | >400 | >95 |
| 25 | 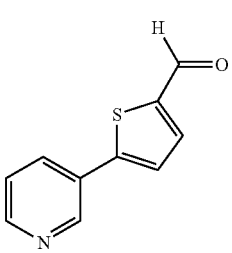 [SMILES: O=Cc1ccc(-c2cccnc2)s1] | 4.77 ± 0.74 | 23.93 ± 7.323 | 6 |
| 26 | 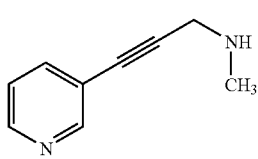 | 5.36 ± 0.61 | N/D[b] | N/D[b] |

TABLE 1-continued
Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.
| Compound ID | Chemical Structure | CYP2A6 IC$_{50}$ (μM) | CYP3A4 IC$_{50}$ (μM) | Selectivity Ratio[a] |
|---|---|---|---|---|
| 27 | 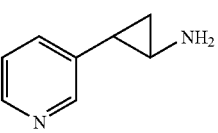 | 5.77 ± 0.36 | N/D[b] | N/D[b] |
| 28 | 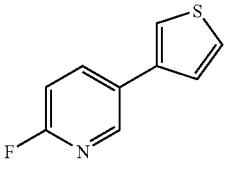 [SMILES: Fc1ccc(-c2ccsc2)cn1] | 5.84 ± 1.18 | 114 ± 24.85 | 20 |
| 29 | 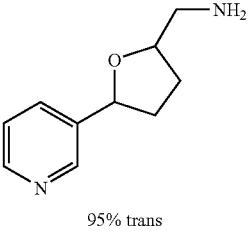 [SMILES: NCC1CCC(c2cccnc2)O1] 95% trans | 5.9 ± 3 | 64.71 ± 13.65 | 11 |
| 30 | 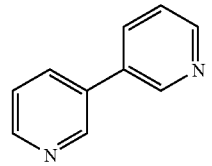 [SMILES: c1cncc(-c2cccnc2)c1] | 6.6 ± 8.1 | >400 | >61 |
| 1 | 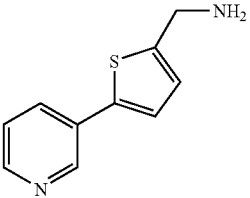 | 0.172 ± 0.017 | 58.72 15.33 | 347 |
| 31 | 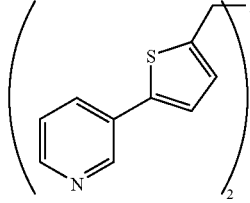 | 7.44 ± 1.32 | 56.99 ± 21.3 | 8 |
| 32 | 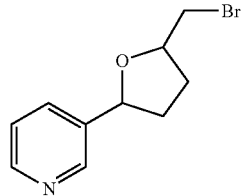 [SMILES: BrCC1CCC(c2cccnc2)O1] | 7.65 ± 2.04 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 33 | 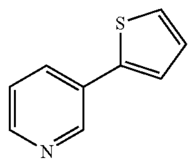 [SMILES: c1cncc(-c2cccs2)c1] | 7.8 ± 3.74 | N/D[b] | N/D[b] |
| 34 | 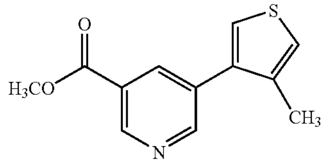 [SMILES: COC(=O)c1cncc(-c2cscc2C)c1] | 8.0 ± 0.8 | N/D[b] | N/D[b] |
| 35 | 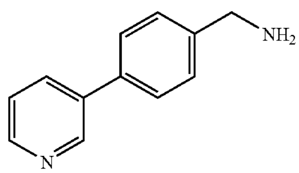 [SMILES: NCc1ccc(-c2cccnc2)cc1] | 8.6 ± 1.7 | N/D[b] | N/D[b] |
| 36 | 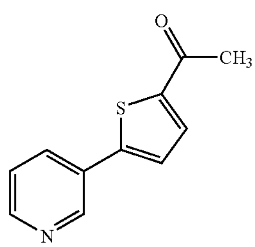 | 8.61 ± 1.33 | 26.9 ± 9.174 | 3 |
| 37 | 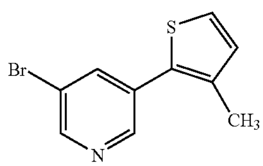 | 8.9 ± 1.13 | N/D[b] | N/D[b] |
| 38 | (50:50 cis:trans) | 9.42 ± 0.81 | N/D[b] | N/D[b] |
| 1 | 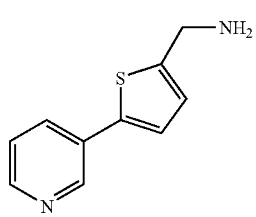 | 0.172 ± 0.017 | 58.72 15.33 | 347 |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 39 | 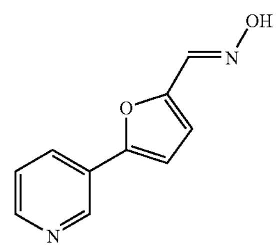 [SMILES: O/N=C/c1ccc(-c2cccnc2)o1] | 9.75 ± 0.91 | >400 | 41 |
| 40 | 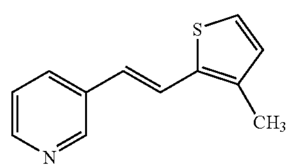 | ~10 | N/D[b] | N/D[b] |
| 41 | 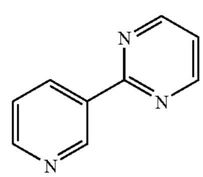 [SMILES: c1cnc(-c2cccnc2)nc1] | 10.88 ± 2.13 | >400 | 37 |
| 42 | 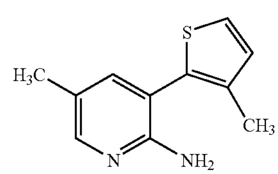 | 11.5 ± 2.1 | N/D[b] | N/D[b] |
| 43 | 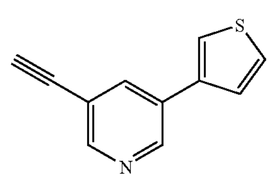 | 12.9 ± 2.3 | N/D[b] | N/D[b] |
| 44 | 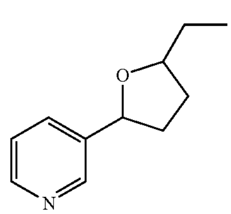 | 13.6 ± 3.48 | N/D | N/D |
| 45 | 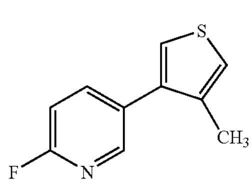 | 15.8 ± 3 | 114 ± 24.85 | 7 |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 46 | 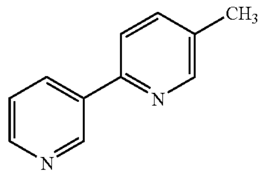 | 16.5 ± 3.8 | 84.23 ± 19.5 | 5 |
| 47 | 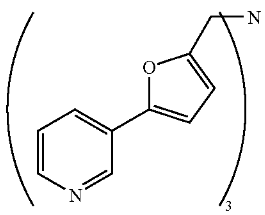 | 16.9 ± 4.8 | N/D[b] | N/D[b] |
| 1 | 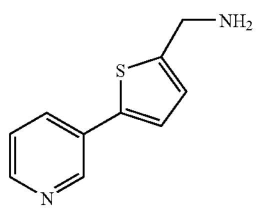 [SMILES: NCc1ccc(-c2cccnc2)s1] | 0.172 ± 0.017 | 58.72 15.33 | 347 |
| 48 | 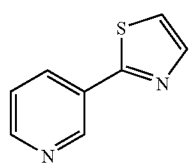 [SMILES: c1cncc(-c2nccs2)c1] | 19 ± 3.4 | N/D[b] | N/D[b] |
| 49 | 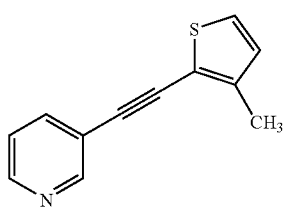 | 20.2 ± 2.4 | N/D[b] | N/D[b] |
| 50 Anatabine | 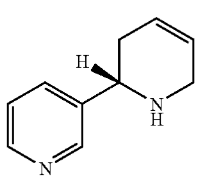 [SMILES: C1=CC[C@@H](c2cccnc2)NC1] | 23 ± 3.6 | N/D[b] | N/D[b] |
| 51 | 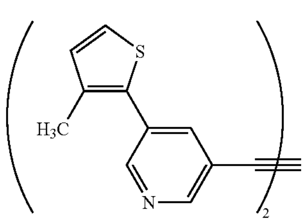 | 21.5[c] | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 52 | 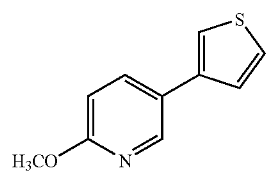 [SMILES: COc1ccc(-c2ccsc2)cn1] | >25 | N/D[b] | N/D[b] |
| 53 | 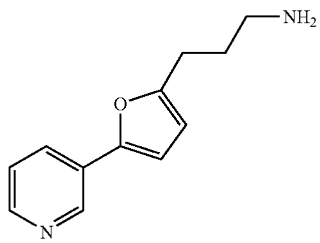 [SMILES: NCCCc1ccc(-c2cccnc2)o1] | >25 | N/D[b] | N/D[b] |
| 54 Nicotine | 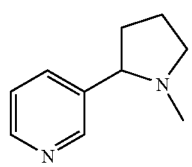 | 26.3 ± 3.4 | 142.4 ± 15.7 | 5 |
| 55 | 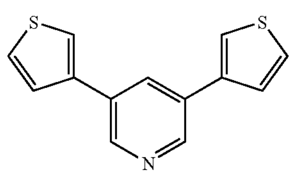 [SMILES: c1cc(-c2cncc(-c3ccsc3)c2)cs1] | 26.7 ± 4.6 | N/D[b] | N/D[b] |
| 1 | 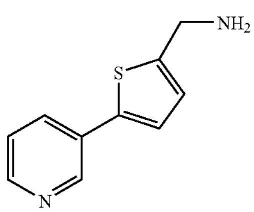 [SMILES: NCc1ccc(-c2cccnc2)s1] | 0.172 ± 0.017 | 58.72 15.33 | 347 |
| 56 | 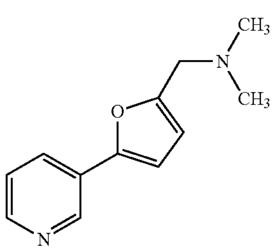 | 28.3 ± 18.3 | N/D[b] | N/D[b] |
| 57 | 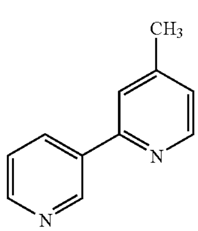 | 30.4 ± 4.59 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 58 | 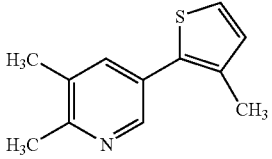 | 32.3 ± 2.9 | N/D[b] | N/D[b] |
| 59 Anabasine | 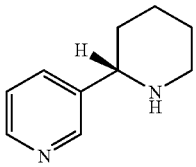 [SMILES: c1cncc([C@@H]2CCCCN2)c1] | 32.4 ± 7.3 | N/D[b] | N/D[b] |
| 60 | 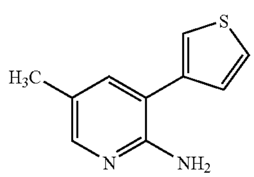 | 33.2 ± 41.7[b] | N/D[b] | N/D[b] |
| 61 | 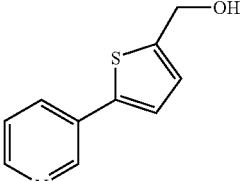 | 33.5 ± 4.42 | N/D[b] | N/D[b] |
| 62 | 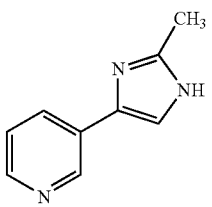 | 37.1 ± 5.8 | N/D[b] | N/D[b] |
| 63 | 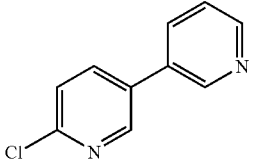 [SMILES: Clc1ccc(-c2cccnc2)cn1] | 37.8 ± 15.2 | N/D[b] | N/D[b] |
| 1 | 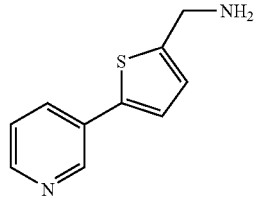 | 0.172 ± 0.017 | 58.72 15.33 | 347 |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 64 | 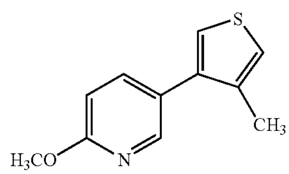 | 39.8 ± 4.5 | N/D[b] | N/D[b] |
| 65 | 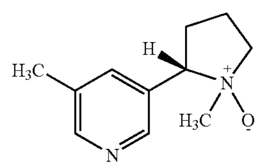 | 46.0 ± 5.2 | N/D[b] | N/D[b] |
| 66 2,3'-Bipyridyl | 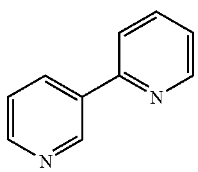 [SMILES: c1ccc(-c2cccnc2)nc1] | 46.1 ± 7.1 | N/D[b] | N/D[b] |
| 67 | 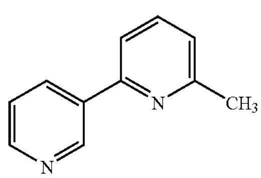 | 58.9 ± 11.9 | N/D[b] | N/D[b] |
| 68 | 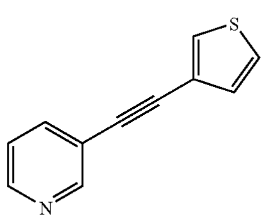 [SMILES: C(#Cc1ccsc1)c1cccnc1] | 61.2 ± 11.5 | N/D[b] | N/D[b] |
| 69 | 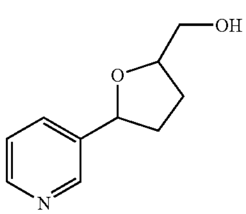 [SMILES: OCC1CCC(c2cccnc2)O1] | 61.4 ± 17.7 | N/D[b] | N/D[b] |
| 70 | 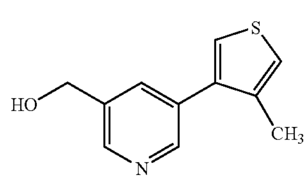 | 65.0 ± 7.0 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 71 | 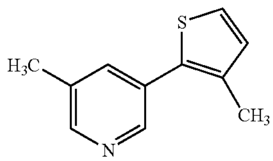 | 66.0 ± 9.0 | N/D[b] | N/D[b] |
| 72 | 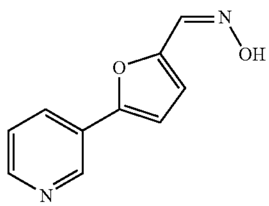 [SMILES: O/N=C\c1ccc(-c2cccnc2)o1] | 82.3 ± 7.3 | >400 | 5 |
| 1 | 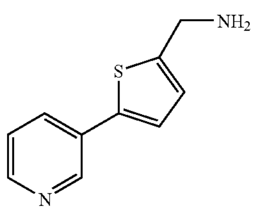 [SMILES: NCc1ccc(-c2cccnc2)s1] | 0.172 ± 0.017 | 58.72 15.33 | 347 |
| 73 | 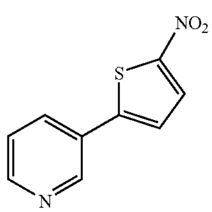 [SMILES: O=[N+]([O-])c1ccc(-c2cccnc2)s1] | 118 ± 14 | N/D[b] | N/D[b] |
| 74 Anabaseine | 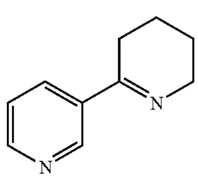 [SMILES: c1cncc(C2=NCCCC2)c1] | 120 ± 38 | N/D[b] | N/D[b] |
| 75 | 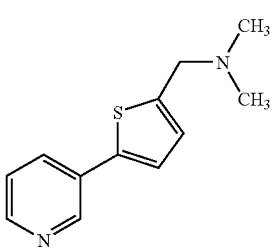 | 133 ± 20 | N/D[b] | N/D[b] |
| 76 | 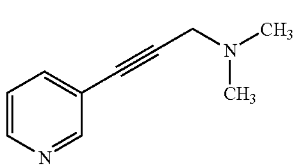 | 136 ± 47 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 77 | 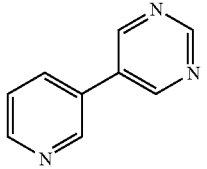 [SMILES: c1cncc(-c2cncnc2)c1] | 165 ± 25 | N/D[b] | N/D[b] |
| 78 | 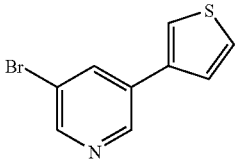 [SMILES: Brc1cncc(-c2ccsc2)c1] | 165 ± 16 | N/D[b] | N/D[b] |
| 79 Myosmine | 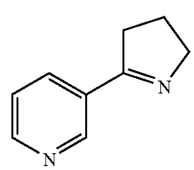 [SMILES: c1cncc(C2=NCCC2)c1] | 187 ± 47 | N/D[b] | N/D[b] |
| 80 | 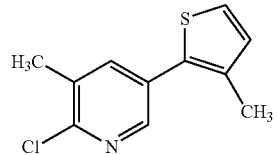 | 191 ± 36 | N/D[b] | N/D[b] |
| 81 | 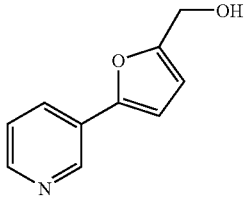 [SMILES: OCc1ccc(-c2cccnc2)o1] | 211 ± 100 | N/D[b] | N/D[b] |
| 1 | 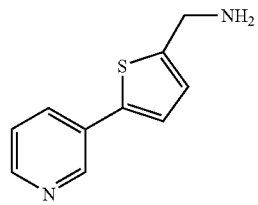 | 0.172 ± 0.017 | 58.72 15.33 | 347 |
| 82 | 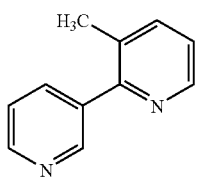 | 262 ± 69 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 83 | 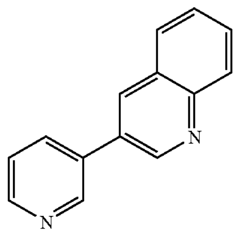 [SMILES: c1cncc(-c2cnc3ccccc3c2)c1] | 267 ± 245 | N/D[b] | N/D[b] |
| 84 Norcotinine | 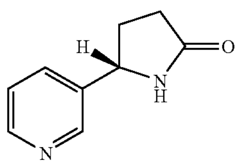 | 274 ± 37 | N/D[b] | N/D[b] |
| 85 | 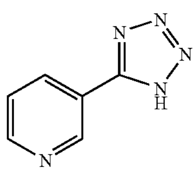 [SMILES: c1cncc(-c2nnn[nH]2)c1] | 389 ± 68 | N/D[b] | N/D[b] |
| 86 | 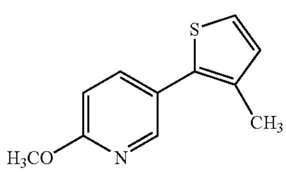 | ≥400 | N/D[b] | N/D[b] |
| 87 | 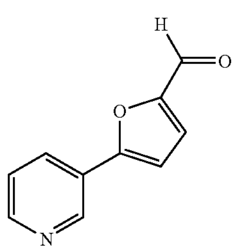 [SMILES: O=Cc1ccc(-c2cccnc2)o1] | ≥400 | N/D[b] | N/D[b] |
| 88 | 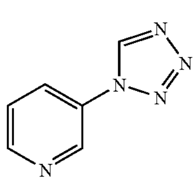 [SMILES: c1cncc(-n2cnnn2)c1] | 408 ± 88 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (μM) | CYP3A4 IC$_{50}$ (μM) | Selectivity Ratio[a] |
|---|---|---|---|---|
| 89 | 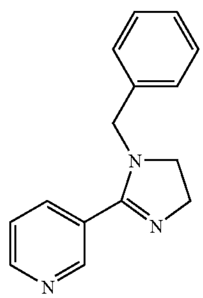 [SMILES: c1ccc(CN2CCN=C2c2cccnc2)cc1] | ≥400 | N/D[b] | N/D[b] |
| 1 | 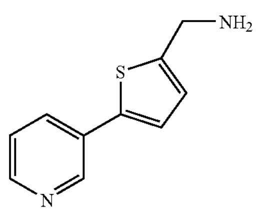 | 0.172 ± 0.017 | 58.72 15.33 | 347 |
| 90 Nornicotine | 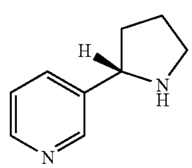 [SMILES: c1cncc([C@@H]2CCCN2)c1] | ≥400 | N/D[b] | N/D[b] |
| 91 Cotinine | 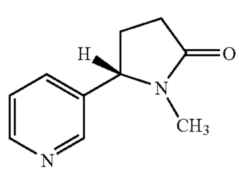 | ≥400 | N/D[b] | N/D[b] |
| 92 Nicotine N-1'-Oxide | 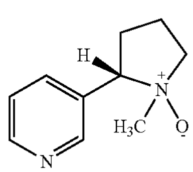 | ≥400 | N/D[b] | N/D[b] |
| 93 Nicotine Δ$^{1'-5'}$-iminium ion | | ≥400 | N/D[b] | N/D[b] |
| 94 N-Methylanabasine | 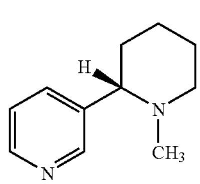 | ≥400 | N/D[b] | N/D[b] |

TABLE 1-continued

Evaluation of nicotine, nicotine related alkaloids, nicotine metabolites and nicotine analogs as inhibitors of CYP2A6 mediated coumarin 7-hydroxylation and CYP3A4 mediated testosterone 6-hydroxylation.

| Compound ID | Chemical Structure | CYP2A6 IC$_{50}$ (µM) | CYP3A4 IC$_{50}$ (µM) | Selectivity Ratio[a] |
|---|---|---|---|---|
| 95 Nicotelline | 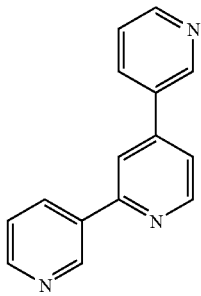 [SMILES: c1cncc(-c2ccnc(-c3cccnc3)c2)c1] | ≥400 | N/D[b] | N/D[b] |

[a]Selectivity Ratio: IC$_{50}$ (Inhibition of CYP3A4)/IC$_{50}$ (Inhibition of CYP2A6).
[b]N/D = Not Determined

Example 8

Effect of Nicotine Analogues on Microsomal Human CYP2A6-Mediated Nicotine Oxidase Activity Highly active compounds were next evaluated for their ability to inhibit human liver microsome-mediated oxidation of tritiated nicotine (Table 2). For each determination, cold microsomes (of predetermined CYP2A6 activity) was added to the NADPH-generating system containing 50 mM Tris (pH=7.4) and DETAPAC (to prevent metal-catalyzed autooxidation) and inhibitor. Because rat liver cytosol has little CYP2A6 activity and high levels of aldehyde oxidase, 0.2 mg/incubation was used to quantitatively convert the nicotine iminium ion to cotinine. To initiate the reaction, substrate was added to the briefly warmed (20 sec) incubation and continued for a defined amount of time (20 min) (Cashman et al., *Chem Res Toxicol*, 1992). Previously, we determined that cotinine formation in the assay was linearly dependent on protein concentration (up to 1.2 mg of protein) and of time (up to 30 min). For initial evaluation of a large number of samples, [$^3$]H-nicotine was used in a TLC/radiometric format. The assay incubations described above were stopped with 1 volume of CH$_3$CN and 25 µL of the quenched incubation (with cold nicotine and cotinine standards to help visualize by UV-vis) and applied to a LK5DF preabsorbent TLC plate with MeOH/CH$_2$Cl$_2$/20% TCA (5:93.5:1.0, v:v) that gives R$_f$ values of 0.48 and 0.3 for cotinine and nicotine, respectively. Quantification of scrapped bands was by scintillation counting.

TABLE 2

Effect of Nicotine Analogues on Microsomal Human CYP2A6-Mediated Nicotine Oxidase Activity.

| Compound | Compound | CYP2A6 IC$_{50}$ (µM) |
|---|---|---|
| 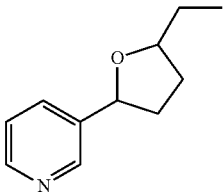 | 44 | 0.02 ± 0.02 |
| 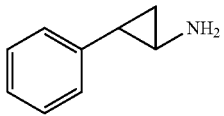 | 6 Tranylcypromine | 0.08 ± 0.01 |
| 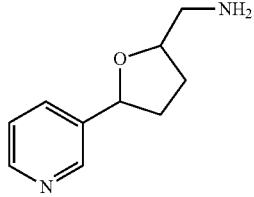 95% trans | 29 | 0.33 ± 0.13 |
| 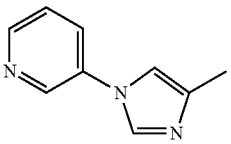 | 8 | 0.36 ± 0.18 |

TABLE 2-continued

Effect of Nicotine Analogues on Microsomal Human CYP2A6-Mediated Nicotine Oxidase Activity.

| Compound | Compound | CYP2A6 IC$_{50}$ (μM) |
|---|---|---|
| 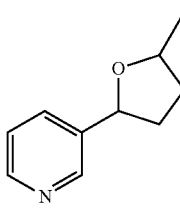 | 32 | 0.36 ± 0.18 |
| 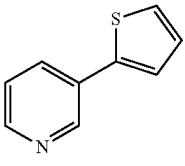 | 33 | 3.05 ± 0.72 |
| 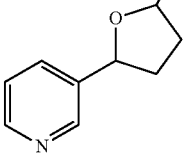 50:50 cis:trans | 38 | 5.21 ± 1.68 |

Example 9

AChBP Fluorescence Quenching Assay

To examine the degree of interaction with the nicotinic acetylcholine receptor, we examined the binding interaction of the synthetic inhibitors with the Ach binding protein (AchBP) from the fresh water snail (Table 3). This has been shown to be an excellent model system for the mammalian nicotinic acetylcholine receptor. Following incubation of 20 nM AchBP (a structural homologue of the extracellular domain of the nicotinic acetylcholine receptor from the fresh water snail *Lymnaea stagnalis*) with the nicotine analog, the samples were excited at 280 nm and the emission 340 nm was monitored and the results compared with the emission of a corresponding amount of AChBP that had been treated with buffer (Hansen et al., *J Biol Chem*, 2002).

TABLE 3

Effect of Nicotine Analogues on Coumarin Hydroxylase Activity and Interaction with the Acetylcholine Binding Protein.

| Compound ID | Chemical Structure | 2A6 IC$_{50}$ (μM) | AchBP* |
|---|---|---|---|
| 6 Tranyl-cypromine | 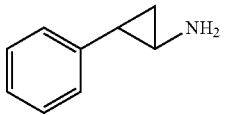 | 0.97 ± 0.22 | ++ |

TABLE 3-continued

Effect of Nicotine Analogues on Coumarin Hydroxylase Activity and Interaction with the Acetylcholine Binding Protein.

| Compound ID | Chemical Structure | 2A6 IC$_{50}$ (μM) | AchBP* |
|---|---|---|---|
| 8 | 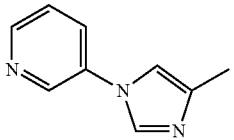 | 1.02 ± 0.23 | + |
| 14 | 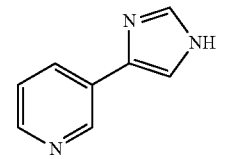 [SMILES: c1cncc(-c2c[nH]cn2)c1] | 1.51 ± 0.31 | -- |
| 17 | 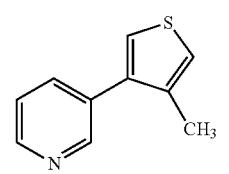 | 1.85 ± 0.5 | + |
| 29 | 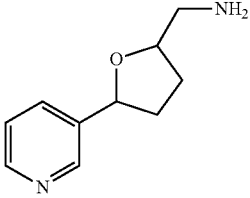 95% trans | 5.9 ± 3 | + |
| 30 | 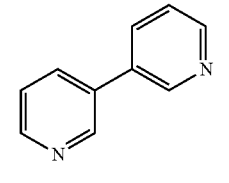 [SMILES: c1cncc(-c2cccnc2)c1] | 6.6 ± 8.1 | + |
| 32 | 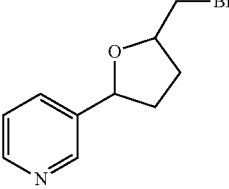 | 7.65 ± 2.04 | ++ |
| 33 | 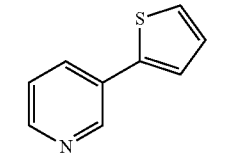 | 7.8 ± 3.74 | + |

TABLE 3-continued

Effect of Nicotine Analogues on Coumarin Hydroxylase Activity and Interaction with the Acetylcholine Binding Protein.

| Compound ID | Chemical Structure | 2A6 IC$_{50}$ (μM) | AchBP* |
|---|---|---|---|
| 38 | NH$_2$ (50:50 cis:trans) | 9.42 | + |
| 44 | 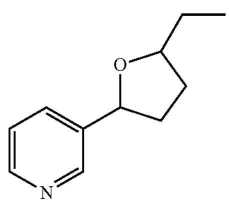 | 13.6 ± 3.48 | − |
| 69 | OH | 61.4 ± 17.7 | − |

*++ = strong fluorescence quenching, + = modest fluorescence quenching, − = no fluorex-cence quenching, −− = fluorescence enhancement

CYP2A6 Inhibition

Figure 4:
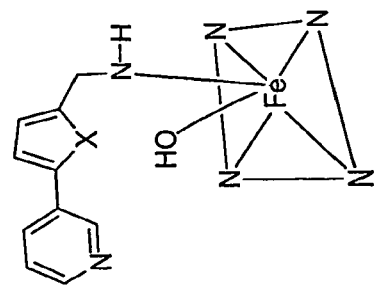
FIG. 4 depicts a proposed interaction of CYP2A6 with the nicotine analog inhibitors.
Figure 4:
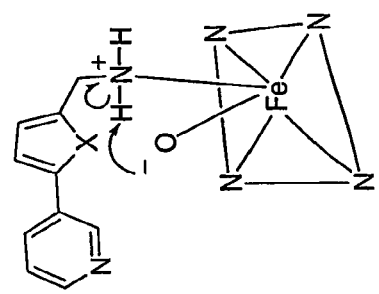
Figure 4:
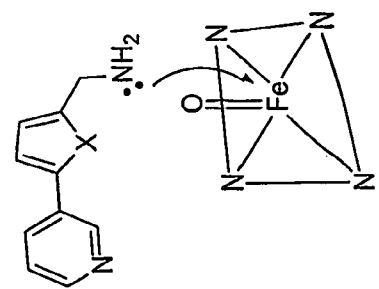
Figure 5A:
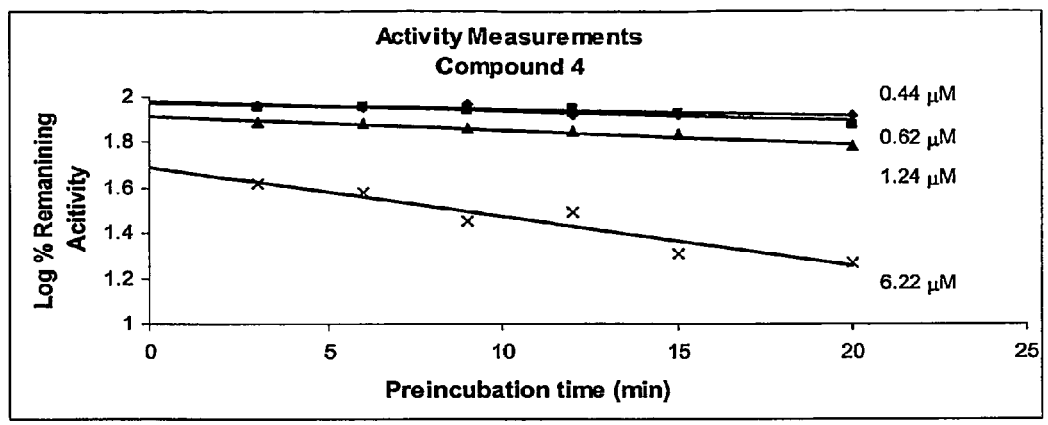
FIGS. 5A and 5B depict the kinetic characterization of compound 4 of Example 10.
Figure 5B:
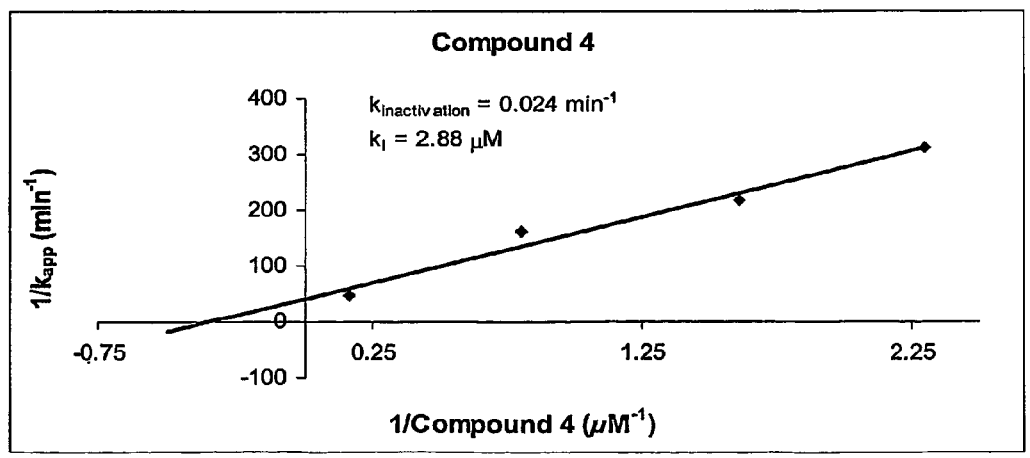
Figure 6A:
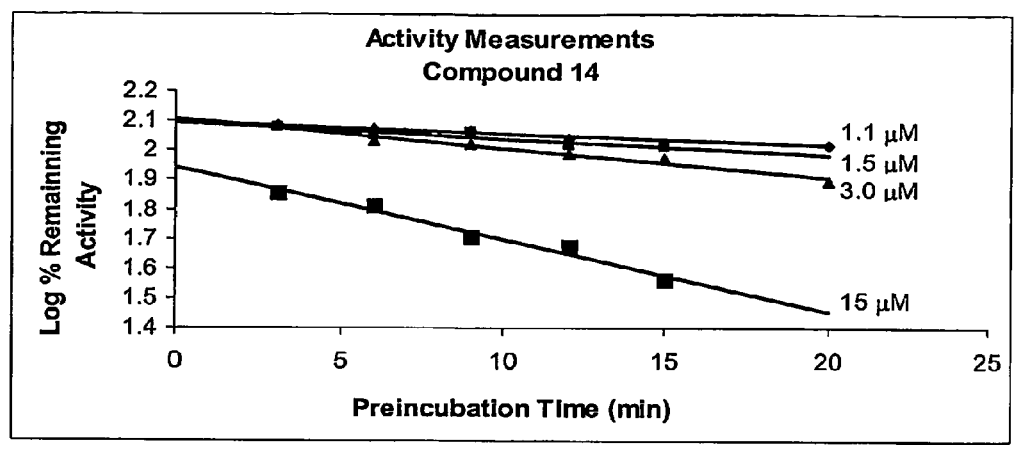
FIGS. 6A and 6B depict the kinetic characterization of compound 14 of Example 10.
Figure 6B:
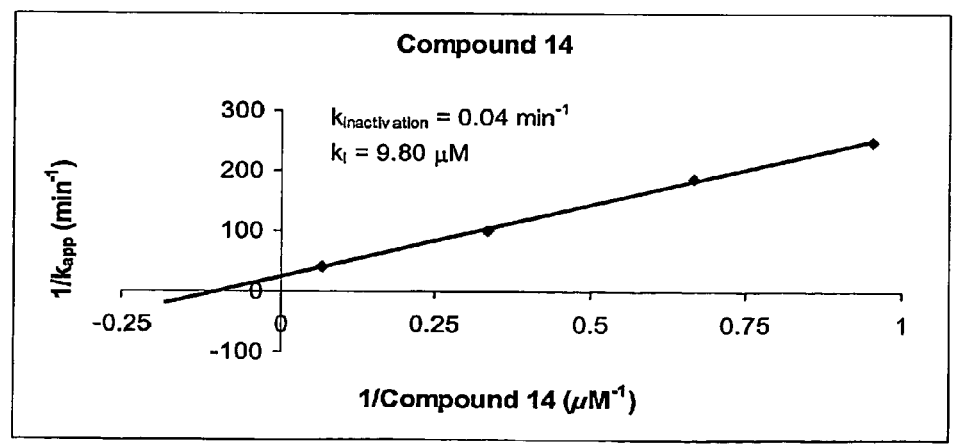

The chemical synthesis of the lead compounds arose from the recognition that the target compounds possessed structural similarity to nicotine. A focused library of analogs was then created to explore various aspects of structure-function. Specifically, side chain groups were introduced that were developed to selectively interact with the heme iron of CYP2A6. A proposed model of CYP2A6 interaction is presented in FIG. 4.

As shown in Table 1, significant inhibition of CYP2A6-mediated coumarin 7-hydroxylation was observed for compounds 1, 2 and 3, but when a tetrahydrofuran ring is incorporated into the structure, as in compounds 29 and 38 the inhibitory potency was significantly diminished. Although the inhibitory potency of the tetrahydrofuran analogs is lower than that of its aromatic counterpart, the tetrahydrofuran ring possesses two centers of chirality and separation of the cis from the trans diastereomers afforded an opportunity to examine the stereoselectivity of CYP2A6 inhibition. Inhibition of CYP2A6 was shown to be stereoselective because the amine isomeric mixture (compound 38, 50:50, cis:trans) was almost one half as potent as the highly stereoisomerically pure amine (compound 29, 95:5, trans:cis).

A number of the compounds identified as active inhibitors against CYP2A6-mediated hydroxylation of coumarin were also examined as inhibitors of oxidation of nicotine (Table 2). In good agreement with the coumarin hydroxylase inhibition studies, the trans amine (compound 29) was significantly more potent an inhibitor of CYP2A6 than was the racemic amine (compound 38). Interestingly, the ethyl derivative (compound 44) was quite potent an inhibitor of microsomal nicotine oxidase.

Acetylcholine Binding Protein

The compounds were also tested for their ability to quench the intrinsic fluorescence of the AchBP. This provided information about the binding efficacy towards the α7 nicotinic acetylcoline receptor. Compounds 8, 17, 29, 33 and 38 showed modest binding avidity to the AchBP while compounds 27 and 55 were very potent. However, compounds 14, 44, and 69 were non-binders of the AchBP.

Summary for Examples 1-9

An efficient method for synthesizing tetrahydrofuran, heteroaryl and carbocyclic analogs of nicotine was accomplished. The design of the molecules was to incorporate functional groups into the molecules that would ligate to the prosthetic heme iron of CYP2A6- the enzyme that predominantly oxidizes nicotine. The synthetic compounds were evaluated as inhibitors of coumarin 7-hydroxylase activity using a fluorescence assay. Compounds with significant activity were next evaluated for inhibition of nicotine oxidase activity, testosterone 6β-hydroxylase activity. Thiophene, furan and alkyne analogs of nicotine containing nucleophilic side chains showed the greatest degree of inhibition of CYP2A6. Heteroaryl analogues of nicotine show a wide range of inhibition of CYP2A6 and a number of analogs were found to be a highly potent and selective inhibitor of CYP2A6. Highly active compounds were also studied for binding to fresh water snail acetylcholine binding protein: a high-throughput model system for mammalian nicotinic receptors. Compounds 27 and 55 showed the greatest affinity for the protein.

The approach has lead to active compounds with promising pharmacological properties that could lead to a new class of smoking cessation agents and lung cancer inhibitors.

Example 10

Preclinical Evaluation of Synthetic Inhibitors of Cytochrome P-450 2A6

(Note: CYP2A6 and CYP3A4 IC$_{50}$ data for several compounds as described in the following example are also listed in Table 1, supra.)

Materials and Methods

Materials.

The synthesis of test compounds 1a-1c, 2a-2c, 3a-3c, and 4-11 are described in Denton et al., *J. Med. Chem*. P-450 2A6 (in press). Commercially available reagents were purchased from Aldrich chemical company or VWR and were used as received. All moisture sensitive reactions were carried out in flame-dried glassware under an argon atmosphere. Tetrahydrofuran (THF) and toluene were freshly distilled from calcium hydride under an argon atmosphere. Methanol (CH$_3$OH) was passed through a column of neutral alumina and stored over 3 Å molecular sieves prior to use. Melting points were determined on a Mettler-Toledo FP62 melting point instrument and are uncorrected. Analytical thin-layer chromatography (TLC) was done on K6F silica gel 60 Å (Whatman) glass-backed plates. Compounds were detected using UV absorption at 254 nm and/or stained with I$_2$ (iodine). Flash chromatography was performed on Merck (60 Å)

pore silica. NMR spectra were recorded at 300 MHz on a Varian mercury spectrometer. Chemical shifts are reported in parts per million (ppm, δ) using residual solvent signals as internal standards. Mass spectroscopy was done using electrospray ionization (ESI) on a Hitachi M-8000 3DQMS (ion trap) mass spectrometer. UV spectral data was acquired on a Varian Cary 1E UV-Vis spectrophotometer.

Microsomes from human lymphoblast cells expressing human cytochrome P-450 2A6 and human liver microsomes (CYP3A4) were purchased from BD Gentest (Woburn, Mass.) and microsomes from baculovirus-infected cells co-expressing cytochrome P-405s (2E1, 2B6, 2C9, 2C19 and 2D6), NADPH-cytochrome P-450 reductase and cytochrome $b_5$ (BACULOSOMES®) were purchased from PanVera LLC (Madison, Wis.).

S-(5-(pyridin-3-yl)furan-2-yl)methyl ethanethioate (13)

Figure 7:
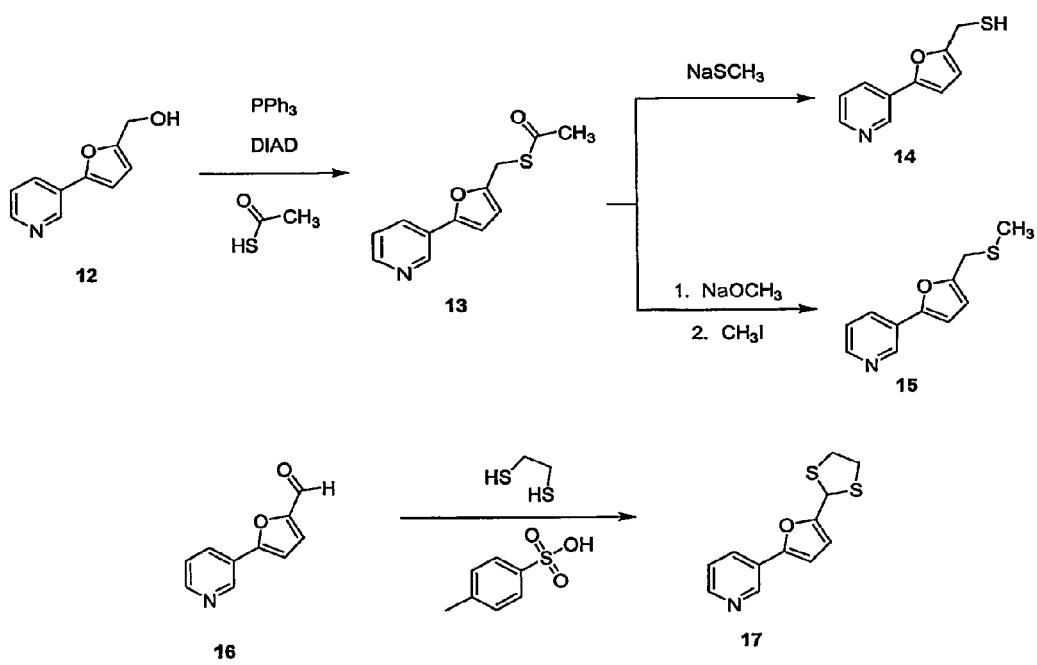
FIG. 7 depicts the synthesis of compounds 13-15 and 17 of Example 10.

(See FIG. 7.) To a solution of alcohol 12 (Denton et al., supra) (121 mg, 0.69 mmol) in $CH_2Cl_2$ (5 mL) at 0° C. under an argon atmosphere was added phosphorus tribromide (0.032 mL, 0.34 mmol) dropwise over 10 min, the ice bath was removed, the resultant solution was stirred at ambient temperature for 24 h, heated to reflux and stirred for 1.5 h. The solution was cooled to room temperature, diluted with $CH_2Cl_2$ (50 mL), washed with aqueous sodium bicarbonate (50:50, satd. soln./water, v:v, 3×10 mL), dried ($Na_2SO_4$) filtered and the solvent was removed in vacuo. The residue was taken up in DMF (5 mL), treated with potassium thioacetate (95 mg, 0.83 mmol) heated to 100° C. and stirred overnight. The solution was cooled to room temperature, poured into aqueous sodium bicarbonate (50:50, satd. soln./water, v:v, 30 mL), extracted with EtOAc (3×30 mL), back washed with aqueous sodium bicarbonate (50:50, satd. soln./water, v:v, 2×20 mL), brine (1×20 mL), dried ($Na_2SO_4$), filtered and the solvent was removed in vacuo. The crude material was chromatographed on silica gel (EtOAc/Hex, 25/75, $R_f$=0.18) to afford the title compound 13 (43 mg, 27% yield) as a yellow semisolid: $^1H$ NMR ($CD_3OD$) δ 8.87 (br s, 1H), 8.48 (br s, 1H), 7.89 (m, 1H), 7.30 (m, 1H), 6.64 (d, J=3.3 Hz, 1H), 6.34 (d, J=3.0 Hz, 1H), 4.20 (s, 2H), 2.37 (s, 3H); LRMS (ESI) m/z calcd for $C_{12}H_{12}NO_2S$ $[M+H]^+$ 234. found 234.

(5-Pyridin-3-yl-furan-2-yl)-methanethiol (14)

(See FIG. 7.) To a solution of 13 (10 mg, 0.05 mmol) in $CHCl_3/CH_3OH$ (1.5 mL, 2:1, v:v) was added sodium thiomethoxide (3 mg, 0.05 mmol) and the resultant solution was stirred under argon for 10 min. The solvent was removed with a stream of argon and the residue was applied directly to a TLC plate (20×20 cm, 250 μm silica gel), developed (EtOAc/Hex, 5/95, $R_f$=0.12), the product band was scraped, extracted with dichloromethane and the solvent was removed in vacuo to afford the title compound 14 (6 mg, 68% yield) as a white film: $^1H$ NMR ($CD_3OD$) δ 8.72 (m, 1H), 8.19 (m, 1H), 7.96 (m, 1H), 7.28 (m, 1H), 6.66 (d, J=3.3 Hz, 1H), 6.07 (d, J=3.3 Hz, 1H), 3.59 (s, 2H), LRMS (ESI) m/z calcd for $C_{10}H_{10}NOS$ $[M+H]^+$ 192. found 192.

3-(5-((methylthio)methyl)furan-2-yl)pyridine (15)

(See FIG. 7.) To a solution of 13 (27 mg, 0.12 mmol) in anhydrous $CH_3OH$ (3 mL) at 0° C. under argon was added a solution of sodium methoxide (15 mg, 0.28 mmol) in anhydrous $CH_3OH$ (1 mL) dropwise, over 10 min and the resultant solution was stirred for 30 min. To the solution was added methyl iodide (17 μL, 0.28 mmol) in anhydrous $CH_3OH$ (1 mL) dropwise over 1 min and the resultant solution was stirred for 30 min. The reaction was stopped by the addition of aqueous sodium bicarbonate (satd. soln., 10 mL). The $CH_3OH$ was removed in vacuo and the aqueous fraction was extracted with EtOAc (3×10 mL). The combined organic fractions were dried ($Na_2SO_4$), filtered and the solvent was removed in vacuo. The crude material was chromatographed on silica gel (EtOAc/Hex, 25/75, $R_f$=0.2) to afford the title compound 15 (13 mg, 54% yield) as an off white solid: mp=67-68° C.; $^1H$ NMR ($CDCl_3$) δ 8.90 (br s, 1H), 8.46 (m, 1H), 7.90 (m, 1H), 7.29 (m, 1H), 6.66 (d, J=3.3 Hz, 1H), 6.29 (d, J=3.3 Hz, 1H), 3.74 (s, 2H), 2.14 (s, 3H); LRMS (ESI) m/z calcd for $C_{11}H_{12}NOS$ $[M+H]^+$ 206. found 206.

3-(5-[1,3]-Dithiolan-2-yl-furan-2-yl)-pyridine (17)

(See FIG. 7.) To a solution of aldehyde 16 (Denton et al., supra) (44 mg, 0.25 mmol) in anhydrous toluene (5 mL) was added ethane dithiol (21 μL, 0.25 mmol) followed by toluene sulfonic acid (small spatula tip, ca. 2 mg), 4 Å molecular seives and the resultant solution was stirred under nitrogen overnight. An additional 5 mg of toluene sulfonic acid was added and the solution was stirred under argon for 2 h. The toluene was decanted and the residue was rinsed with hexanes. The residue was partitioned between EtOAc (20 mL) and aqueous sodium bicarbonate (satd. soln., 20 mL). The organic fraction was collected and the aqueous fraction was extracted with EtOAc (2×20 mL). The combined organic fractions were dried ($Na_2SO_4$), filtered and the solvent was removed in vacuo. The crude material was chromatographed on silica gel (EtOAc/Hex, 50/50, $R_f$=0.3) to afford the title compound 17 (10 mg, 83% yield) as a yellow film: $^1H$ NMR ($CDCl_3$) δ 8.88 (m, 1H), 8.47 (m, 1H), 8.89 (m, 1H), 7.28 (m, 1H), 6.63 (m, 1H), 6.41 (m, 1H), 5.65 (s, 1H), 3.50-3.30 (m, 4H); LRMS (ESI) m/z calcd for $C_{12}H_{12}NOS_2$ $[M+H]^+$ 250. found 250.

General Procedure for Suzuki Coupling Reactions.

To a glass vial containing a magnetic stir bar was added the heteroarylbromide (1.30 mmol) and the vial was purged with argon. To the vial was added a solution of tetrakis(triphenylphosphine)palladium(0) (0.03 mmol) in dimethoxyethane (2 mL), sodium carbonate$_{(aq)}$ (2 M, 1.3 mL, 2.6 mmol) and the vial was once again purged with argon. The resultant solution was stirred at room temperature for 5 min when a solution of phenylboronic acid (198 mg, 1.625 mmol) in ethanol (2 mL) was added, the vial was purged with argon, capped, heated to 90° C. and stirred for 1 h. The solution was cooled to room temperature and filtered through a pad of celite (washing with dichloromethane) into a flask containing anhydrous magnesium sulfate (5 g). The solution was dried for 10 min, filtered through filter paper and the solvent was removed in vacuo to afford the crude product which was chromatographed on silica gel.

5-phenylfuran-2-carbaldehyde (18)

Figure 8:
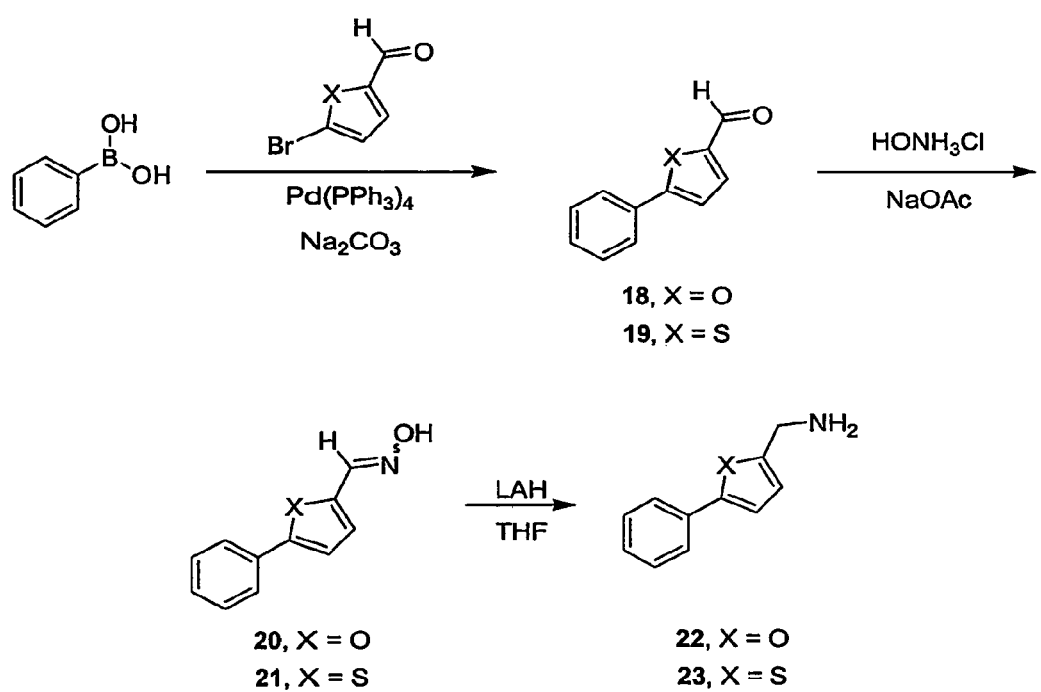
FIG. 8 depicts the synthesis of compounds 18-23 of Example 10.

(See FIG. 8.) The general Suzuki coupling procedure was followed. The crude material was chromatographed on silica gel (EtOAc/Hex, 10/90, $R_f$=0.21) to afford the title compound 18 (201 mg, 90% yield) as an orange oil: $^1H$ NMR ($CDCl_3$) δ 9.59 (s, 1H), 7.75 (m, 2H), 7.36 (m, 3H), 7.26 (d, J=3.9 Hz, 1H), 6.78 (d, J=3.6 Hz, 1H); LRMS (ESI) m/z calcd for $C_{11}H_9O_2$ $[M+H]^+$ 173. found 173.

Cis/trans 5-phenylfuran-2-carbaldehyde oximes (20)

(See FIG. 8.) To a solution of 18 (220 mg, 1.28 mmol) in 95% ethanol (6 mL) was added hydroxylamine hydrochloride (107 mg, 1.53 mmol), sodium acetate (126 mg, 1.53 mmol) and the resultant slurry was heated to reflux and stirred for 25 min. The slurry was diluted with EtOAc (20 mL), washed with water (3×20 mL), dried ($Na_2SO_4$), filtered and the solvent was removed in vacuo to afford the cis/trans mixture of the title compound 20 (228 mg, 95% yield) as a yellow semi-solid which was used in further reactions without further purification: $^1$H NMR ($CD_3OD$) δ 7.99 (s, 1.3H), 7.76-7.71 (m, 5H), 7.48 (s, 0.7H), 7.42-7.24 (m, 7H), 6.89-6.71 (m, 41-1); LRMS (ESI) m/z calcd for $C_{11}H_{10}NO_2$ $[M+H]^+$ 188. found 188.

(5-phenylfuran-2-yl)methanamine (22)

(See FIG. 8.) To a solution of 20 (95 mg, 0.51 mmol) in THF (5 mL) was added a solution of lithium aluminum hydride (1.0 M, 0.63 mL, 0.63 mmol) dropwise and the resultant solution was stirred at room temperature for 24 h. The reaction was poured into MeOH (20 mL), diluted with water (50 mL) and extracted with $CHCl_3$/IPA (3:1, 50 mL, 2×20 mL), dried ($Na_2SO_4$), filtered and the solvent was removed in vacuo to afford the title compound 22 (46 mg, 52% yield) as a colorless oil that rapidly decomposes. 35 mg was dissolved in $Et_2O$ (2 mL) and treated with etherial HCl (1 mL). The solid was collected by filtration to afford the hydrochloride salt of 22 (12 mg) as an off white foam: $^1$H NMR ($D_2O$) δ 7.59 (m, 2H), 7.29 (m, 2H), 7.19 (m, 1H), 6.64 (d, J=3.3, 1H), 6.45 (d, J=3.6, 1H), 4.09 (s, 2H); LRMS (ESI) m/z calcd for $C_{11}H_9O$ $[M-NH_2]^+$ 157. found 157.

5-phenylthiophene-2-carbaldehyde (19)

(See FIG. 8.) The general Suzuki coupling procedure was followed in two reaction vessels. The crude material from both vessels was combined and chromatographed on silica gel (EtOAc/Hex, 10/90, $R_f$=0.16) to afford the title compound 19 (410 mg, 84% yield) as yellow solid: mp=92-93° C.; $^1$H NMR ($CDCl_3$) δ 9.88 (s, 1H), 7.74 (d, J=3.8 Hz, 1H), 7.68-7.65 (m, 2H), 7.46-7.39 (m containing a doublet, J=3.9 Hz, 4H); LRMS (ESI) m/z calcd for $C_{11}H_9OS$ $[M+H]^+$ 189. found 189.

Cis/trans 5-phenylthiophene-2-carbaldehyde oximes (21)

(See FIG. 8.) To a solution of 19 (193 mg, 1.03 mmol) in 95% ethanol (5 mL) was added hydroxylamine hydrochloride (86 mg, 1.23 mmol), sodium acetate (100 mg, 1.23 mmol) and the resultant slurry was heated to reflux and stirred for 25 min. The slurry was poured into water (25 mL) and extracted with EtOAc (3×25 mL), dried ($Na_2SO_4$), filtered and the solvent was removed in vacuo to afford the cis/trans mixture of the title compound 21 (228 mg, 95% yield) as a yellow solid which was used in further reactions without further purification: mp=136-138° C.; $^1$H NMR ($CDCl_3$) δ 8.27 (s, 1H), 7.72 (s, 1H), 7.68-7.60 (m, 5H), 7.40-7.29 (m, 9H) 7.24 (d, J=3.8 Hz, 1H), 7.16 (d, J=3.8 Hz, 1H); LRMS (ESI) m/z calcd for $C_{11}H_{10}NO_2$ $[M+H]^+$ 204. found 204.

(5-phenylthiophen-2-yl)methanamine (23)

(See FIG. 8.) To a solution of 21 (150 mg, 0.74 mmol) in THF (5 mL) was added a solution of lithium aluminum hydride (1.0 M, 0.92 mL, 0.92 mmol) dropwise and the resultant solution was stirred at room temperature for 24 h. The reaction was poured into MeOH (20 mL), diluted with water (50 mL) and extracted with $CHCl_3$/IPA (3:1, 50 mL, 2×20 mL), dried ($Na_2SO_4$), filtered and the solvent was removed in vacuo. The crude material was chromatographed on silica gel (preparative TLC, $CH_3OH$/$CHCl_3$, 10/90, $R_f$=0.18) to afford the title compound 23 (11 mg, 8% yield) as a white film: $^1$H NMR ($CDCl_3$) δ 7.58-7.55 (m, 2H), 7.38-7.33 (m, 2H), 7.28-7.23 (m, 1H), 7.14 (d, J=3.6, 1H), 6.87 (d, J=3.6, 1H), 4.05 (s, 2H); LRMS (ESI) m/z calcd for $C_{11}H_9S$ $[M-NH_2]^+$ 173. found 173.

3-methyl-4-phenylthiophene (24)

Figure 9:
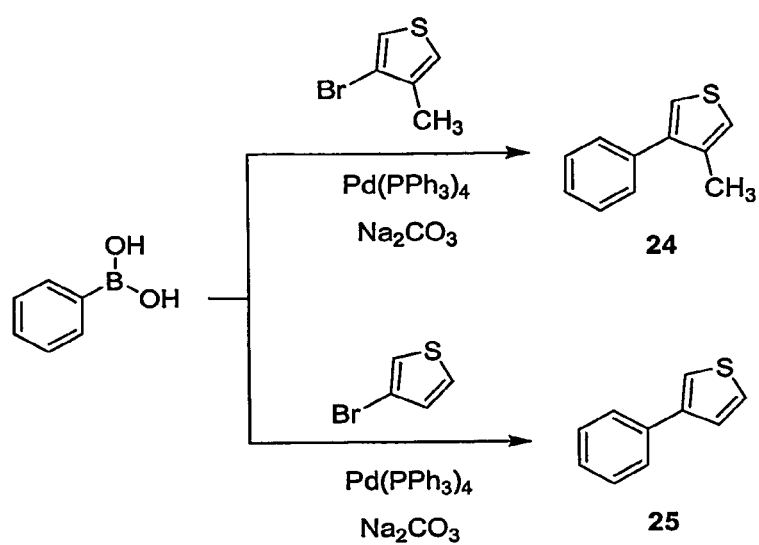
FIG. 9 depicts the synthesis of compounds 24 and 25 of Example 10.

(See FIG. 9.) The general Suzuki coupling procedure was followed. The crude material was chromatographed on silica gel (Hex, $R_f$=0.4) to afford the title compound 24 (203 mg, 90% yield) as a colorless oil: 1H NMR ($CDCl_3$) δ 7.46-7.35 (m, 5H), 7.23 (d, J=3.3 Hz, 1H), 7.06 (m, 1H), 2.32 (s, 3H).

3-phenylthiophene (25)

(See FIG. 9.) The general Suzuki coupling procedure was followed. The crude material was chromatographed on silica gel (Hex, $R_f$=0.44) to afford the title compound 25 (183 mg, 90% yield) as a white solid. The analytical data is consistent with previously published values (Rieke et al., *J. Org. Chem.* 62:6921-6927 (1997).

3-(4-methylthiazol-2-yl)pyridine (26)

Figure 10:
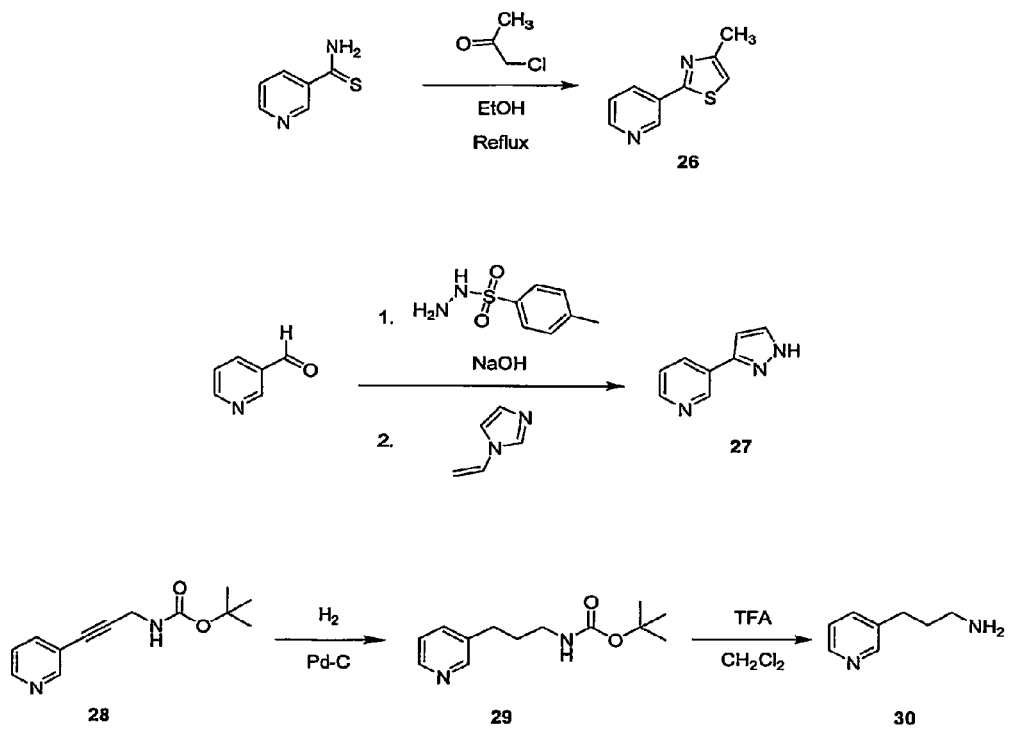
FIG. 10 depicts the synthesis of compounds 26, 27, 29, and 30 of Example 10.

(See FIG. 10.) To a solution/slurry of thionicotinamide (3.3 g, 23.9 mmol) in ethanol (100 mL) is added chloroacetone (2.28 mL, 28.7 mmol) and the resultant slurry is heated to reflux and stirred for 48 h. The solvent was removed in vacuo and the crude material was chromatographed on silica gel (EtOAc/Hex, 50/50, $R_f$=0.34) to afford the title compound 26 (543 mg, 13% yield) as a brown solid: mp=42-43° C.; $^1$H NMR ($CDCl_3$) δ 9.09 (m, 1H), 8.57 (m, 1H), 8.15 (m, 1H), 7.31 (m, 1H), 6.89 (m, 1H), 2.47 (s, 3E1); LRMS (ESI) calcd for $C_9H_8N_2S$ $[M+H]^+$ 177. found 177.

3-(1H-Pyrazol-3-yl)pyridine (27)

(See FIG. 10.) To a solution of nicotinaldehyde (2.0 mL, 21.2 mmol) in 95% EtOH (20 mL) was added 2-tosylhydrazine (3.95 g, 21.2 mmol) and the resultant solution was stirred at room temperature for 2 h. To the solution was added aqueous sodium hydroxide (5 N, 4.2 mL, 21.2 mmol) and the solution was stirred for twenty minutes. To the solution was added 1-vinylimidazole (9.6 mL, 106 mmol) and the resultant solution was warmed to 50° C. and stirred under an argon atmosphere for 96 h. The solution was poured into a water/EtOAc mixture (1:1, 100 mL), the organic fraction was collected and the aqueous fraction was extracted with EtOAc (2×50 mL). The combined organic fractions were dried ($Na_2SO_4$), filtered and the solvent was removed in vacuo. The crude material was chromatographed on silica gel (EtOAc/Hex, 50/50, $R_f$=0.08) to afford the title compound 27 (1.73 g, 56% yield) as a pale white oil: $^1$H NMR ($CDCl_3$) δ 9.03 (m, 1H), 8.52 (m, 1H), 8.06 (m, 1H), 7.59 (d, J=2.2 Hz, 1H), 7.29 (m, 1H); 6.61 (d, J=2.5 Hz, 1H); LRMS (ESI) m/z calcd for $C_8H_8N_3$ $[M+H]^+$ 146. found 146.

tert-Butyl 3-(pyridin-3-yl)propylcarbamate (29)

(See FIG. 10.) To a solution of acetylene 28 (255 mg, 1.2 mmol) (Denton et al., *J. Med. Chem.* P-450 2A6 (in press)) in $CH_3OH$ (20 mL) was added a slurry of 10% Pd/C (60 mg) in $CH_3OH$ (5 mL). The resultant solution was degassed and purged with hydrogen three times and then hydrogenated under double balloon pressure for 24 h. The catalyst was removed by filtration through a pad of celite, the solvent was removed in vacuo EtOAc/Hex, 50/50, $R_f$=0.16) to afford the title compound 29 (249 mg, 97% yield) as a pale yellow oil: $^1$H NMR (CDCl$_3$) δ 8.31 (m, 2H), 7.41 (m, 1H), 7.10 (m, 1H), 5.08 (br s, 1H), 3.04 (br q, J=12.9, 6.6 Hz, 2H), 2.53 (t, J=7.8 Hz, 2H), 6.18 (heptet, J=15.1, 7.4 Hz, 2H), 1.33 (s, 9H); LRMS (ESI) m/z calcd for C$_{13}$H$_{21}$N$_2$O$_2$ [M+H]$^+$ 237. found 237.

3-(pyridin-3-yl)propan-1-amine (30)

(See FIG. 10.) To a solution of 29 (249 mg, 1.05 mmol) in CH$_2$Cl$_2$ (3 mL) at 0° C. was added TFA (2 mL, excess), the ice bath was removed and the resultant solution was stirred at ambient temperature for 1 h. The solvent and excess TFA were removed with a stream of nitrogen and the residue was partitioned between HCl$_{(aq)}$ (1.0 M, 2 mL) and EtOAc (10 mL). The aqueous fraction was collected and subsequently washed with EtOAc (2×10 mL). To the remaining aqueous fraction was added CH$_2$Cl$_2$ (20 mL) and water (20 mL) and the pH was adjusted to 10 with NaOH$_{(aq)}$ (10 N) while stirring. The organic fraction was collected and the remaining aqueous fraction was extracted with CH$_2$Cl$_2$ (2×15 mL). The combined organic fractions were dried (Na$_2$SO$_4$), filtered and the solvent was removed in vacuo to afford the title compound 30 (97 mg, 68% yield) as a yellow oil: $^1$H NMR (CDCl$_3$) δ 8.35 (m, 2H), 7.42 (m, 1H), 7.12 (m, 1H), 2.67-2.54 (m, 4H), 1.73-1.63 (m, 4H); LRMS (ESI) m/z calcd for C$_8$H$_{13}$N$_2$ [M+H]$^+$ 137. found 137.

tert-Butyl (3-(pyridin-3-yl)-1H-pyrazol-5-yl)methylcarbamate (31)

Figure 11:
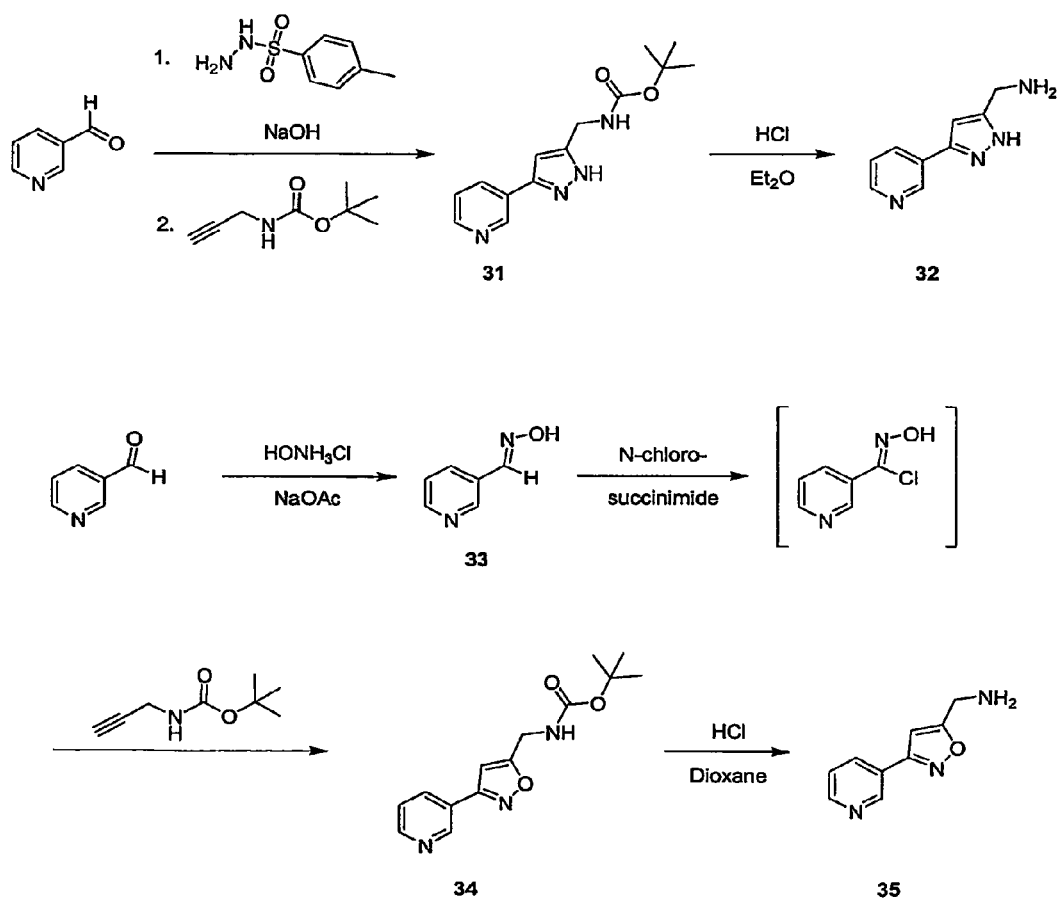
FIG. 11 depicts the synthesis of compounds 31-35 of Example 10.
Figure 12:
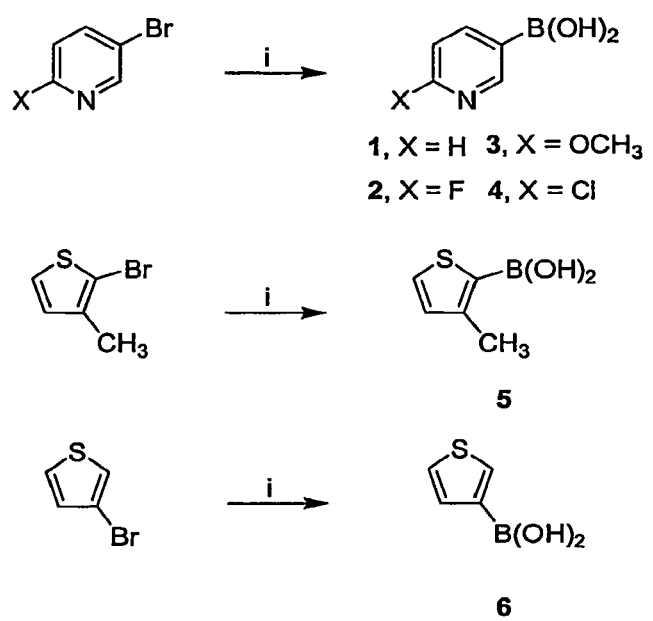
FIG. 12 depicts the synthesis of compounds 1-6 of Example 13. $^a$Reagents: (i) nBuLi, B(OiPr)$_3$, HCl(aq), NaOH (aq).
Figure 13:
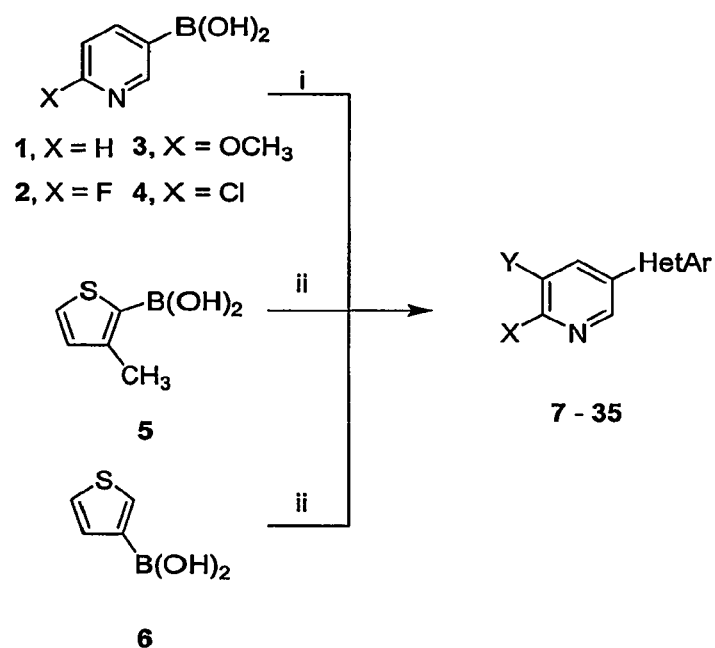
FIG. 13 depicts the synthesis of compounds 7-35 of Example 13. $^a$Reagents: (i) HetAr-bromide, Pd(PPh$_3$)$_4$, Na$_2$CO$_3$, DME, 90° C. 3,5-dibromopyridine, Pd(PPh$_3$)$_4$, Na$_2$CO$_3$, DME, 90° C.
Figure 14:
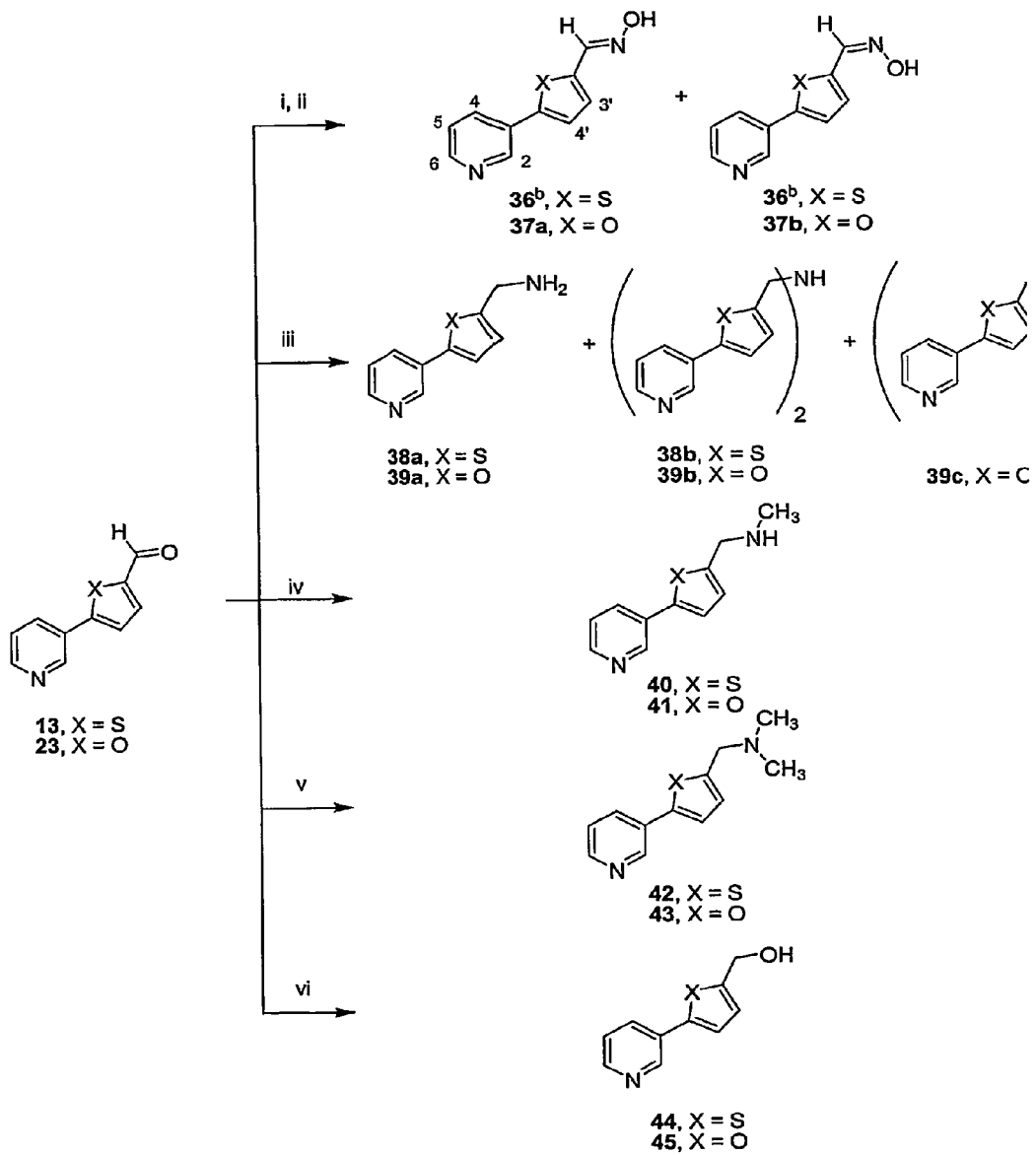
FIG. 14 depicts the synthesis of compounds 36, 37a, 37b, 38a, 38b, 39a, 39b, 39c, and 40-45 of Example 13. $^a$Reagents: (i) HO—NH$_2$.HCl, NaOAc, CH$_3$CH$_2$OH, heat. (ii) chromatographic separation. (iii) NH$_4$OAc, NaBH$_3$CN, CH$_3$OH. (iv) CH$_3$NH$_2$, NaBH$_3$CN, CH$_3$OH. (v) (CH$_3$)$_2$NH, NaBH$_3$CN, CH$_3$OH. (vi) NaBH$_4$, CH$_3$OH. $^b$Chromatographic separation of the cis/trans isomers was not achieved.
Figure 15:
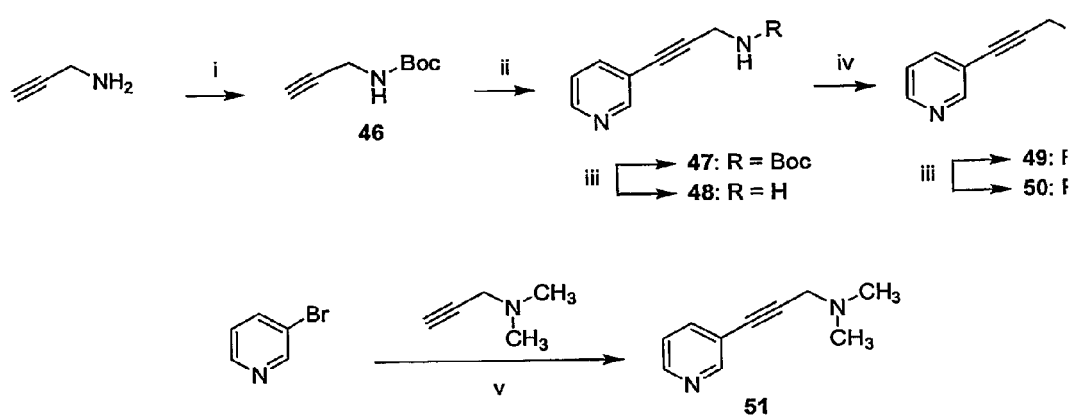
FIG. 15 depicts the synthesis of compounds 46-51 of Example 13. $^a$Reagents: (i) Boc$_2$O, TEA, CH$_2$Cl$_2$. 3-bromopyridine, Pd(PPh$_3$)$_4$, CuI, Na$_2$CO$_3$, DME, 90° C. (iii) TFA, CH$_2$Cl$_2$. (iv) NaH, THF, CH$_3$I. (v) Pd(PPh$_3$)$_4$, CuI, Na$_2$CO$_3$, DME, 90° C.
Figure 16:
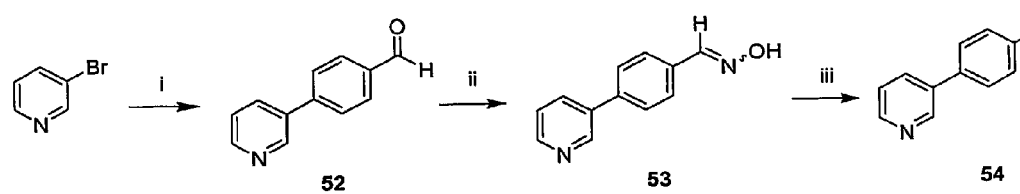
FIG. 16 depicts the synthesis of compounds 52-54 of Example 13. $^a$Reagents: (i) 4-bromobenzaldehyde, Pd(PPh$_3$)$_4$, Na$_2$CO$_3$, DME, 90° C. (ii) HO—NH$_2$.HCl, NaOAc, CH$_3$CH$_2$OH, heat. (iii) LAH, THF.
Figure 17:
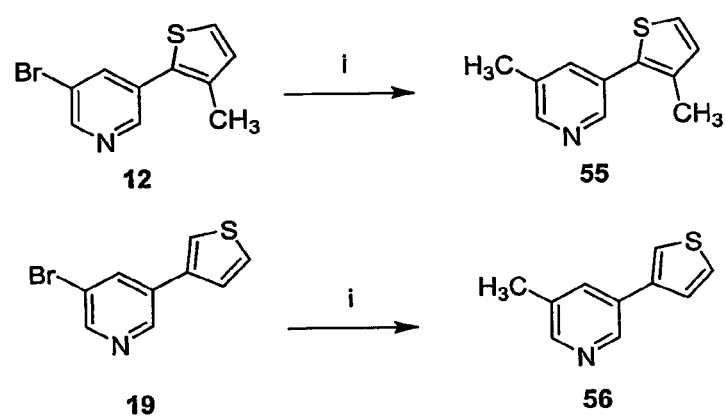
FIG. 17 depicts the synthesis of compounds 55 and 56 of Example 13. $^a$Reagents: (i) (CH$_3$)$_4$Sn, Pd(PPh$_3$)$_4$, Na$_2$CO$_3$, DME, 90° C.
Figure 18:
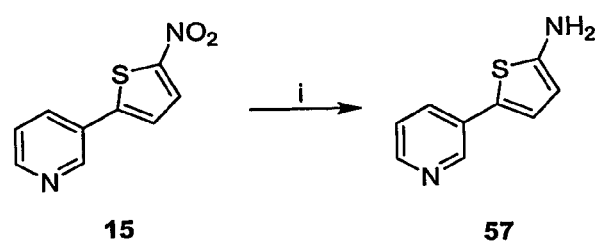
FIG. 18 depicts the synthesis of compound 57 of Example 13. $^a$Reagents: (i) H$_2$, 10% Pd—C, CH$_3$OH.
Figure 19:
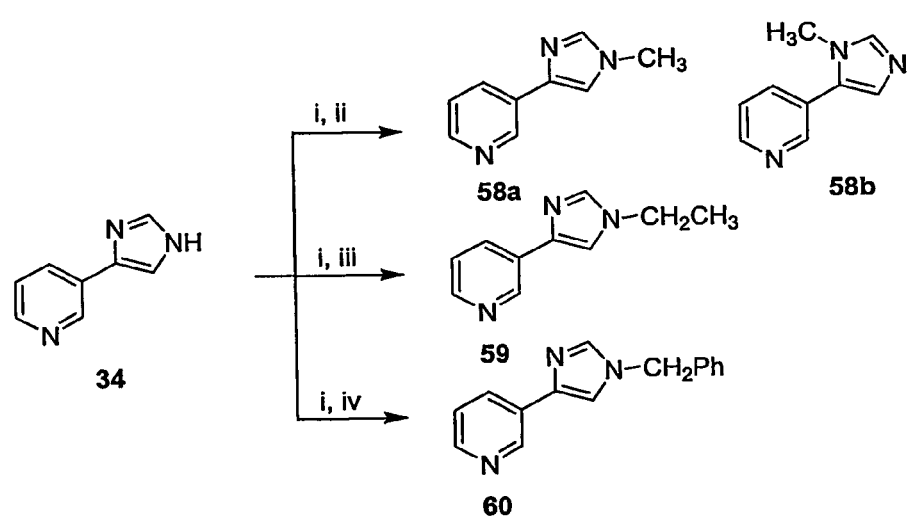
FIG. 19 depicts the synthesis of compounds 58a, 58b, 59, and 60 of Example 13. $^a$Reagents: (i) NaH, THF. (ii) CH$_3$I. CH$_3$CH$_2$I. (iv) PhCH$_2$Br.
Figure 20:
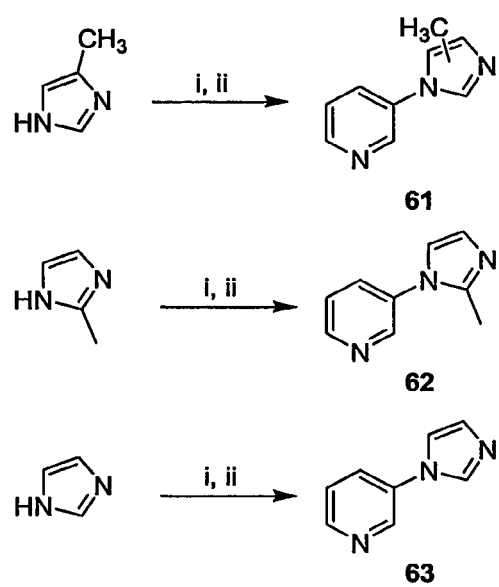
FIG. 20 depicts the synthesis of compounds 61-63 of Example 13. $^a$Reagents: (i) NaH, DMF. 3-fluoropyridine.
Figure 21:
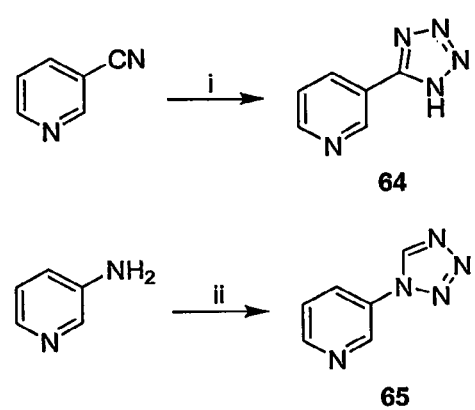
FIG. 21 depicts the synthesis of compounds 64 and 65 of Example 13. $^a$Reagents: (i) NaN$_3$, NH$_4$Cl, DMF. (ii) trimethyl orthoformate, NaN$_3$, HOAc.

(See FIG. 11.) To a solution of nicotinaldehyde (150 μL, 1.59 mmol) in 95% EtOH (5 mL) was added 2-tosylhydrazine (296 mg, 1.59 mmol) and the resultant solution was stirred at room temperature for 2 h. To the solution was added aqueous sodium hydroxide (5 N, 0.32 mL, 1.59 mmol) and the solution was stirred for 20 min. To the solution was added a solution of tert-butyl prop-2-ynylcarbamate (1.23 g, 7.95 mmol) and the resultant solution was warmed to 50° C. and stirred under an argon atmosphere for 96 h. The solution was poured into a water/EtOAc mixture (1:1, 100 mL), the organic fraction was collected and the aqueous fraction was extracted with EtOAc (2×20 mL). The combined organic fractions were dried (Na$_2$SO$_4$), filtered and the solvent was removed in vacuo. The crude material was chromatographed on silica gel (EtOAc/Hex, 50/50, $R_f$=0.08) to afford the title compound 31 (158 mg, 36% yield) as a white solid: mp=185-187° C.; $^1$H NMR. (CDCl$_3$) δ 8.92 (m, 1H), 8.50 (m, 1H), 8.01 (m, 1H), 7.28 (m, 1H), 6.47 (s, 1H); 5.62 (br s, 1H); 4.34 (d, J=6 Hz, 1H), 1.45 (s, 9H); LRMS (ESI) m/z calcd for C$_{14}$H$_{19}$N$_4$O$_2$ [M+H]$^+$ 275. found 275.

(3-(pyridine-3-yl)-1H-pyrazol-5-yl)methanamine (32)

(See FIG. 11.) To a solution of 31 (40 mg, 0.11 mmol) in CH$_2$Cl$_2$ (1 mL) at 0° C. was added TFA (1 mL, excess) and the resultant solution was stirred for 30 min. The solvent and excess TFA were removed under a stream of nitrogen and the residue was partitioned between HCl$_{(aq)}$ (1.0 M, 1 mL) and Et$_2$O (5 mL). The aqueous fraction was collected and subsequently washed with Et$_2$O (2×5 mL) To the remaining aqueous fraction was added CHCl$_3$ (10 mL) and water (10 mL) and the pH was adjusted to 10 with NaOH$_{(aq)}$ (10 N) while stirring. The organic fraction was collected and the remaining aqueous fraction was extracted with CHCl$_3$ (2×10 mL). The combined organic fractions were dried (Na$_2$SO$_4$), filtered and the solvent was removed in vacuo to afford the title compound 31 (3.4 mg, 14% yield) as a colorless residue: $^1$H NMR (CDCl$_3$) δ 8.99 (m, 1H), 8.55 (m, 1H), 8.08 (m, 1H), 7.32 (m, 1H), 6.49 (s, 1H), 4.05 (s, 2H); LRMS (ESI) m/z calcd for C$_9$H$_{11}$N$_4$ [M+H]$^+$ 175. found 175.

Nicotinaldehyde oxime (33)

Nicotinaldehyde oxime was prepared in quantitative yield by the reaction of nicotinaldehyde with hydroxylamine and sodium acetate in ethanol as for 20.

tert-Butyl (3-(pyridin-3-yl)isoxazol-5-yl)methylcarbamate (34)

To a solution of 33 (161 mg, 1.3 mmol) in anhydrous DMF (5 mL) at 0° C. was added N-chlorosuccinimide (202 mg, 1.3 mmol) portionwise over 20 min. The resultant solution was heated to 50° C. and stirred for 50 min. The solution was cooled to room temperature and transferred to a flask containing CH$_2$Cl$_2$ (3 mL). To the solution was added a solution of tert-butyl prop-2-ynylcarbamate (204 mg, 1.3 mmol) in CH$_2$Cl$_2$ (3 mL), the solution was cooled to 0° C. and triethylamine (0.18 mL, 1.3 mmol) was added dropwise, the ice bath was removed and the solution was stirred at ambient temperature for 3 h. To the solution was added saturated aqueous sodium bicarbonate (30 mL), the organic fraction was collected and the aqueous fraction was extracted with CH$_2$Cl$_2$ (2×15 mL), back washed with water (30 mL), and brine (30 mL), dried (Na$_2$SO$_4$), filtered and the solvent was removed in vacuo. The crude material was chromatographed on silica gel (EtOAc/Hex, 50/50, $R_f$=0.16) to afford the title compound 34 (212 mg, 59% yield) as a an off white solid: mp=67-69° C.; $^1$H NMR (CDCl$_3$) δ 8.93 (br s, 1H), 8.62 (m, 1H), 8.05 (m, 1H), 7.34 (m, 1H), 6.50 (s, 1H); 5.63 (br s, 1H); 4.43 (d, J=6 Hz, 1H), 1.40 (s, 9H); LRMS (ESI) calcd for C$_{14}$H$_{18}$N$_3$O$_3$ [M+H]$^+$ 276. found 276.

(3-(Pyridin-3-yl)isoxazol-5-yl)methanamine dihydrochloride (35)

To a solution of 34 (67 mg, 0.24 mmol) in 1,4-dioxane (5 mL) at 0° C. was bubbled in HCl$_{(g)}$ until the solution was saturated. The ice bath was removed and the solution was stirred at ambient temperature for 2 h. The solvent and excess HCl were removed with a stream of argon to afford the title compound 35 (45 mg, 88% yield) as a white solid: mp=153-155° C. dec, $^1$H NMR (D$_2$O) δ 9.12 (m, 1H), 8.83 (m, 1H), 8.73 (m, 1H), 8.04 (m, 1H), 7.04 (s, 1H); 4.35 (s, 2H); LRMS (ESI) m/z calcd for C$_9$H$_{10}$N$_3$O [M+H]$^+$ 176. found 176.

CYP Inhibition Assays.

To measure CYP2A6 activity, coumarin 7-hydroxylation was determined as described in Denton et al., supra.

To measure CYP3A4 activity, testosterone 6-hydroxylation was determined as described in Denton et al., supra.

To measure CYP2E1, CYP2B6, CYP2C9, CYP2C19 and CYP2D6 activity, isozyme specific vivid blue substrate O-dealkylation was determined via a modified PanVera Vivid Assay Protocol as described in Denton et al., supra.

Mouse Liver Microsome Stability Assay.

A typical assay mixture contains mouse liver microsomes (0.5 mg of protein), 100 μM potassium phosphate buffer (pH 7.4), 40 µM test compound, an NADPH-generating system consisting of 0.5 mM NADP+, 0.5 mM glucose-6-phosphate, 5 U/mL glucose-6-phosphate dehydrogenase, 1 mg/mL diethylenetriaminepentaacetic acid (DETAPAC) and 7 mM $MgCl_2$ for a final incubation volume of 0.1 mL. Incubations were run for 0, 10, 25, 40 and 60 min with shaking in air at 37° C. and were terminated by the addition of 1 mL $CH_2Cl_2$/2-propanol (3:1, v:v). After centrifugation at 13,000 rpm for 5 min, the organic fraction was collected and the solvent was removed with a stream of argon. The residue was reconstituted in methanol (200 µL), centrifuged at 13,000 rpm for 5 min and the supernatant was analyzed by high-performance liquid chromatography with an Axxi-chrom (straight-phase) silica column (4.6 mm×250 mm, 5 µm) or with a Supelco (reverse-phase) HS F5 pentafluorophenyl column (4.6 mm×250 mm, 5 µm). Standard conditions utilized an isocratic, ternary-solvent system consisting of solvents A (methanol), B (isopropanol) and C ($HClO_4$) set at a flow rate of 1.5 mL/min (straight-phase), or A, D (water) and E ($HCO_2H$) set at a flow rate of 1.0 mL/min (reverse-phase), λ=254 nm with retention times ($t_R$) evaluated in minutes. The specific conditions and retention times of each individual compound are specified in Table 6.

Human Liver Microsome Stability Assay.

A typical assay mixture contains human liver microsomes (0.4 mg of protein), 100 µM potassium phosphate buffer (pH 7.4), 40 µM test compounds, an NADPH-generating system consisting of 0.5 mM NADP+, 0.5 mM glucose-6-phosphate, 5 U/mL glucose-6-phosphate dehydrogenase, 1 mg/mL DETAPAC and 7 mM $MgCl_2$ for a final incubation volume of 0.1 mL. Incubations were run for 0, 10, 25, 40 and 60 min with shaking in air at 37° C. and were terminated by the addition of 1 mL $CH_2Cl_2$/2-propanol (3:1, v:v). After centrifugation at 13,000 rpm for 5 min, the organic fraction was collected and the solvent was removed with a stream of argon. The residue was reconstituted in methanol (200 µL), centrifuged at 13,000 rpm for 5 rain and the supernatant was analyzed by high-performance liquid chromatography as described above.

Time Dependent Inhibition of CYP2A6.

The incubation mixture contained CYP2A6 microsomes (1 pmol protein), an NADPH-generating system consisting of 0.5 mM NADP+, 0.5 mM glucose-6-phosphate, 5 U/mL glucose-6-phosphate dehydrogenase and 1 mg/mL DETAPAC. The preincubation was initiated by the addition of inhibitor for a final concentration series of 0.7×$IC_{50}$, $IC_{50}$, 2×$IC_{50}$ and 10×$IC_{50}$ for a final incubation volume of 10 µL. After 3, 6, 9, 12, 15 and 20 min the reactions were stopped by transferring the tube to a dry ice/isopropanol bath. The incubation was initiated by the addition of a pre-mixed solution (190 µL) containing coumarin (3 µM), 0.1 M Tris buffer (pH 7.5), and the NADPH-generating system as described above, for a final incubation volume of 0.2 mL. After a 15 min incubation at 37° C., the reactions were stopped by the addition of 0.75 mL of $CH_3CN$/$CCl_3COOH$ (80:20, v:v). After centrifugation at 14,000 rpm for 5 min, 200 µL of the supernatant was transferred to a Packard OptiPlate™-96 well plate and the formation of the coumarin metabolite, 7-hydroxycoumarin, was determined fluorometrically using a Wallac Victor (Vial et al., Am. J. Med. Sci. 291:130-142 (1986)), 1420 Multilabel Counter (Wallac Software Version 2.00 release 9) at excitation and emission wavelengths of 355 nm and 460 nm, respectively. The inhibitory effect of the nicotine analogues was assessed from the difference between the sample and a corresponding control which was not preincubated with inhibitor.

Protein Expression and Purification.

P450 2A6dH was expressed and purified as previously described for P450 2C5 with minor modifications (see Wester, et al., Methods Enzymol. 357: 73-79 (2002)).

Difference Spectra of Test Compounds.

For the measurement, the sample chamber contained 540 nM P450 2A6dH in 100 µM potassium phosphate buffer (pH 7.4) and the reference chamber contained the buffer A baseline was recorded between 260 and 700 nm. Subsequently, test compound (in 100% ethanol, 10 µM) was added to both the cuvettes. The maximal ethanol concentration used was 2%. The difference spectra were obtained after the system reached equilibrium (3 min). All spectra were recorded at 25° C.

Results

The compounds were initially screened at one concentration (10×$IC_{50}$) to identify potential time dependent inhibitors. Full kinetic analyses were done with a series of 4 concentrations (i.e., 0.7, 1, 2 and 10 times the $IC_{50}$ value) to determine the kinetic parameters for the selected compounds (see protocol, below). Compounds 3 and 9 showed time dependent inhibition of CYP2A6 at the initial 10×$IC_{50}$ concentration and were chosen for full kinetic characterization. Compound 3 was determined to be time dependent with a $k_{inactivation}$ value of 0.02 $min^{-1}$ and a $k_I$ of 0.04 µM. Compound 9 only decreased the catalytic efficiency of CYP2A6 at the highest concentration (i.e., 10×$IC_{50}$ value) and thus, the mechanism of inhibition for 9 at the concentrations studied for CYP2A6 inhibition is truly competitive in nature.

Tables.

TABLE 4

Selective functional inhibition of CYP3A4, 2E1, 2B6, 2C9 and 2C19 by synthetic heteroaromatic nicotine analogues

| | $IC_{50}$ ± SD | | | | | | |
|---|---|---|---|---|---|---|---|
| cpd | 2A6 | 3A4 | 2E1 | 2B6 | 2C9 | 2C19 | 2D6 |
| 1a | 0.17 ± 0.02 | 58.7 ± 15.3 | 40.2 ± 18.1 | 52.2 ± 7.6 | 8.9 ± 1.5 | 2.0 ± 0.22 | 169 ± 17 |
| 1b | 1.1 ± 0.13 | >400[a] | >400[a] | >400[a] | 67.7 ± 3.7 | 59.8 ± 6.5 | 113 ± 19 |
| 1c | 133 ± 21 | 219 ± 23 | >400[a] | >400[a] | 206 ± 23 | 106 ± 18 | 28.7 ± 4.1 |
| 2a | 0.27 ± 0.02 | 47.1 ± 18.1 | 172 ± 52 | 191 ± 24 | 11.7 ± 2.2 | 22.0 ± 1.6v | 11.3 ± 2.6 |
| 2b | 1.6 ± 0.34 | >400[a] | >400[a] | 358 ± 22 | 76.1 ± 9.1 | 30.6 ± 4.1 | 90.6 ± 7.8 |
| 2c | 28.3 ± 18.3 | 294 ± 25 | >400[a] | >400[a] | 222 ± 16 | 157 ± 10 | 253 ± 35 |
| 3a | N/D | N/D | N/D | N/D | N/D | N/D | N/D |
| 3b | N/D | N/D | N/D | N/D | N/D | N/D | N/D |
| 3c | N/D | N/D | N/D | N/D | N/D | N/D | N/D |
| 4 | 0.62 ± 0.1 | 6.0 ± 1.29 | 6.9 ± 2.06 | 3.9 ± 0.8 | 93.1 ± 8.8 | 20.1 ± 2.2 | 95.9 ± 0.99 |
| 5 | 0.75 ± 0.1 | 262 ± 63 | 4.1 ± 0.74 | 146 ± 20 | 79.5 ± 8.9 | 122.1 ± 12.2 | 204 ± 22 |
| 6 | 1.0 ± 0.23 | 109 ± 46 | 57.9 ± 12.5 | >300[a] | >300[a] | >300[a] | 297 ± 31 |
| 7 | 1.29 ± 0.14 | 39.1 ± 12.8 | 368 ± 79 | 11.8 ± 1.7 | >400 | 40.9 ± 2.1 | >400 |

TABLE 4-continued

Selective functional inhibition of CYP3A4, 2E1, 2B6, 2C9 and 2C19 by synthetic heteroaromatic nicotine analogues

| cpd | 2A6 | 3A4 | 2E1 | 2B6 | 2C9 | 2C19 | 2D6 |
|---|---|---|---|---|---|---|---|
| 8 | 1.4 ± 0.23 | 55.9 ± 19.2 | >400[a] | 59.1 ± 3.9 | 96.3 ± 9.5 | 111.2 ± 6 | 248 ± 35v |
| 9 | 1.5 ± 0.35 | 152 ± 70 | 109 ± 11 | >300[a] | >300[a] | >300[a] | >300 |
| 10 | 1.5 ± 0.31 | 140 ± 14 | 25.5 ± 3.9 | 103 ± 9 | 41.8 ± 5.2 | 53.5 ± 4.8 | 200 ± 44 |
| 11 | 1.85 ± 0.5 | <25 | 6.28 ± 1.89 | 6.26 ± 0.65 | 123 ± 11 | 24.9 ± 1.4 | 193 ± 28v |
| 13 | 1.7 ± 0.3 | 2.9 ± 1.65 | 0.44 ± 0.08 | 1.7 ± 0.36 | 5.7 ± 1.13 | 7.9 ± 0.74 | 90.8 ± 17.3 |
| 14 | <1.5[b] | 6.1 ± 4.13[c] | 0.09 ± 0.006 | 2.2 ± 0.49 | 0.73 ± 0.17 | 0.44 ± 0.03 | 1.3 ± 0.2 |
| 15 | 1.6 ± 0.19 | 14.8 ± 2.6 | 1.5 ± 0.21 | 93.8 ± 15.2 | 28.2 ± 6 | 14 ± 1.18 | 129 ± 19 |
| 16 | 27.8 ± 6.6 | 2.2 ± 1.12 | 1.1 ± 0.08 | 10.5 ± 1.44 | 2.6 ± 0.29 | 1.4 ± 0.07 | 76.7 ± 8.4 |
| 22 | 1.2 ± 0.2 | N/D | N/D | N/D | N/D | N/D | N/D |
| 23 | 1.2 ± 0.11 | N/D | N/D | N/D | N/D | N/D | N/D |
| 24 | 6.6 ± 0.66 | N/D | N/D | N/D | N/D | N/D | N/D |
| 25 | 12.4 ± 2 | N/D | N/D | N/D | N/D | N/D | N/D |
| 26 | 8.2 ± 1.51 | N/D | N/D | N/D | N/D | N/D | N/D |
| 27 | 25.6 ± 2.7 | N/D | N/D | N/D | N/D | N/D | N/D |
| 30 | 13.2 ± 1.2 | N/D | N/D | N/D | N/D | N/D | N/D |
| 32 | 0.58 ± 0.08 | N/D | N/D | N/D | N/D | N/D | N/D |
| 35 | 0.74 ± 0.09 | N/D | N/D | N/D | N/D | N/D | N/D |
|  | N/D | N/D | N/D | N/D | N/D | N/D | N/D |
|  | N/D | N/D | N/D | N/D | N/D | N/D | N/D |

[a]No inhibition was seen at the highest concentration tested.
[b]The test compound was highly fluorescent and an accurate value was not determined.
[c]The test compound was highly fluorescent which gave rise to the high standard deviation.

TABLE 5

Selectivity ratio ($IC_{50}$ CYPX/$IC_{50}$ CYP2A6)[a] of heteroaromatic nicotine analogues for human CYPs 3A4, 2E1, 2B6, 2C9 and 2C19 versus human CYP2A6

| cpd | 3A4/2A6 | 2E1/2A6 | 2B6/2A6 | 2C9/2A6 | 2C19/2A6 | 2D6/2A6 |
|---|---|---|---|---|---|---|
| 1a | 345 | 236 | 307 | 52 | 12 | 994 |
| 1b | >364 | >364 | >364 | 62 | 54 | 103 |
| 1c | 1.6 | >3 | >3 | 1.5 | 0.8 | 0.2 |
| 2a | 174 | 637 | 707 | 43 | 81 | 42 |
| 2b | >250 | >250 | 224 | 48 | 19 | 57 |
| 2c | 10 | >14 | N/D | N/D | N/D | N/D |
| 3a | N/D | N/D | N/D | N/D | N/D | N/D |
| 3b | N/D | N/D | N/D | N/D | N/D | N/D |
| 3c | N/D | N/D | N/D | N/D | N/D | N/D |
| 4 | 10 | 11 | 6.3 | 150 | 39 | 155 |
| 5 | 349 | 5 | 195 | 106 | 163 | 272 |
| 6 | 109 | 58 | >300 | >300 | >300 | >300 |
| 7 | 5.9 | 285 | 9.1 | >310 | 32 | >310 |
| 8 | 40 | >286 | 42 | 69 | 81 | >286 |
| 9 | 101 | 73 | >200 | 260 | >200 | >200 |
| 10 | 93 | 17 | 69 | 28 | 35 | 133 |
| 11 | 53 | <14 | 3.4 | 66 | 14 | 104 |
| 13 | 1.7 | 0.3 | 1 | 3.4 | 4.6 | 53 |
| 14 | >4.1 | <0.06 | >1.5 | <0.5 | <0.3 | <0.86 |
| 15 | 9.2 | 0.9 | 59 | 18 | 8.8 | 81 |
| 16 | 0.08 | 0.04 | 0.4 | 0.09 | 0.05 | 2.8 |
| 22 | N/D | N/D | N/D | N/D | N/D | N/D |
| 23 | N/D | N/D | N/D | N/D | N/D | N/D |
| 24 | N/D | N/D | N/D | N/D | N/D | N/D |
| 25 | N/D | N/D | N/D | N/D | N/D | N/D |
| 26 | N/D | N/D | N/D | N/D | N/D | N/D |
| 27 | N/D | N/D | N/D | N/D | N/D | N/D |
| 30 | N/D | N/D | N/D | N/D | N/D | N/D |
| 32 | N/D | N/D | N/D | N/D | N/D | N/D |
| 35 | N/D | N/D | N/D | N/D | N/D | N/D |

TABLE 6

High-preformance liquid chromatography mobile phases and retention times for the heteroaromatic nicotine analogues

| cpd | Mobile Phase[a] | Retention Time (min) |
|---|---|---|
| 1a | 60(A):40(B):0.05(C) | 5.00 |
| 1b | 60(A):40(B):0.05(C) | 7.06 |
| 1c | 60(A):40(B):0.07(C) | 5.85 |
| 2a | 60(A):40(B):0.05(C) | 4.65 |
| 2b | 60(A):40(B):0.05(C) | 6.76 |
| 2c | 60(A):40(B):0.07(C) | 5.48 |
| 3a | 55(A):45(B):0.018(C) | 7.35 |
| 3b | 55(A):45(B):0.018(C) | 9.94 |
| 3c | 55(A):45(B):0.018(C) | 7.66 |
| 4 | 60(A):40(B):0.02(C) | 4.86 |
| 5 | 80(A):20(B):0.1(C) | 3.74 |
| 6 | 60(A):40(B):0.05(C) | 6.06 |
| 7 | 70(D):30(A):0.11(E) | 8.74 |
| 8 | 80(A):20(B):0.05(C) | 5.02 |
| 9 | 80(A):20(B):0.05(C) | 3.93 |
| 10 | 55(A):45(B):0.018(C) | 4.10 |
| 11 | 55(A):45(B):0.018(C) | 5.99 |
| 13 | 60(A):40(B):0.02(C) | 3.84 |
| 14 | 60(A):40(B):0.07(C) | 5.10 |
| 15 | 60(A):40(B):0.02(C) | 3.88 |
| 16 | 60(A):40(B):0.02(C) | 3.91 |
| 22 | N/D | N/D |
| 23 | N/D | N/D |
| 24 | N/D | N/D |
| 25 | N/D | N/D |
| 26 | 55(A):45(B):0.018(C) | 4.54 |
| 27 | 55(A):45(B):0.018(C) | 3.66 |
| 30 | N/D | N/D |
| 32 | 55(A):45(B):0.018(C) | 6.89 |
| 35 | 55(A):45(B):0.018(C) | 7.25 |

[a]HPLC was done with an Axxi-chrom (straight-phase) silica column (4.6 mm × 250 mm, 5 μm) or with a Supelco (reverse-phase) HS F5 pentafluorophenyl column (4.6 mm × 250 mm, 5 μm). Standard conditions utilized an isocratic, ternary-solvent system consisting of solvents A (methanol), B (isopropanol) and C ($HClO_4$) set at a flow rate of 1.5 mL/min (straight-phase), or A, D (water) and E ($HCO_2H$) set at a flow rate of 1.0 mL/min (reverse-phase), λ = 254 nm (See methods section).

TABLE 7

Metabolic stability of heteroaromatic nicotine analogues in the presence human and mouse liver microsomes.

| cpd | HLM t$_{1/2}$ (min) | MLM t$_{1/2}$ (min) |
|---|---|---|
| 1a | 39 | 60 |
| 1b | 96 | Stable[a] |
| 1c | Stable[a] | 343 |
| 2a | 37 | 37 |
| 2b | 66 | Stable[a] |
| 2c | 331 | Stable[a] |
| 3a | Stable[a] | N/D |
| 3b | N/D | N/D |
| 3c | N/D | N/D |
| 4 | 32 | 41 |
| 5 | Stable[a] | 481 |
| 6 | 118 | Stable[a] |
| 7 | 84 | Stable[a] |
| 8 | 271 | Stable[a] |
| 9 | 133 | Stable[a] |
| 10 | 701 | 698 |
| 11 | 429 | 47 |
| 13 | 30 | 18 |
| 14 | 119 | 105 |
| 15 | 59 | 38 |
| 16 | 92 | 24 |
| 22 | N/D | N/D |
| 23 | N/D | N/D |
| 24 | N/D | N/D |
| 25 | N/D | N/D |
| 26 | N/D | N/D |
| 27 | N/D | N/D |
| 30 | N/D | N/D |
| 32 | Stable[a] | N/D |
| 35 | 400 | N/D |

[a]No significant decrease in the area under the curve for the starting material was observed over the course of the assay.

TABLE 8

Spectral interaction analysis of heteroaromatic nicotine analogues with synthetic N-terminal truncated CYP2A6.

| Compd | Structure | binding type | $\lambda_{min}$ | $\lambda_{max}$ |
|---|---|---|---|---|
| 1a | 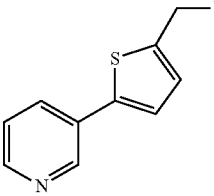 | Type II | 409 nm | 428 nm |
| 1b | 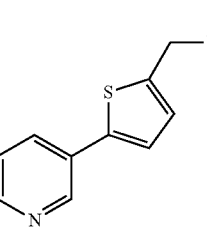 | Type II | 410 nm | 430 nm |
| 1c | 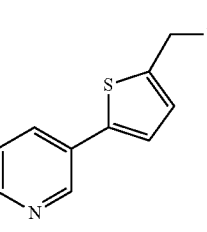 | Type II | 411 nm | 428 nm |
| 2a | 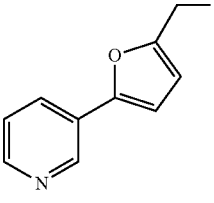 | Type II | 409 nm | 428 nm |

TABLE 8-continued

Spectral interaction analysis of heteroaromatic nicotine analogues with synthetic N-terminal truncated CYP2A6.

| Compd | Structure | binding type | $\lambda_{min}$ | $\lambda_{max}$ |
|---|---|---|---|---|
| 2b | 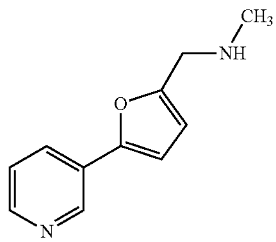 | Type II | 411 nm | 431 nm |
| 2c | 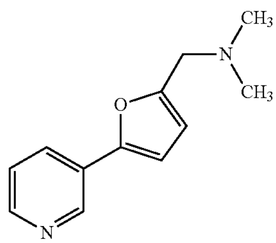 | Type II | 411 nm | 430 nm |
| 3a | 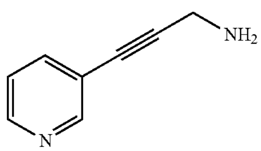 | Type II | 410 nm | 430 nm |
| 3b | 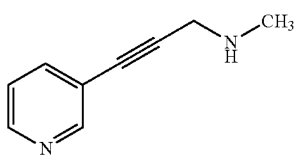 | Type II | 410 nm | 428 nm |
| 3c | 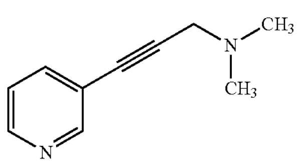 | No Shift[a] | — | — |
| 4 | 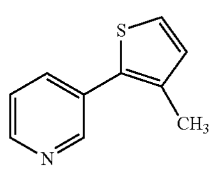 | Type I | 414 nm | 383 nm |
| 5 | 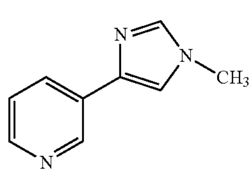 | Type II | 409 nm | 429 nm |
| 6 | 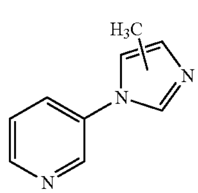 | Type II | 410 nm | 428 nm |

TABLE 8-continued

Spectral interaction analysis of heteroaromatic nicotine analogues with synthetic N-terminal truncated CYP2A6.

| Compd | Structure | binding type | $\lambda_{min}$ | $\lambda_{max}$ |
|---|---|---|---|---|
| 7 | 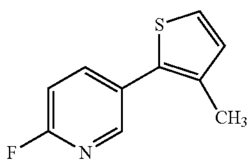 | Type I | 418 nm | 385 nm |
| 8 | 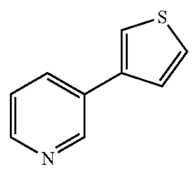 [SMILES: c1cncc(-c2ccsc2)c1] | Type II | 409 nm | 427 nm |
| 9 | 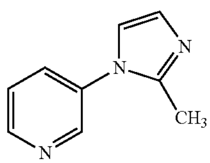 | Type II | 409 nm | 428 nm |
| 10 | 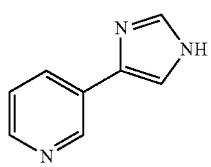 [SMILES: c1cncc(-c2c[nH]cn2)c1] | Type II | 410 nm | 427 nm |
| 11 | 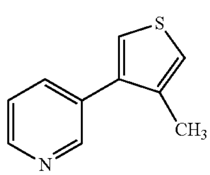 | Type II | 410 nm | 427 nm |
| 13 | 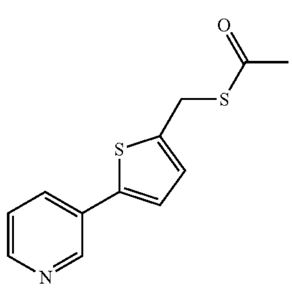 [SMILES: CC(=O)SCc1ccc(-c2cccnc2)s1] | No Shift | Coumarin (−)[b] | Coumarin (−)[b] |
| 14 | 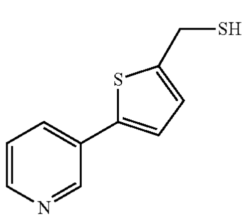 | No Shift | Coumarin (+)[c] | Coumarin (+)[c] |

TABLE 8-continued
Spectral interaction analysis of heteroaromatic nicotine analogues with synthetic N-terminal truncated CYP2A6.
| Compd | Structure | binding type | $\lambda_{min}$ | $\lambda_{max}$ |
|---|---|---|---|---|
| 15 | 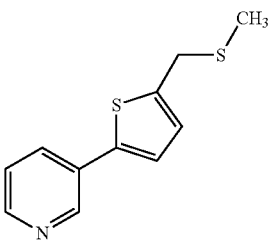 | Type II | 410 nm | 431 nm |
| 16 | 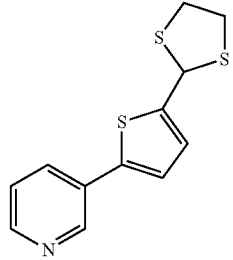 [SMILES: c1cncc(-c2ccc(C3SCCS3)s2)c1] | No Shift | Coumarin (+)[c] | Coumarin (+)[c] |
| 22 | 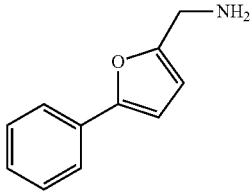 [SMILES: NCc1ccc(-c2ccccc2)o1] | Type II | 410 nm | 430 nm |
| 23 | 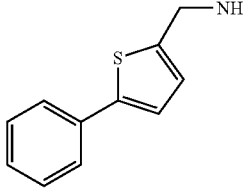 | Type II | 410 nm | 431 nm |
| 24 | 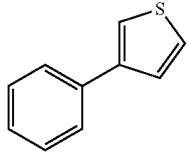 [SMILES: c1ccc(-c2ccsc2)cc1] | Type I | 416 nm | 385 nm |
| 25 | 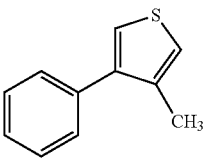 | Type I | 416 nm | 385 nm |
| 26 | 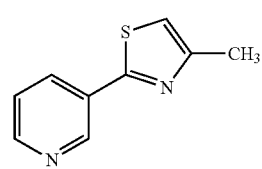 | Type I | 416 nm | 385 nm |

TABLE 8-continued

Spectral interaction analysis of heteroaromatic nicotine analogues with synthetic N-terminal truncated CYP2A6.

| Compd | Structure | binding type | $\lambda_{min}$ | $\lambda_{max}$ |
|---|---|---|---|---|
| 27 | (pyridin-3-yl pyrazole, NH) | Type II | 410 nm | 427 nm |
| 30 | (pyridin-3-yl propylamine) | Type II | 410 nm | 430 nm |
| 32 | (pyridin-3-yl aminomethyl pyrazole) | Type II | 410 nm | 430 nm |
| 35 | (pyridin-3-yl aminomethyl isoxazole) | Type II | 410 nm | 430 nm |

<sup>a</sup>The methyl groups on the nitrogen of this compound forbid binding to the heme iron (see text).
<sup>b</sup>The protein was preincubated with coumarin (2.5 μM), a Type I spectral shift was recorded and the test compound (100 μM) was added and, due to the low potency of the compound, failed to completely displace coumarin.
<sup>c</sup>The protein was preincubated with coumarin (2.5 μM), a Type I spectral shift was recorded and the test compound (100 μM) was added and completely displaced the coumarin.

Example 11

Inhibition of Human CYP2A13 and CYP2A6 and Mouse 2A5

CYP2A13 is one of three members of the human CYP2A gene family. CYP2A6 is a hepatic coumarin 7-hydroxylase and CYP2A13 is coumarin 7-hydroxylase found in the human lung. CYP2A7 is a pseudogene that codes for a non-functional enzyme.

CYP2A13 is expressed at the highest levels in the nasal mucosa but it is also expressed at relatively high levels in human lung and trachea (Su et al., *Cancer Research* 60: 5074-5079 (2000)). CYP2A6 is also detected in small amounts in the human lung (Crawford et al., *Carcinogenesis* 19:1867-1871 (1998); Kolsela et al., *Biochemical Pharmacology* 57:1407-1413 (1999); Su et al., *Cancer Research* 60:5074-5079 (2000)) and in human bronchial epithelial cells. However, the detection of CYP2A6 in lung and respiratory tract is controversial and the discrepancy may be due to the fact that the DNA primers for detection of each gene only varied by one nucleotide.

CYP2A6 metabolizes and bioactivates the carcinogens NNK and NNN and these carcinogens have been implicated as the causative agents of tobacco-related lung tumorigenesis. NNN primarily induces esophageal cancer in animals and has been implicated as causative in humans. CYP2A6 metabolizes NNN but it metabolizes NNK much less efficiently. On the other hand, CYP2A13 bioactivates NNK much more efficiently (i.e., 45-fold) than CYP2A6 (Patten et al., *Arhives Biochem Biophys.* 333:127-138 (1996)).

Because CYP2A13 is present in the human lung and is much more catalytically efficient at activating NNK to a proximate carcinogen than CYP2A6, CYP2A13 therefore plays an important role in tobacco-related lung cancers.

While some reports have characterized the volume of the substrate binding site of CYP2A13 as slightly larger than CYP2A6 (Johnson et al., *Drug Metab. Reviews* 35, 2, 2003), the crystal structure of CYP2A13 has not been solved and this information has been deduced from modeling of the crystal structure of CYP2A6 onto CYP2A13. This can also be seen by examining inhibitor potency of methoxypsoralen (8-methoxypsoralen) that has a $K_i$ value of 0.11 μM for CYP2A13 (von Weymarn et al., *Carcinogenesis* 348:1093 (2004)). A related compound, methoxsalen (9-methoxypsoralen) inhibits CYP2A6 with a $K_i$ value of 1-2 μM. Presumably, the larger psoralen compounds can not enter the substrate binding domain of CYP2A6 as easily as that of CYP2A13. It is notable that in animal studies of lung tumorigenesis, methoxsalen strongly inhibited the NNK-dependent tumorigenesis in mice (Takeuchi et al., *Cancer Res.* 63:7581-7583 (2003)). In view of the current data, it is possible that the chemoprevention effects were due to methoxsalen inhibition of CYP2A4 and/or CYP2A5 (the mouse homologs of human CYP2A6 and CYP2A13, respectively) in the lung. However, use of methoxsalen or other psoralens have liabilities because of the toxicities inherent to this class of compounds.

As shown in Table 9, some of the compounds that are potent inhibitors of CYP2A6 are also potent inhibitors of CYP2A13. For example, the thiophene TD-II-025 potently inhibits CYP2A6 ($IC_{50}$=0.622 μM) and also potently inhibits CYP2A13 (approximate $IC_{50}$ value=1 μM). Likewise, thiophenes TD-III-085-39, TD-IV-011-SSP-33 and TD-II-077 possess $IC_{50}$ values in the 1-5 μM range. Thus, compounds with selectivity for CYP2A13 can be synthesized based on the structures thus far examined for CYP2A6. The data is validated based on the inhibition of mouse CYP2A5 (which functionally is very similar to human CYP2A13 and has very high sequence homology). Thus, similar to human CYP2A13, mouse CYP2A5 has considerable selectivity for inhibition by pyridyl thiophenes.

Dual CYP2A6 and CYP2A13 inhibitors could be quite useful as compounds with smoking cessation and chemoprevention activity. In addition, compounds selective for CYP2A6 or CYP2A13 could also be useful in their own right.

TABLE 9

Inhibition of Human CYP2A13, comparison with Human CYP2A6 and mouse CYP2A5.

| Compound | Name (Page No. of Experimental) | $IC_{50}$ 2A6 (μM) | Percent inhibition CYP2A13 at 1 μM | $IC_{50}$ mCYP2A5 (μM) |
|---|---|---|---|---|
| 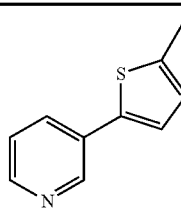 | TD-II-039 | 0.172 ± 0.017 | Not done, nd | 0.5 |
| 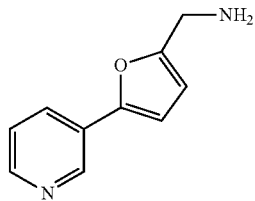 [SMILES: NCc1ccc(-c2cccnc2)o1] | TD-II-063 | 0.268 ± 0.0211 | 29 | 0.6 |
| 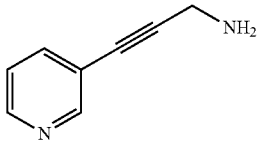 | TD-II-129 TD-III-101 26 | 0.514 ± 0.055 | 0 | nd |
| 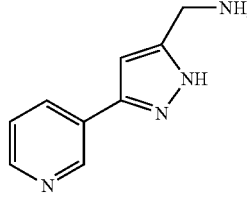 | TD-VIII-081 | 0.58 ± 0.08 | nd | nd |
| 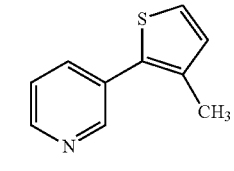 | TD-II-025 | 0.622 ± 0.087 | 51 | 0.3 |
| 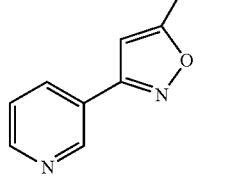 | TD-VIII-083 | 0.74 ± 0.09 | 7 | nd |

TABLE 9-continued
Inhibition of Human CYP2A13, comparison with Human CYP2A6 and mouse CYP2A5.
| Compound | Name (Page No. of Experimental) | IC$_{50}$ 2A6 (μM) | Percent inhibition CYP2A13 at 1 μM | IC$_{50}$ mCYP2A5 (μM) |
|---|---|---|---|---|
| 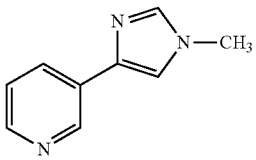 | TD-I-133 | 0.748 ± 0.1 | nd | nd |
| 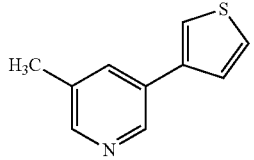 | TD-IV-049 29 | 1.0 ± 0.29 | nd | nd |
| 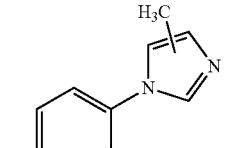 | EW-I-83B | 1.02 ± 0.23 | 0 | nd |
| 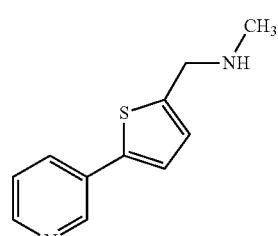 | TD-IV-073 30 | 1.10 ± 0.13 | 17 | 0.9 |
| 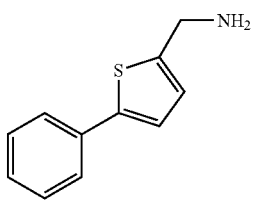 [SMILES: NCc1ccc(-c2ccccc2)s1] | TD-VIII-089 | 1.16 ± 0.11 | nd | nd |
| 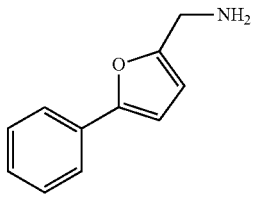 [SMILES: NCc1ccc(-c2ccccc2)o1] | TD-VIII-079 | 1.23 ± 0.16 | nd | nd |
| 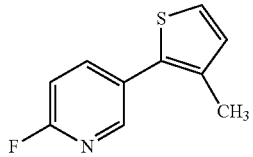 | TD-II-077 | 1.29 ± 0.14 | 30 | nd |

TABLE 9-continued
Inhibition of Human CYP2A13, comparison with Human CYP2A6 and mouse CYP2A5.
| Compound | Name (Page No. of Experimental) | IC$_{50}$ 2A6 (μM) | Percent inhibition CYP2A13 at 1 μM | IC$_{50}$ mCYP2A5 (μM) |
|---|---|---|---|---|
| 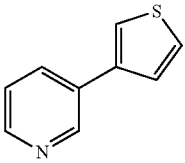 [SMILES: c1cncc(-c2ccsc2)c1] | TD-I-145 | 1.37 ± 0.23 | 12 | 0.8 |
| 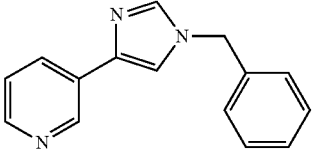 [SMILES: c1ccc(Cn2cnc(-c3cccnc3)c2)cc1] | TD-II-111 | 1.39 ± 0.19 | 17 | nd |
| 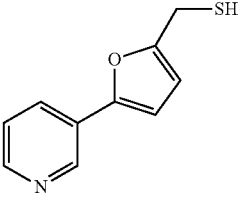 [SMILES: SCc1ccc(-c2cccnc2)o1] | TD-V-111 31 | <1.5 | 11 | nd |
| 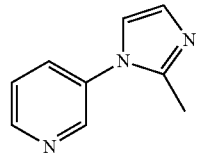 | EW-I-53 | 1.50 ± 0.35 | 0 | nd |
| 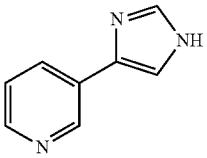 | TD-I-125 | 1.51 ± 0.31 | 7 | nd |
| 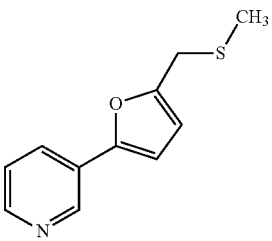 | TD-VI-055 32 | 1.6 ± 0.19 | 16 | nd |
| 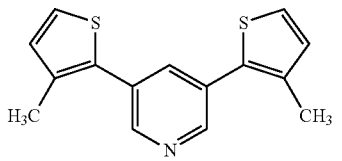 [SMILES: Cc1ccsc1-c1cncc(-c2sccc2C)c1] | TD-IV-011 SSP 33 | 1.63 ± 0.65 | 19 | nd |

TABLE 9-continued

Inhibition of Human CYP2A13, comparison with Human CYP2A6 and mouse CYP2A5.

| Compound | Name (Page No. of Experimental) | IC$_{50}$ 2A6 (µM) | Percent inhibition CYP2A13 at 1 µM | IC$_{50}$ mCYP2A5 (µM) |
|---|---|---|---|---|
| [structure: 5-(pyridin-3-yl)furan-2-yl methyl methylamine] | TD-IV-099 34 | 1.6 ± 0.34 | 0 | nd |
| [structure: 6-chloropyridinium alkyne propargylammonium dichloride] | TD-VIII-031 | ≤1.68 ± 0.34 | nd | nd |
| [structure: S-((5-(pyridin-3-yl)furan-2-yl)methyl) ethanethioate] | TD-V-099 | 1.8 ± 0.3 | 13 | nd |
| [structure: 2-chloro-3-(pyridin-3-yl)thiophene] | TD-III-083 37 | 1.82 ± 0.17 | 13 | nd |
| [structure: 3-methyl-4-(pyridin-3-yl)thiophene] | TD-I-103 | 1.85 ± 0.5 | 0 | 0.75 |
| [structure: (E)-5-(pyridin-3-yl)thiophene-2-carbaldehyde oxime] | TD-II-051 | 1.93 ± 0.33 | nd | nd |
| [structure: β-Nicotyrine, 3-(1-methyl-1H-pyrrol-2-yl)pyridine] | β-Nicotyrine Nat. Prod. | 2.2 ± 0.22 | nd | nd |

TABLE 9-continued
Inhibition of Human CYP2A13, comparison with Human CYP2A6 and mouse CYP2A5.
| Compound | Name (Page No. of Experimental) | IC$_{50}$ 2A6 (μM) | Percent inhibition CYP2A13 at 1 μM | IC$_{50}$ mCYP2A5 (μM) |
|---|---|---|---|---|
| 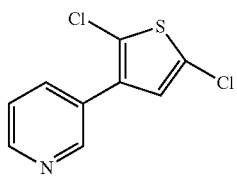 [SMILES: Clc1cc(-c2cccnc2)c(Cl)s1] | TD-III-081 38 | 2.41 ± 0.29 | 19 | nd |
| 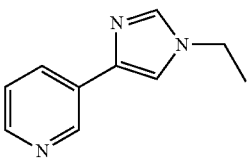 | TD-II-109 | 3.14 ± 0.33 | nd | nd |
| 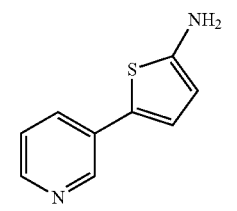 [SMILES: Nc1ccc(-c2cccnc2)s1] | TD-I-137 | 3.51 ± 0.28 | 0 | nd |
| 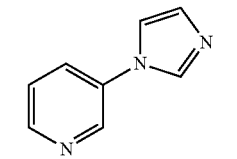 [SMILES: c1cncc(-n2ccnc2)c1] | SD-I-21 | 3.74 ± 0.78 | nd | nd |
| 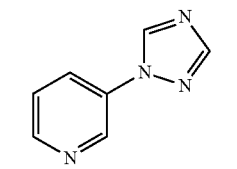 [SMILES: c1cncc(-n2cncn2)c1] | TD-II-143 | 4.2 ± 0.8 | 18 | nd |
| 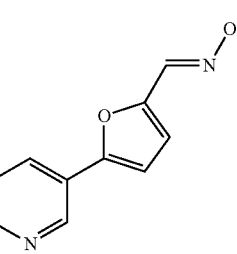 | TD-II-065 ESP trans isomer | 4.24 ± 0.49 | 41 | nd |
|  | TD-III-085 39 | 4.67 ± 0.61 | 27 | nd |

TABLE 9-continued

Inhibition of Human CYP2A13, comparison with Human CYP2A6 and mouse CYP2A5.

| Compound | Name (Page No. of Experimental) | IC$_{50}$ 2A6 (µM) | Percent inhibition CYP2A13 at 1 µM | IC$_{50}$ mCYP2A5 (µM) |
|---|---|---|---|---|
| [structure] | TD-II-031 | 4.77 ± 0.74 | nd | nd |
| [structure] | TD-IV-091 41 | 5.36 ± 0.61 | 2 | nd |

Example 12

Novel Neuronal Nicotinic Acetylcholine Receptor Binding Agents

Neuronal nicotinic acetylcholine receptors (nAChRs) are members of a neurotransmitter-gated ion channel superfamily of receptors that regulate a host of neuronal functions. The α/β and α7 nAChRs are some of the most abundant nAChR subtypes in the human brain (Flores et al., 1992). The role of this receptor in nicotine addiction is multi-fold. The α/β nAChR has been implicated to intervene in both the dopamine (Serova and Sabban, 2002) and catecholamine (Slotkin et al., *Biochem. Pharmacol.* 25, 1311-1315, 1976; Fossam et al., *J. Neurochem.* 85 Suppl. 2, 26, 1991) biosynthetic pathway, which are intimately involved in the euphoric feeling one acquires from nicotine. In addition to being involved in nicotine addiction, this receptor has also been characterized as the major player in a number of neurodegenerative disorders. For example, the nAChR has been implicated in Alzheimer's Disease, Parkinson's disease and dementia. Nicotine has been shown to be beneficial for some of these neurodegenerative disorders and nicotine analogues have potential for therapeutic use in all of these disorders. Intervention at the level of the nAChR by novel ligands will have high potential as smoking cessation agents. Stimulation of the α7 nAChR may have particular utility in Alzheimer's Disease.

To determine the functional properties of the α7 nAChR, or any large, membrane bound protein, is difficult because the hydrophobicity and size make these types of receptors makes studies challenging. Conventional studies using whole cell, membrane bound receptors to elucidate binding effects are highly valuable tools, but these data do not usually provide structural or mechanistic details of the receptor-ligand interactions. One would like to have an X-ray crystal structure to study the exact ligand binding interactions, but the crystal structure of the α7 nAChR is not available, nor is it anticipated any time soon. An alternative approach is to utilize a soluble homologue of the α7 nAChR that is not membrane bound and has a crystal structure available.

Recently, an acetylcholine binding protein (AChBP) from the fresh water snail *Lymnaca stagnalis* was crystallized, characterized as an α7 nAChR surrogate and its non-ligated crystal structure determined. Details on the ligand selectivity, binding kinetics and conformational changes that correspond to ligand-protein interactions show that its characteristics are functionally related to the function of the mammalian α7 nAChR.

The library of nicotine analogues were screened as potential ligands for the AChBP (see Table 10). Of the library of compounds synthesized, a number of lead structures were identified that possessed significant avidity for the receptor. Thus, in a radiolabelled bungarotoxin binding assay, several compounds were very potent at displacing radioligand from the AChBP. The cyclopropylamine and the bis thiophene compounds very potently interacted with the AChBP (Table 10). The data shows that relatively simple analogs of nicotine can be elaborated to potently interact with AChRs or BPs. Because many of these same compounds potently inhibit the enzyme system responsible for nicotine metabolism, the feasibility of developing dual functional activity (inhibition of nicotine metabolism and interaction with AChRs) is shown. Placing appropriate electron-withdrawing substituents into the pyridine ring to mimic epibatidine (a potent ligand of AChR) in the lead compounds shown (Table 10) should afford potent dual activity compounds.

TABLE 10

Inhibition of Radioligand Binding to the Acetylcholine Binding Protein

| compound | Name | % of Control |
|---|---|---|
| [structure: pyridin-3-yl cyclopropanamine] | 2-(pyridin-3-yl)cyclopropanamine | 8 |
| [structure: bis-thiophene amine] | bis((5-(pyridin-3-yl)thiophen-2-yl)methyl)amine | 10 |
| [structure: pyridin-3-yl furan methanamine] | (5-(pyridin-3-yl)furan-2-yl)methanamine | 20 |
| [structure: tetrahydrofuran, 95% trans] | (tetrahydro-5-(pyridin-3-yl)furan-2-yl)methanamine | 25 |
| [structure: tetrahydrofuran, 50% trans] | (tetrahydro-5-(pyridin-3-yl)furan-2-yl)methanamine | 30 |

% of control = % $^{125}$I bungarotoxin binding in the presence of inhibitor relative to that of untreated binding protein = the lower the value the better the ligand

Example 13

SAR Analysis of CYP2A6 Inhibitors

Results and Discussion

The effect of nicotine and 3-substituted heteroaryl pyridine analogues of nicotine on the functional activity of cDNA-expressed human CYP2A6 was determined by examining coumarin 7-hydroxylation. The enzyme assay was established using standard conditions and coumarin 7-hydroxylation was shown to be linearly dependent on incubation time (0 to 90 minutes) and protein concentration (0.5 to 2.0 pmol of protein). Of the compounds examined, thirty six nicotine analogues showed greater potency at inhibiting coumarin 7-hydroxylase functional activity compared with that of nicotine (Table 2). Two nicotine analogues (i.e., compounds 38a and 39a) showed $K_i$ values of 20±3 and 40±4 nM, respectively. Apparently, the methyl amino group of compound 38a was essential for potent inhibition, because replacement with an aldehyde (i.e., compound 13, $K_i$=0.79±0.12 µM), absence of the methyl amino group (i.e., compound 7, $K_i$=1.2±0.6 µM), replacement with a methyl ketone (i.e., compound 14, $K_i$=1.4±0.2 µM), a methyl alcohol (i.e., compound 44, $K_i$=5.6±0.7 µM) or nitro group (i.e., compound 15, $K_i$=19.7±2.3 µM) decreased inhibitor potency 40-, 60-, 70-, 280- and 985-fold, respectively. The methyl amino group of compound 39a was also determined to be essential for potent inhibition, because replacement with a methyl alcohol (i.e., compound 45, $K_i$=35.2±16.7 µM) or an aldehyde (i.e., compound 23, $K_i$=≥67 µM) decreased inhibitor potency 880- and 1675-fold, respectively.

In all cases examined, modification of the methyl amino group of compounds 38a and 39a decreased inhibitor potency. For example, oxidation of compound 38a into a mixture of cis/trans oxime isomers decreased the $K_i$ value for inhibition of coumarin 7-hydroxylation (i.e., compound 36, $K_i$=0.24±0.04 µM) 12-fold. For compounds 37a and 37b, where trans and cis oxime regioisomers could be chromatographically separated, significant regioselectivity of coumarin 7-hydroxylase inhibition was observed (i.e., trans compound 37a, $K_i$=0.71±0.08 µM, cis compound 37b, $K_i$=13.7±1.2 µM). Although, like the thiophene oxime mixture (compound 36), the potency was significantly less (i.e., 18- and 343-fold) for the trans and cis oxime regioisomers, respectively, compared with the parent amine compound 39a (Table 2). Modification of the primary amines 38a and 39a to afford secondary amines (compounds 38b and 39b) or a tertiary amine (compound 39c), decreased inhibitor potency 60-, 38- and 70-fold, respectively.

To examine the SAR of the most potent CYP2A6 inhibitors (e.g., 38a and 39a), variation of the amino terminus was done. In addition, the distance between the pyridine and the terminal amino moiety was varied. Finally, the effect of substituents at the 5- and 6-position of the pyridine nucleus was examined. Elaboration of an N-methyl (i.e., compound 40, $K_i$=0.18±0.02 µM) or an N,N-dimethyl (i.e., compound 42, $K_i$=22.2±3.3 µM) substituent to 38a decreased the potency of inhibition 9- and 1110-fold, respectively. Likewise, addition of an N-methyl (i.e., compound 41, $K_i$=0.28±0.06 µM) or an N,N-dimethyl (i.e., compound 43, $K_i$=47.2±3.1 µM) substituent to 39a decreased the potency of inhibition 7- and 1180-fold, respectively. Thus, monomethyl substituents in the terminal amino group only moderately decreased inhibitor potency while dimethyl substituents significantly decreased inhibitor potency. Placement of an acetylenic group between the pyridine and methyl amino functionality, in which the distance is approximately the same as in compounds 38a and 39a, resulted in a potent CYP2A6 inhibitor (i.e., compound 48, $K_i$=0.09±0.01 µM). In agreement with that observed for 38a and 39a, addition of an N-methyl (i.e., compound 50, $K_i$=0.89±0.10 µM) or an N,N-dimethyl (i.e., compound 51, $K_i$=22.7±7.8 µM) substituent to 48 decreased the potency of inhibition 10- and 252-fold, respectively. Increasing the distance between the pyridine and methyl amino functionality by the insertion of a phenyl group (i.e., compound 54, $K_i$=1.4±0.3 µM) resulted in a 70-, 35- and 16-fold decrease in CYP2A6 inhibitory potency when compared to the thiophene-linked, furan-linked and acetylene-linked analogues, respectively. The effect of substituents in the 5-position of the pyridine nucleus resulted in a variable effect on CYP2A6 inhibitory potency. For example, addition of a bromine atom (i.e., compound 12, $K_i$=1.5±0.2 µM) or a methyl group (i.e., compound 55, $K_i$=11±1.5 µM) to the 5-position of 9 decreased the $K_i$ value for inhibition of coumarin 7-hydroxylation 15- and 110-fold, respectively. Compared to compound 16 ($K_i$=0.22±0.04 µM), addition of a bromine atom (i.e., compound 19, $K_i$=4.5±0.8 µM) to the 5-position decreased the $K_i$ value for inhibition of coumarin 7-hydroxylation 20-fold, although the addition of a methyl group (i.e., compound 56, $K_i$=0.17±0.05 µM) to the 5-position of 16 increased the $K_i$ value for inhibition of coumarin 7-hydroxylation 1.3-fold. Although intriguing, the data suggest that the introduction of functional groups to the five position of the pyridine nucleus did not contribute to an appreciable increase in CYP2A6 inhibition potency and, thus, was not examined further.

To further evaluate the SAR of inhibition of CYP2A6 for the pyridine portion of the inhibitors, the pyridine ring was substituted at the 6-position with a methoxy-, chloro- or fluoro-group. Because of the ease of synthesis, compounds 9, 16, 20 and 31 were chosen to be modified in the pyridine 6-position. Compared to compounds 9 ($K_i$=0.1±0.02 µM), 16 ($K_i$=0.22±0.04 µM) and 20 ($K_i$=0.25±0.04 µM), introduction of a methoxy group resulted in an increase in the $K_i$ value to >67 µM, 9.7±2.1 µM, and 6.6±0.8 µM for analogues 11, 18 and 22, respectively (Table 2). These data suggest that either the region that accommodates the pyridine 6-position of the active site is limited or that an electron donating substituent at the 6-position modulates the potency of CYP2A6 inhibition in a detrimental manner. The introduction of a chlorine atom at the pyridine 6-position of 31 (K=1.1±0.1 µM) afforded 32 that had a $K_i$ value of 6.3±2.5 µM and afforded a 6-fold loss in potency. To determine if the electron withdrawing properties or the size of the chlorine atom was responsible for this decreased $K_i$ value, compounds 10, 17 and 21, that contain a fluorine atom on the pyridine 6-position, were synthesized. In each case examined, the introduction of a fluorine atom increased the $K_i$ value of the parent compound and decreased the potency of inhibition 2- to 10-fold. Thus, the $K_i$ value of analogue 10 increased to 0.21±0.02 µM from parent 9 ($K_i$=0.1±0.02 µM), the $K_i$ value of analogue 17 increased to 0.97±0.20 µM from parent 16 ($K_i$=0.22±0.02 µM) and the $K_i$ value of analogue 21 increased to 2.6±0.5 µM from parent 20 ($K_i$=0.25±0.04 µM). In general, the data suggest that introduction of electron donating or electron withdrawing functional groups (i.e., $CH_3O$—, F—, Cl—) to the pyridine 6-position was detrimental to potency of coumarin 7-hydroxylase inhibition and thus, modifications of the pyridine 6-position were not explored further.

In light of the observations above, and the limited synthetic and commercial access to 4-substituted-pyridin-3-yl-3-boronic acids, additional SAR studies of the pyridine 4-position were not explored.

Next, we examined if replacement of the methyl amino furan or methyl amino thiophene moeity (i.e., compounds 38a and 39a) by a different nitrogen-containing heterocycle would retain coumarin 7-hydroxylase inhibition potency. Analogue 34, with a 1H-imidazole-4-yl moiety at the pyridine 3-position possessed a $K_i$ value of 0.25±0.05 µM. To examine the allowable molecular space in the CYP2A6 active site, the 1H nitrogen of 34 was alkylated with methyl iodide, ethyl iodide and benzyl bromide to afford analogues 58a, b (tested as a mixture of regioisomers), 59 and 60 that had $K_i$ values of 0.13±0.02, 0.52±0.05 and 0.23±0.03 µM, respectively. That negligible loss of inhibitor potency was observed upon introduction of a benzyl group into compound 60 suggested that there was a significant amount of space available in the CYP2A6 active site to accommodate large alkyl groups at this position of the heteroaryl group. The analogues 61 (tested as a mixture of 3-(4- and 5-methyl-1H-imidazol-1-yl) pyridine regioisomers) and compounds 62 and 63 possessed $K_i$ values of 0.17±0.04, 0.25±0.06 and 0.62±0.13 µM, respectively, reinforcing the suggestion that there is an adequate amount of room in the active site to allow for additional functionality to the five membered heterocycle attached to the pyridine 3-position. To further probe the CYP2A6 active site, compounds 15 and 57 were determined to have $K_i$ values of 19.7±2.3 and 0.59±0.05 respectively, suggesting that the nitro group is too large or not sufficiently nucleophillic to afford potent CYP2A6 inhibition, but the amino group is appropriate to provide a potent CYP2A6 inhibitor.

Heteroaromatic analogues of nicotine that inhibited coumarin 7-hydroxylation with $K_i$ values below 1.5 µM were selected to be examined for selectivity of P450 inhibition. The nicotine analogues were tested as inhibitors of human CYP2E1, 2B6, 2C9, 2C19 and 2D6 with high throughput fluorescence assays using cDNA-expressed human CYPs prepared from transfected insect cell microsomes (Marks, *ASAY and Drug Develop. Tech.* 1:73-81 (2002). CYP3A4 mediated testosterone 6-hydroxylation inhibition was assayed using human liver microsomes and a standard HPLC-based assay (Wood et al., *J. Biol. Chem.* 258:88398847 (1983)). Full dose-range $IC_{50}$ values were obtained and the CYP inhibition data is presented in Table 3. The selectivity ratios (i.e., $IC_{50}$ CYPX/$IC_{50}$ CYP2A6) are given in Table 4. Of the analogues tested, the CYP3A4/CYP2A6 selectivity ratio varied from 2 for analogue 57 to 400 for 16, CYP2E1/CYP2A6 varied from 0.4 for 60 to 637 for 39a, CYP2B6/CYP2A6 varied from 1.2 for 38b to 707 for 39a, CYP2C9/CYP2A6 varied from 0.1 for 38b to >400 for 61, CYP 2C19/CYP2A6 varied from 0.03 for 38b to >294 for 61 and CYP2D6/CYP2A6 varied from 1.7 for 38b to 988 for 38a (Table 3). The most potent CYP2A6 inhibitors examined, 38a and 39a, were found to be moderately to highly selective inhibitors for CYP2A6. Nicotine analogue 38a had selectivity ratios of 345, 236, 307, 52, 12 and 988 for CYPs 3A4, 2E1, 2B6, 2C9, 2C19 and 2D6, respectively. Compound 39a had selectivity ratios of 174, 637, 707, 41, 82, and 41 for CYPs 3A4, 2E1, 2B6, 2C9, 2C19 and 2D6, respectively. We judge that selectivity ratios greater than 10 possess significant utility, although this is somewhat dependent on the enzyme to which CYP2A6 is being compared.

Interestingly, the secondary amine, compound 38b showed relatively poor CYP2A6 selectivity and, conversely, was somewhat selective for inhibition of CYP2C19. It is known that CYP2C19 (Jung et al., *Biochem.* 37:16270-16279 (1998)) can accommodate significantly larger inhibitors than CYP2A6, but this needs to be explored further.

Two of the compounds were tested in vivo. Briefly, male Wistar rats were allowed to self-administer nicotine (0.01 mg/kg; 0.1 ml infusion/1 sec) across a 23-hr period each day for 49 days according to a modification of a previously published protocol (Watkins et al., *Pharmacol Biochem Behavior* 62, 743-751 (1999). On day 50, a nicotine-addicted animal was treated with the dihydrochloride salts of compounds 2 (16 mg/kg) or 14 (15 mg/kg) (Table 1) in sterile saline. Compound 2 decreased nicotine self-administration by 70% and compound 14 decreased nicotine self-administration by 40% during day 50. The effect persisted beyond one day, as the amount of nicotine self-administration during day 51 and 52 was also decreased, although the effect for compound 2 was more pronounced on day 51 and 52 than that for compound 14.

CONCLUSIONS

A series of substituted pyridines in which the pyridine ring was substituted with halogens or a methoxy group and/or the N-methylpyrrolidine ring of nicotine was replaced with substituted and unsubstituted heteroaromatic rings have been prepared and evaluated as inhibitors of human CYPs 2A6, 3A4, 2E1, 2B6, 2C9, 2C19 and 2D6 with the goal of finding a potent and selective inhibitor of human CYP2A6. Of the compounds examined, the most potent inhibitors of CYP2A6 observed were 38a and 39a. Compounds 38a and 39a were also found to be relatively selective inhibitors of CYP2A6. We have shown that inclusion of the methylamino moiety on the 5-position of the thiophene and furan rings in analogues 38a and 39a imparted potent inhibition, that the introduction of a bromine atom or methyl group at the 5-position either decreased or did not change the inhibitor potency, that the introduction of a methoxy, chloro or fluoro group at the 6-position of the pyridine ring decreased inhibitory potency and that the introduction of large alkyl groups on the heteroaromatic ring did not significantly decrease CYP2A6 inhibitory potency. The data presented herein is interpreted to provide information about the competitive nature of CYP2A6 inhibition. Under certain conditions, however (i.e., at very high inhibitor concentrations), a few of the inhibitors of Table 4 showed time-dependent inactivation (unpublished results). Therefore, at a concentration range near the $K_i$ value, the inhibition of CYP2A6 was competitive in nature. The compounds were also examined for type 1 versus type 2 binding to a synthetic, cDNA-expressed CYP2A6 enzyme. Compounds such as 9 and 55 showed type 1 binding spectra while compounds 38a and 39a showed type 2 binding spectra (unpublished results). Nicotine analogues 38a and 39a may serve as lead structures to develop even more potent and selective inhibitors of CYP2A6 that may prove to be valuable for the development of novel non-nicotine smoking cessation agents. However, even compounds 2 and 14 (Table 1) showed significant in vivo activity against nicotine addicted rats self-administering nicotine and the effect of one dose persisted in some cases for 2-3 days.

EXPERIMENTAL SECTION

General.

Commercially available reagents were purchased from Aldrich chemical company or VWR and were used as received. All moisture sensitive reactions were carried out in flame-dried glassware under an argon atmosphere. Tetrahydrofuran (THF) and toluene were freshly distilled from calcium hydride under an argon atmosphere. Methanol ($CH_3OH$) was passed through a column of neutral alumina and stored over 3 Å molecular sieves prior to use.

Melting points were determined on a Mettler-Toledo FP62 melting point instrument and are uncorrected. Analytical thin-layer chromatography (TLC) was done on K6F silica gel 60 Å (Whatman) glass-backed plates. Compounds were detected using UV absorption at 254 nm and/or stained with $I_2$ (iodine). Flash chromatography was done on Merck (60 Å) pore silica. NMR spectra were recorded at 500 MHz by NuMega Resonance Labs, Inc., (San Diego, Calif.). Chemical shifts were reported in parts per million (ppm, δ) using residual solvent signals as internal standards. Low resolution mass spectroscopy (LRMS) was done with an HP 1100 mass spectrometer at HT Laboratories (San Diego, Calif.) using electrospray ionization (ESI) or at the Human Biomolecular Research Institute on a Hitachi M-8000 3DQMS (ion trap) mass spectrometer using ESI. High resolution mass spectroscopy (HRMS) was done with a Micromass LCT time of flight mass spectrometer at the University of Montana Mass Spectral Facility (Missoula, Mont.) using ESI.

The nicotine analogues were characterized by $^1$H NMR, LRMS, HRMS and their purifies (>95%) were determined by HPLC in two distinct solvent systems. Analytical HPLC measurements were run on a Hitachi L-6200 system equipped with a Hitachi L-7400 UV detector. Separations were done (straight-phase) with an Axxi-cbrom silica column (4.6 mm×250 mm, 5 μm) or (reverse-phase) with a Supelco HS F5 pentafluorophenyl column (4.6 mm×250 mm, 5 μm). Standard conditions utilized an isocratic, ternary-solvent system consisting of solvents A (methanol), B (isopropanol) and C($HClO_4$) set at a flow rate of 1.5 mL/min (straight-phase), or A, D (water) and E ($HCO_2H$) set at a flow rate of 1.0 mL/min (reverse-phase), λ=254 nm with retention times ($t_R$) evaluated in minutes. Typical analyses involved two distinct isocratic elutions per compound of interest. Solvent conditions for the isocratic elutions were varied depending on the compound and its specific chromatographic properties. $^1$H NMR and mass spectra are consistent with the assigned structures.

Biological Assay.

Microsomes from human lymphoblast cells expressing specific human cytochrome P-450 2A6 and human liver microsomes (CYP3A4) were purchased from BD Gentest (Woburn, Mass.) and microsomes from baculovirus-infected cells co-expressing cytochrome P-405s (2E1, 2B6, 2C9, 2C19 and 2D6), NADPH-cytochrome P-450 reductase and cytochrome $b_5$ (BACULOSOMES®) were purchased from PanVera LLC (Madison, Wis.).

To measure CYP2A6 activity, coumarin 7-hydroxylation was determined. Microsomes containing 5 µM CYP2A6 were added to 0.1 M Tris buffer (pH 7.5) containing 3 µM coumarin (final concentration) and individual inhibitors with final concentrations of 0.02, 0.1, 0.4, 1.6, 6.3, 25, 100 and 400 µM. The reactions were initiated by the addition of an NADPH-generating system consisting of 0.5 mM NADP$^+$, 0.5 mM glucose-6-phosphate, 5 U glucose-6-phosphate dehydrogenase, 1 mg/ml diethylenetriaminepentaacetic acid (DETAPAC) and 7 mM MgCl$_2$ for a final incubation volume of 0.2 mL. Incubations were run for 10 min at 37° C. and were terminated by the addition of 0.75 mL of ice cold CCl$_3$COOH/CH$_3$CN (20:80, w/v). After centrifugation at 13,000 rpm for 5 min, 200 µL of the supernatant was transferred to a Packard OptiPlate 96-well plate. The formation of the coumarin metabolite, 7-hydroxycoumarin, was determined fluorometrically using a Wallac Victor (Vial supra) 1420 Multilabel Counter (Wallac Software, Version 2.00, release 9) at excitation and emissions wavelengths of 355 and 460 nm, respectively. The amount of product formed was obtained by interpolation from a standard curve of 7-hydroxycoumarin. The IC$_{50}$ values were determined using GraphPad Prism Version 3.00 and are reported as an average of three experiments±SD. Apparent $K_i$ values were determined from the IC$_{50}$ values using a $K_m$ for coumarin of 0.6 µM (average of the reported values) (Draper et al., *Arch. Biochem. Biophys.* 341:47-61 (1997)) employing the equation of Cheng and Prusoff. (Cheng et al. *Biochem. Pharmacol.* 22:3099-3108 (1973)). For each assay, the reaction was a linear function of time for 60 min and of protein concentration from 0.5 to 2 pmol.

To measure CYP3A4 activity, testosterone 6-hydroxylation was determined. Individual inhibitors with final concentrations of 0.02, 0.1, 0.4, 1.6, 6.3, 25, 100 and 400 µM were added to ice cold 0.05 M potassium phosphate buffer (pH 7.5) containing human liver microsomes (0.4 mg), an NADPH-generating system consisting of 0.5 mM NADP$^+$, 2.0 mM glucose-6-phosphate, 1 U glucose-6-phosphate dehydrogenase, 0.6 mg/mL DETAPAC and 3 mM MgCl$_2$. The reactions were initiated by the addition of substrate (testosterone, final concentration: 0.2 mM) for a final incubation volume of 0.25 mL. Incubations were run for 30 min with shaking in air at 37° C. and were terminated by the addition of 1.5 mL ice cold ethyl acetate (EtOAc). After centrifugation at 13,000 rpm for 5 min, the organic phase was collected and removed with a stream of nitrogen. The residue was reconstituted in methanol (200 µL), centrifuged at 13,000 rpm for 5 rain and the supernatant was analyzed by high-performance liquid chromatography (Altex Ultrasphere ODS column, 5 µm, 250×4.6 mm, γ=254 nm using an isocratic mobile phase consisting of H$_2$O/CH$_3$CN/MeOH, (30:10:60, v/v/v) set at a flow rate of 1 ml/min. Under these conditions the following retention times were observed: 6-hydroxytestosterone, $t_R$ 3.94 min; testosterone, $t_R$ 7.95 min).

To measure CYP2E1, CYP2B6, CYP2C9, CYP2C19 and CYP2D6 activity, isozyme specific vivid blue substrate O-dealkylation was determined via a modified PanVera Vivid Assay Protocol. Individual inhibitors with final concentrations of 0.02, 0.1, 0.4, 1.6, 6.3, 25, 100 and 400 µM or 0.14, 1.2, 3.7, 33, 100 and 300 µM were added to a 96-well plate (BD Falcon™ Microtest™, Black Flat Bottom) containing Vivid® Substrate (final concentration: CYP2B6, 5 µM; CYP2C9, 10 µM; CYP2C19, 10 µM; CYP2D6, 10 µM and CYP2E1, 10 µM) in 0.2 M potassium phosphate buffer (pH 8.0), followed by isozyme specific BACULOSOMES (enzyme final concentration: CYP2B6, 10 nM; CYP2C9, 10 nM; CYP2C19, 5 nM; CYP2D6, 10 nM and CYP2E1, 5 nM). The reactions were initiated by the addition of an NADPH-generating system consisting of 0.5 mM NADP$^+$, 0.5 mM glucose-6-phosphate, 5 U/mL glucose-6-phosphate dehydrogenase, 1.0 mg/mL DETAPAC and 7 mM MgCl$_2$ for a final incubation volume of 0.2 mL. After a 40 min incubation at room temperature, the formation of the fluorescent, O-dealkylated metabolite for each isozyme was determined fluorometrically at excitation and emission wavelengths of 405 nm and 460 nm, respectively.

The IC$_{50}$ values were determined using GraphPad Prism Version 3.00 and were reported as an average of three experiments±SD. For each assay, the reaction was a linear function of time for 60 min and of protein concentration from 0.5 to 2 pmol per reaction well.

General Procedure for the Preparation of Pyridin-3-yl-Boronic Acids (1-6).

Compounds 1-6 were prepared by the esterification of the appropriate lithiopyridine followed by hydrolysis as previously reported (Cai et al., *Tetrahedron Lett.* 43:4285-4287 (2002)). The synthesis of pyridin-3-yl-3-boronic acid (1) is representative of compounds 2-6.

/Pyridin-3-yl-3-boronic acid (1)

A 500 mL 3-neck flask was charged with toluene (85 mL), cooled to below −60° C. and a solution of n-BuLi (1.6 M in hexanes, 48.6 mL, 77.8 mmol) was added dropwise over 10 min. After the internal temperature reached −60° C. a solution of 3-bromopyridine (6.8 mL, 70.7 mmol) in toluene (30 mL) was added drop wise to keep the internal temperature below −50° C. A brownish-black solid precipitated and the resultant slurry was stirred for 20 min. THF (30 mL) was added dropwise to keep the internal temperature below −50° C. and the resultant slurry was stirred for 15 min. To the slurry was added triisopropyl borate (19.6 mL, 84.9 mmol) in one portion via syringe. The solution was warmed to −15° C., quenched with HCl$_{(aq)}$ (2.7 N, 70.0 mL) and transferred to a separatory funnel. The aqueous layer was collected and the organic layer was washed with water (10 mL), the combined aqueous layers were neutralized to pH 7 with NaOH$_{(aq)}$ (10 N) and extracted with THF (200 mL×1, 125 mL×2). The combined organics were concentrated in vacuo and the residue was dissolved in THF/CH$_3$OH (1:1, 140 mL), filtered and diluted to 300 mL with CH$_3$CN. The solvent was switched to CH$_3$CN by distillation and concentrated to 100 mL. The solids were collected by filtration to afford the title compound 1 (6.4 g, 73% yield) as an off white solid: $^1$H NMR (CD$_3$OD) δ 8.64 (br s, 1H), 8.50 (m, 1H), 8.38 (br s, 1H), 7.65 (br s, 1H). This material was used directly in Suzuki cross coupling reactions.

6-Fluoropyridin-3-yl-3-boronic acid (2)

5-Bromo-2-fluoropyridine was treated with n-BuLi (1.6 M in hexanes, 19.5 mL, 31.3 mmol), triisopropyl borate (7.9 mL, 34.1 mmol) and HCl$_{(aq)}$ (2.7 N, 28.4 mL) as for 1 to give the title compound 2 (3.0 g, 74% yield) as a brown semi-solid:

¹H NMR (CD₃OD) δ 8.45 (br s, 1H), 8.21 (br s, 1H), 7.01 (m, 1H). This material was used directly in Suzuki cross coupling reactions.

6-Methoxypyridin-3-yl-3-boronic acid (3)

5-Bromo-2-methoxypyridine (5.0 mL, 39.1 mmol) was treated with n-BuLi (1.6 M in hexanes, 26.9 mL, 43.0 mmol), triisopropyl borate (10.8 mL, 46.9 mmol) and $HCl_{(aq)}$ (2.7 N, 37.6 mL) as for 1 to give the title compound 3 (4.3 g, 89% yield) as a white solid: ¹H NMR (CD₃OD) δ 8.42 (m, 1H), 7.95 (br s, 1H), 6.76 (br s, 1H), 3.91 (s, 3H). This material was used directly in Suzuki cross coupling reactions.

6-Chloropyridin-3-yl-3-boronic acid (4)

5-Bromo-2-chloropyridine was treated with n-BuLi (1.6 M in hexanes, 12.0 mL, 19.1 mmol), triisopropyl borate (4.8 mL, 20.9 mmol) and $HCl_{(aq)}$ (2.7 N, 16.8 mL) as for 1 to give the title compound 4 (1.7 g, 60% yield) as a pink solid: ¹H NMR (CD₃OD) δ 8.58 (br s, 1H), 7.95 (br d, J=6.7 Hz, 1H), 7.95 (d, J=8 Hz, 1H). This material was used directly in Suzuki cross coupling reactions.

3-Methylthiophen-2-yl-2-boronic acid (5)

2-Bromo-3-methylthiophene was treated with n-BuLi (1.6 M in hexanes, 38.8 mL, 62.1 mmol), triisopropyl borate (15.1 mL, 65.4 mmol) and $HCl_{(aq)}$ (2.7 N, 52.5 mL) as for 1 to give the title compound 5 (7.2 g, 93% yield) as a brown solid: ¹H NMR (CD₃OD) δ 7.27 (d, J=5.5 Hz, 1H), 6.80 (d, J=5.5 Hz, 1H), 2.16 (s, 3H). This material was used directly in Suzuki cross coupling reactions.

Thiophen-3-yl-3-boronic acid (6)

3-Bromothiophene was treated with n-BuLi (1.6 M in hexanes, 8.4 mL, 13.5 mmol), triisopropyl borate (3.4 mL, 14.7 mmol) and $HCl_{(aq)}$ (2.7 N, 11.8 mL) as for 1 to give the title compound 6 (1.43 g, 91% yield) as a tan solid: ¹H NMR (CD₃OD) δ 7.85 (br d, 1H), 7.40 (m, 2H). This material was used directly in Suzuki cross coupling reactions.

General Procedure for Suzuki Coupling Reactions.

To a glass vial containing a magnetic stir bar is added the heteroarylbromide (1.30 mmol) and the vial is purged with argon. To the vial was added a solution of tetrakis(triphenylphosphine)palladium(0) (0.03 mmol) in dimethoxyethane (2 mL), sodium carbonate$_{(aq)}$ (2 M, 1.3 mL, 2.6 mmol) and the vial was once again purged with argon. The resultant solution was stirred at room temperature for 5 min when a slurry/solution of pyridin-3-yl-3-boronic acid (199.7 mg, 1.625 mmol) in ethanol (2 mL) was added, the vial was purged with argon, capped, heated to 90° C. and stirred for 1 h. The solution was cooled to room temperature and filtered through a pad of celite (washing with dichloromethane) into a flask containing anhydrous magnesium sulfate (5 g). The solution was dried for 10 min, filtered through filter paper and the solvent was removed in vacuo to afford the crude product which was chromatographed on silica gel.

3-(Thiophen-2-yl)pyridine (7)

The general Suzuki coupling procedure was followed. The crude material was chromatographed on silica gel (EtOAc/Hex, 25/75, $R_f$=0.22) to afford the title compound 7 (130 mg, 62% yield) as a yellow oil: ¹H NMR (CDCl₃) δ 8.88 (m, 1H), 8.51 (m, 1H), 7.87 (m, 1H), 7.37 (m, 2H), 7.31 (m, 1H), 7.13 (m, 1H); LRMS (ESI) m/z calcd for $C_9H_8NS$ [M+H]⁺ 162. found 162; HRMS (ESI) m/z calcd for $C_9H_8NS$ [M+H]⁺ 162.0377. found 162.0378; HPLC>99% ($t_R$=4.60 min, 60 (A):40 (B): 0.05 (C); $t_R$=5.70 min, 60 (A):40 (B): 0.02 (C)).

3-(Thiazol-2-yl)pyridine (8)

The general Suzuki coupling procedure was followed. The crude material was chromatographed on silica gel (EtOAc/Hex, 25/75, $R_f$=0.14) to afford the title compound 8 (146 mg, 70% yield) as a yellow oil that crystallizes in a refrigerator at −40° C.: mp=44-45° C.; ¹H NMR (CDCl₃) δ 9.19 (s, 1H), 8.66 (m, 1H), 8.26 (m, 1H), 7.93 (d, J=3.1 Hz, 1H), 7.42 (d, J=3.2 Hz, 1H), 7.40 (m, 1H); LRMS (ESI) m/z calcd for $C_8H_7N_2S$ [M+H]⁺ 163. found 163; HRMS (ESI) m/z calcd for $C_8H_7N_2S$ [M+H]⁺ 163.0330. found 163.0334; HPLC>99% ($t_R$=5.68 min, 55 (A):45 (B): 0.032 (C); $t_R$=4.52 min, 55 (A):45 (B): 0.1 (C)).

3-(3-Methylthiophen-2-yl)pyridine (9)

The general Suzuki coupling procedure was followed. The crude material was chromatographed on silica gel (EtOAc/Hex, 25/75, $R_f$=0.16) to afford the title compound 9 (197 mg, 87% yield) as a colorless oil: ¹H NMR (CDCl₃) δ 8.73 (m, 1H), 8.55 (m, 1H), 7.75 (m, 1H), 7.34 (m, 1H), 7.27 (d, J=5.2 Hz, 1H), 6.96 (d, J=5.1 Hz, 1H), 2.34 (s, 3H); LRMS (ESI) m/z calcd for $C_{10}H_{10}NS$ [M+H]⁺ 176. found 176; HRMS (ESI) m/z calcd for $C_{10}H_{10}NS$ [M+H]⁺ 176.0534. found 176.0535; HPLC>99% ($t_R$=11.34 min, 55 (A):45 (B): 0.009 (C); $t_R$=4.42 min, 55 (A):45 (B): 0.032 (C)).

2-Fluoro-5-(3-methylthiophen-2-yl)pyridine (10)

The general Suzuki coupling procedure was followed on 1.33 mmol scale. The crude material was chromatographed on silica gel (EtOAc/Hex, 5/95, $R_f$=0.34) to afford the title compound 10 (175 mg, 68% yield) as a colorless oil: ¹H NMR (CDCl₃) δ 8.30 (s, 1H), 7.85 (m, 1H), 7.28 (d, J=5.1 Hz, 1H), 6.98 (m, 1H), 6.96 (d, J=5.1 Hz, 1H), 2.30 (s, 31-1); LRMS (ESI) m/z calcd for $C_{10}H_9FNS$ [M+H]⁺ 194. found 194; HRMS (ESI) m/z calcd for $C_{10}H_9FNS$ [M+H]⁺ 194.0440. found 194.0460; HPLC>96% ($t_R$=41.15 min, 50 (A):50 (D): 0.175 (E); $t_R$=8.83 min, 30 (A):70 (D): 0.105 (E)).

2-Methoxy-5-(3-methylthiophen-2-yl)pyridine (11)

The general Suzuki coupling procedure was followed. The crude material was chromatographed on silica gel (EtOAc/Hex, 5/95, $R_f$=0.30) to afford the title compound 11 (221 mg, 83% yield) as a colorless oil: ¹H NMR (CDCl₃) δ 8.27 (m, 1H), 7.65 (m, 1H), 7.21 (m, 1H), 6.93 (m, 1H), 6.79 (m, 1H), 3.98 (s, 3H), 2.29 (s, 3H); LRMS (ESI) m/z calcd for $C_{11}H_{12}NOS$ [M+H]⁺ 206. found 206; HRMS (ESI) m/z calcd for $C_{11}H_{12}NOS$ [M+H]⁺ 206.0640. found 206.0657; HPLC>99% ($t_R$=3.12 min, 60 (A):40 (B): 0.009 (C); $t_R$=2.62 min, 60 (A):40 (B): 0.02 (C)).

3-Bromo-5-(thiophen-3-yl)pyridine (12)

The general Suzuki coupling procedure was followed. The crude material was chromatographed on silica gel (EtOAc/Hex, 25/75, $R_f$=0.20) to afford the title compound 12 (178 mg, 57% yield) as an orange oil: ¹H NMR (CDCl₃) δ 8.63 (m, 2H), 7.90 (m, 1H), 7.31 (d, J=5.1 Hz, 1H), 6.96 (d, J=5.1 Hz, 1H), 2.34 (s, 3H); LRMS (ESI) m/z calcd for $C_{10}H_9BrNS$ [M+H]⁺ 254. found 254; HRMS (ESI) m/z calcd for $C_{10}H_9BrNS$ [M+H]$^+$ 253.9639. found 253.9623; HPLC>99% ($t_R$=6.01 min, 80 (A):20 (D): 0.7 (E)); 4.47 min, 90 (A):10 (D): 0.035 (E)).

5-(Pyridin-3-yl)thiophene-2-carbaldehyde (13)

The general Suzuki coupling procedure was followed. The crude material was chromatographed on silica gel (EtOAc/Hex, 25/75, $R_f$=0.17) to afford the title compound 13 (224 mg, 91% yield) as a yellow solid: mp=250-254° C. dec.; $^1$H NMR (CDCl$_3$) δ 9.91 (s, 1H), 8.93 (br s, 1H), 8.62 (m, 1H), 7.92 (m, 1H), 7.77 (d, J=4.14 Hz, 1H), 7.45 (d, J=4.14 Hz, 1H), 7.36 (m, 1H); LRMS (ESI) m/z calcd for $C_{10}H_8NOS$ [M+H]$^+$ 190. found 190; HRMS (ESI) m/z calcd for $C_{10}H_8NOS$ [M+H]$^+$ 190.0327. found 190.0343; HPLC>99% ($t_R$=11.37 min, 55 (A):45 (B): 0.009 (C); $t_R$=4.46 min, 45 (A):55 (B): 0.032 (C)).

1-(5-(Pyridin'-3-yl)thiophen-2-yl)ethanone (14)

The general Suzuki coupling procedure was followed. The crude material was chromatographed on silica gel (EtOAc/Hex, 25/75, $R_f$=0.17) to afford the title compound 14 (235 mg, 89% yield) as a yellow solid: mp=104-105° C.; $^1$H NMR (CDCl$_3$) δ 8.93 (br s, 1H), 8.60 (br s, 1H), 7.91 (m, 1H), 7.68 (m, 1H), 7.36 (m, 2H), 2.58 (s, 3H); LRMS (ESI) m/z calcd for $C_{11}H_{10}NOS$ [M+H]$^+$ 204. found 204; HRMS (ESI) m/z calcd for $C_{11}H_{10}NOS$ [M+H]$^+$ 204.0483. found 204.0495; HPLC>99% ($t_R$=7.02 min, 60 (A):40 (B): 0.02 (C); $t_R$=5.06 min, 60 (A):40 (B): 0.07 (C)).

3-(5-Nitrothiophen-2-yl)pyridine (15)

The general Suzuki coupling procedure was followed. The crude material was chromatographed on silica gel (EtOAc/Hex, 25/75, $R_f$=0.17) to afford the title compound 15 (224 mg, 91% yield) as a purple solid: mp=169-171° C.; $^1$H NMR (CDCl$_3$) δ 8.91 (m, 1H), 8.67 (m, 1H), 7.94 (d, J=4.9 Hz, 1H), 7.90 (m, 1H), 7.41 (m, 1H), 7.30 (d, J=4.2 Hz, 1H); LRMS (ESI) m/z calcd for $C_{11}H_7N_2O_2S$ [M+H]$^+$ 207. found 207; HRMS (ESI) m/z calcd for $C_9H_7N_2O_2S$ [M+H]$^+$ 207.0228. found 207.0249; HPLC>99% ($t_R$=5.12 min, 55 (A):45 (B): 0.032 (C); $t_R$=4.13 min, 45 (A):55 (B): 0.1 (C)).

3-(Thiophen-3-yl)pyridine (16)

The general Suzuki coupling procedure was followed. The crude material was chromatographed on silica gel (EtOAc/Hex, 25/75, $R_f$=0.18) to afford the title compound 16 (224 mg, 91% yield) as a yellow solid: mp=75-77° C.; $^1$H NMR (CDCl$_3$) δ 8.88 (br s, 1H), 8.53 (m, 1H), 7.87 (m, 1H), 7.52 (m, 1H), 7.44 (m, 1H), 7.40 (m, 1H), 7.32 (m, 1H); LRMS (ESI) m/z calcd for $C_9H_8NS$ [M+H]$^+$ 162. found 162; HRMS (ESI) m/z calcd for $C_9H_8NS$ [M+H]$^+$ 162.0377. found 162.0375; HPLC>99% ($t_R$=12.45 min, 55 (A):45 (B): 0.009 (C); $t_R$=4.52 min, 55 (A):45 (B): 0.032 (C)).

2-Fluoro-5-(thiophen-3-yl)pyridine (17)

The general Suzuki coupling procedure was followed. The crude material was chromatographed on silica gel (EtOAc/Hex, 2.5/97.5, $R_f$=0.21) to afford the title compound 17 (110 mg, 77% yield) as a colorless oil: $^1$H NMR (CDCl$_3$) δ 8.44 (m, 1H), 7.96 (m, 1H), 7.45 (m, 2H), 7.34 (m, 1H), 6.97 (m, 1H); LRMS (ESI) m/z calcd for $C_9H_7FNS$ [M+H]$^+$ 180. found 180; HRMS (ESI) m/z calcd for $C_9H_7FNS$ [M+H]$^+$ 180.0283. found 180.0278; HPLC>98% ($t_R$=8.22 min, 60 (A):40 (D): 0.140 (E); $t_R$=4.59 min, 30 (A):70 (D): 0.105 (E)).

2-Methoxy-5-(thiophen-3-yl)pyridine (18)

The general Suzuki coupling procedure was followed. The crude material was chromatographed on silica gel (EtOAc/Hex, 2.5/97.5, $R_f$=0.17) to afford the title compound 18 (217 mg, 87% yield) as a colorless oil: $^1$H NMR (CDCl$_3$) δ 8.41 (m, 1H), 7.78 (m, 1H), 7.42-7.26 (m, 3H), 6.79 (m, 1H), 3.97 (s, 3H); LRMS (ESI) m/z calcd for $C_{10}H_{10}NOS$ [M+H]$^+$ 192. found 192; HRMS (ESI) m/z calcd for $C_{10}H_{10}NOS$ [M+H]$^+$ 192.0483. found 192.0478; HPLC>99% ($t_R$=4.65 min, 60 (A):40 (B): 0.009 (C); $t_R$=3.73 min, 60 (A):40 (B): 0.02 (C)).

3-Bromo-5-(3-methylthiophen-2-yl)pyridine (19)

The general Suzuki coupling procedure was followed. The crude material was chromatographed on silica gel (EtOAc/Hex, 2.5/97.5, $R_f$=0.20) to afford the title compound 19 (175 mg, 53% yield) as a white solid: mp=58-59° C.; $^1$H NMR (CDCl$_3$) δ 8.77 (m, 1H), 8.59 (m, 1H), 8.02 (m, 1H), 7.55 (m, 1H), 7.46 (m, 1H), 7.37 (m, 1H); LRMS (ESI) m/z calcd for $C_9H_7BrNS$ [M+H]$^+$ 240. found 240; HRMS (ESI) m/z calcd for $C_9H_7BrNS$ [M+H]$^+$ 239.9483. found 239.9467; HPLC>99% ($t_R$=3.56 min, 60 (A):40 (B): 0.02 (C); $t_R$=2.68 min, 55 (A):45 (B): 0.01 (C)).

3-(4-Methylthiophen-3-yl)pyridine (20)

The general Suzuki coupling procedure was followed. The crude material was chromatographed on silica gel (EtOAc/Hex, 25/75, $R_f$=0.24) to afford the title compound 16 (191 mg, 84% yield) as a yellow oil: $^1$H NMR (CDCl$_3$) δ 8.66 (m, 1H), 8.57 (m, 1H), 7.70 (m, 1H), 7.33 (m, 1H), 7.26 (m, 1H), 7.01 (m, 1H), 2.27 (s, 3H); LRMS (ESI) m/z calcd for $C_{10}H_{10}NS$ [M+H]$^+$ 176. found 176; HRMS (ESI) m/z calcd for $C_{10}H_{10}NS$ [M+H]$^+$ 176.0534. found 176.0538; HPLC>99% ($t_R$=4.31 min, 55 (A):45 (B): 0.032 (C); $t_R$=3.57 min, 55 (A):45 (B): 0.1 (C)).

2-Fluoro-5-(4-methylthiophen-3-yl)pyridine (21)

The general Suzuki coupling procedure was followed. The crude material was chromatographed on silica gel (EtOAc/Hex, 2.5/97.5, $R_f$=0.22) to afford the title compound 21 (121 mg, 78% yield) as a colorless oil: $^1$H NMR (CDCl$_3$) δ 8.24 (m, 1H), 7.79 (m, 1H), 7.24 (m, 1H), 7.07 (m, 1H), 6.98 (m, 1H), 2.25 (s, 3H); LRMS (ESI) m/z calcd for $C_{10}H_9FNS$ [M+H]$^+$ 194. found 194; HRMS (ESI) m/z calcd for $C_{10}H_9FNS$ [M+H]$^+$ 194.0425. found 194.0460; HPLC>99% ($t_R$=15.28 min, 60 (A):40 (D): 0.14 (E); $t_R$=8.62 min, 30 (A):70 (D): 0.105 (E)).

2-Methoxy-5-(4-methylthiophen-3-yl)pyridine (22)

The general Suzuki coupling procedure was followed. The crude material was chromatographed on silica gel (EtOAc/Hex, 10/90, $R_f$=0.42) to afford the title compound 22 (265 mg, 99% yield) as a white semisolid: $^1$H NMR (CDCl$_3$) δ 8.20 (m, 1H), 7.61 (m, 1H), 7.18 (m, 1H), 7.04 (m, 1H), 6.80 (m, 1H), 3.98 (s, 3H), 2.25 (s, 3H); LRMS (ESI) m/z calcd for $C_{11}H_{12}ONS$ [M+H]$^+$ 206. found 206; HRMS (ESI) m/z calcd for $C_{11}H_{12}ONS$ [M+H]$^+$ 206.0640. found 206.0633;

HPLC>99% ($t_R$=3.69 min, 55 (A):45 (B): 0.009 (C); $t_R$=3.37 min, 55 (A):45 (B): 0.032 (C)).

5-(Pyridin-3-yl)furan-2-carbaldehyde (23)

The general Suzuki coupling procedure was followed. The crude material was chromatographed on silica gel (EtOAc/Hex, 50/50, $R_f$=0.19) to afford the title compound 23 (1.28 g, 95% yield) as an off white solid. Analytical properties are consistent with published values: mp=112-115° C., (Lit. 113-115° C.) (Gauthier et al., *Org. Lett.* 4L375-378 (2002)); $^1$H NMR (CDCl$_3$) δ 9.70 (s, 1H), 9.05 (m, 1H), 8.63 (m, 1H), 8.12 (m, 1H), 7.39 (m, 1H), 7.35 (d, J=4.1 Hz, 1H), 6.94 (d, J=4.1 Hz, 1H).

2-(Pyridin-3-yl)pyridine (24)

The general Suzuki coupling procedure was followed. The crude material was chromatographed on silica gel (EtOAc/Hex, 50/50, $R_f$=0.12) to afford the title compound 24 (141 mg, 70% yield) as a colorless oil. Analytical properties are consistent with those obtained for a commercial sample.

3-Methyl-2-(pyridin-3-yl)pyridine (25)

The general Suzuki coupling procedure was followed. The crude material was chromatographed on silica gel (EtOAc/Hex, 50/50, $R_f$=0.07) to afford the title compound 25 (94 mg, 43% yield) as a yellow semisolid: $^1$H NMR (CDCl$_3$, 500 MHz) δ 8.77 (m, 1H), 8.61 (m, 1H), 8.52 (m, 1H), 7.85 (m, 1H), 7.59 (m, 1H), 7.36 (m, 1H), 7.20 (m, 1H), 2.35 (s, 3H); LRMS (ESI) m/z calcd for C$_{11}$H$_{11}$N$_2$ [M+H]$^+$ 171. found 171; HRMS (ESI) m/z calcd for C$_{11}$H$_{11}$N$_2$ [M+H]$^+$ 171.0922. found 171.0908; HPLC>99% ($t_R$=10.72 min, 55 (A):45 (B): 0.032 (C); ($t_R$=9.61 min, 60 (A):40 (B): 0.002 (C)).

4-Methyl-2-(pyridin-3-yl)pyridine (26)

The general Suzuki coupling procedure was followed. The crude material was chromatographed on silica gel (EtOAc/Hex, 50/50, $R_f$=0.12) to afford the title compound 26 (180 mg, 81% yield) as a yellow oil: $^1$H NMR (CDCl$_3$, 500 MHz) 9.16 (br s, 1H), 8.64 (m, 1H), 8.57 (m, 1H), 8.30 (m, 1H), 7.56 (m, 1H), 7.40 (m, 1H), 7.12 (m, 1H), 2.43 (s, 3H); LRMS (ESI) m/z calcd for C$_{11}$H$_{11}$N$^2$ [M+H]$^+$ 171. found 171; HRMS (ESI) m/z calcd for C$_{11}$H$_{11}$N$_2$ [M+H]$^+$ 171.0922. found 171.0939; HPLC>99% ($t_R$=8.11 min, 60 (A):40 (B): 0.02 (C); $t_R$=6.74 min, 60 (A):40 (B): 0.07 (C)).

5-Methyl-2-(pyridin-3-yl)pyridine (27)

The general Suzuki coupling procedure was followed. The crude material was chromatographed on silica gel (EtOAc/Hex, 50/50, $R_f$=0.11) to afford the title compound 27 (167 mg, 76% yield) as a yellow solid: mp=40-41° C., $^1$H NMR (CDCl$_3$, 500 MHz) 9.16 (m, 1H), 8.62 (m, 1H), 8.55 (m, 1H), 8.29 (m, 1H), 7.65 (m, 1H), 7.59 (m, 1H), 7.39 (m, 1H), 2.39 (s, 3H); LRMS (ESI) m/z calcd for C$_{11}$H$_{11}$N$_2$ [M+H]$^+$ 171. found 171; HRMS (ESI) m/z calcd for C$_{11}$H$_{11}$N$_2$ [M+H]$^+$ 171.0922. found 171.0939; HPLC>99% ($t_R$=7.78 min, 60 (A):40 (B): 0.02 (C); $t_R$=6.32 min, 60 (A):40 (B): 0.07 (C)).

2-Methyl-6-(pyridin-3-yl)pyridine (28)

The general Suzuki coupling procedure was followed. The crude material was chromatographed on silica gel (EtOAc/Hex, 50/50, $R_f$=0.19) to afford the title compound 28 (144 mg, 65% yield) as a yellow oil: $^1$H NMR (CDCl$_3$, 500 MHz) 9.17 (m, 1H), 8.63 (m, 1H), 8.32 (m, 1H), 7.68 (m, 1H), 7.54 (m, 1H), 7.39 (m, 1H), 7.15 (m, 1H), 2.64 (s, 3H); LRMS (ESI) m/z calcd for C$_{11}$H$_{11}$N$_2$ [M+H]$^+$ 171. found 171; HRMS (ESI) m/z calcd for C$_{11}$H$_{11}$N$_2$ [M+H]$^+$ 171.0922. found 171.0939; HPLC>99% ($t_R$=8.58 min, 60 (A):40 (B): 0.02 (C); $t_R$=6.70 min, 60 (A):40 (B): 0.07 (C)).

2-(Pyridin-3-yl)pyrimidine (29)

The general Suzuki coupling procedure was followed. The crude material was chromatographed on silica gel (EtOAc/Hex, 25/75, $R_f$=0.07) to afford the title compound 29 (108 mg, 53% yield) as an orange solid: mp=51-52° C.; $^1$H NMR (CDCl$_3$) δ 9.64 (s, 1H), 8.83 (m, 2H), 8.70 (m, 2H), 7.41 (m, 1H), 7.24 (m, 1H); LRMS (ESI) m/z calcd for C$_9$H$_8$N$_3$ [M+H]$^+$ 158. found 158; HRMS (ESI) m/z calcd for C$_9$H$_8$N$_3$ [M+H]$^+$ 158.0718. found 158.0706; HPLC>99% ($t_R$=5.91 min, 55 (A):45 (B): 0.032 (C); $t_R$=4.82 min, 55 (A):45 (B): 0.1 (C)).

5-(Pyridin-3-yl)pyrimidine (30)

The general Suzuki coupling procedure was followed. The crude material was chromatographed on silica gel (EtOAc/Hex, 25/75, $R_f$=0.08) to afford the title compound 30 (167 mg, 82% yield) as a white solid: mp=101-103° C.; $^1$H NMR (CDCl$_3$) δ 9.27 (s, 1H), 8.97 (s, 2H), 8.85 (m, 1H), 8.71 (m, 1H), 7.90 (m, 1H), 7.46 (m, 1H); LRMS (ESI) m/z calcd for C$_9$H$_8$N$_3$ [M+H]$^+$ 158. found 158; HRMS (ESI) m/z calcd for C$_9$H$_8$N$_3$ [M+H]$^+$ 158.0718. found 158.0706; HPLC>99% ($t_R$=5.91 min, 55 (A):45 (B): 0.032 (C); $t_R$=4.82 min, 55 (A):45 (B): 0.1 (C)).

3-(Pyridin-3-yl)pyridine (31)

The general Suzuki coupling procedure was followed. The crude material was chromatographed on silica gel (EtOAc/Hex, 75/25, $R_f$=0.14) to afford the title compound 31 (182 mg, 90% yield) as a yellow oil: $^1$H NMR (CDCl$_3$, 500 MHz) δ 8.84 (m, 2H), 8.64 (m, 2H), 7.87 (m, 2H), 7.40 (m, 2H); LRMS (ESI) m/z calcd for C$_{10}$H$_9$N$_2$ [M+H]$^+$ 157. found 157; HRMS (ESI) m/z calcd for C$_{10}$H$_9$N$_2$ [M+H]$^+$ 157.0766. found 157.0775; HPLC>99% ($t_R$=3.73 min, 55 (A):45 (B): 0.1 (C); $t_R$=20.4 min, 55 (A):45 (B): 0.032 (C)).

3-(6-Chloropyridin-3-yl)pyridine (32)

The general Suzuki coupling procedure was followed. The crude material was chromatographed on silica gel(EtOAc/Hex, 50/50, $R_f$=0.22) to afford the title compound 32 (123 mg, 49% yield) as an off white solid: mp=113-115° C.; $^1$H NMR (CDCl$_3$, 500 MHz) δ 8.82 (m, 1H), 8.68 (m, 1H), 8.61 (m, 1H), 7.86 (m, 2H), 7.43 (m, 2H); LRMS (ESI) m/z calcd for C$_{10}$H$_8$ClN$_2$ [M+H]$^+$ 191. found 191; HRMS (ESI) m/z calcd for C$_{10}$H$_8$ClN$_2$ [M+H]$^+$ 191.0376. found 191.0372; HPLC>99% ($t_R$=7.23 min, 60 (A):40 (B): 0.02 (C); $t_R$=5.48 min, 60 (A):40 (B): 0.07 (C)).

3-(Pyridin-3-yl)quinoline (33)

The general Suzuki coupling procedure was followed. The crude material was chromatographed on silica gel (EtOAc/Hex, 25/75, $R_f$=0.07) to afford the title compound 33 (200 mg, 75% yield) as a white solid: mp=117-119° C.; $^1$H NMR. (CDCl$_3$, 500 MHz) δ 9.16 (s, 1H), 8.99 (s, 1H), 8.70 (m, 1H), 8.34 (s, 1H), 8.17 (m, 1H), 8.02 (m, 1H), 7.92 (m, 1H), 7.77

(m, 1H), 7.62 (m, 1H), 7.47 (m, 1H); LRMS (ESI) m/z calcd for $C_{14}H_{11}N_2$ [M+H]$^+$ 207. found 207; HRMS (ESI) m/z calcd for $C_{14}H_{11}N_2$ [M+H]$^+$ 207.0922. found 207.0902; HPLC>99% ($t_R$=18.01 min, 55 (A):45 (B): 0.009 (C); $t_R$=10.17 min, 55 (A):45 (B): 0.1 (C)).

3-(1H-Imidazol-4-yl)pyridine (34)

The general Suzuki coupling procedure was followed with the following exception: the reaction required 14 h to reach completion as determined by TLC analysis. The crude material was chromatographed on silica gel ($CH_3OH/CHCl_3$, 10/90, $R_f$=0.18) to afford the title compound 34 (74 mg, 39% yield) as an off white oil: $^1$H NMR (CDCl$_3$) δ 8.99 (m, 1H), 8.47 (m, 1H), 8.09 (m, 1H), 7.76 (d, J=1.1 Hz, 1H), 7.43 (d, J=1.1 Hz, 1H), 7.33 (m, 1H), 7.12 (d, J=1.1 Hz, 1H); LRMS (ESI) m/z calcd for $C_8H_8N_3$ [M+H]$^+$ 146. found 146; HRMS (ESI) m/z calcd for $C_8H_8N_3$ [M+H]$^+$ 146.0718. found 146.0729; HPLC>99% ($t_R$=7.68 min, 55 (A):45 (B): 0.032 (C); $t_R$=4.40 min, 55 (A):45 (B): 0.1 (C)).

3-(2-Methyl-1H-imidazol-4-yl)pyridine (35)

The general Suzuki coupling procedure was followed. The crude material was chromatographed on silica gel ($CH_3OH/CHCl_3$, 10/90, $R_f$=0.25) to afford the title compound 35 (138 mg, 67% yield) as a yellow oil that partially solidifies in the freezer: $^1$H NMR (CDCl$_3$) δ 8.94 (m, 1H), 8.43 (m, 1H), 8.04 (m, 1H), 7.28 (m, 2H), 2.46 (s, 3H); LRMS (ESI) m/z calcd for $C_9H_{10}N_3$ [M+H]$^+$ 160. found 160; HRMS (ESI) m/z calcd for $C_9H_{10}N_3$ [M+H]$^+$ 160.0875. found 160.0870; HPLC>99% ($t_R$=8.76 min, 60 (A):40 (B): 0.02 (C); $t_R$=5.97 min, 60 (A):40 (B): 0.07 (C)).

Cis/trans 5-(pyridin-3-yl)thiophene-2-carbaldehyde oximes (36)

To a solution of 14 (214 mg, 1.13 mmol) in 95% ethanol (10 mL) was added hydroxylamine hydrochloride (86 mg, 1.24 mmol) and sodium acetate (102 mg, 1.24 mmol), the resultant slurry was heated to reflux and stirred for 25 min. The solvent was removed in vacuo and the residue was dissolved in MeOH and absorbed to silica gel. The solvent was removed in vacuo and the material was chromatographed on silica gel ($CH_3OH/CHCl_3$, 5/95, $R_f$=0.23) to afford the cis/trans mixture of the title compound 36 as a yellow solid: mp=178-185° C. dec.; $^1$H NMR (CDCl$_3$) δ 9.17 (m, 0.75H), 8.93 (m, 0.25H) 8.55 (m, 0.25H), 8.50 (m, 0.75H), 8.29 (s, 0.75H) 7.98-7.90 (m, 1H), 7.39-7.31 (m, 2.5H), 7.15 (m, 0.7511); LRMS (ESI) m/z calcd for $C_{10}H_9N_2OS$ [M+H]$^+$ 205. found 205; HRMS (ESI) m/z calcd for $C_{10}H_9N_2OS$ [M+H]$^+$ 205.0436. found 205.0455; HPLC>99% ($t_R$=3.90 min, 55 (A):45 (B): 0.032 (C); $t_R$=4.34 min, 45 (A):55 (B): 0.1 (C)).

Cis/trans 5-(pyridin-3-yl)furan-2-carbaldehyde oximes (37a, 37b)

To a solution of 23 (106 mg, 0.61 mmol) in 95% ethanol (6 mL) was added hydroxylamine hydrochloride (69 mg, 0.68 mmol) and sodium acetate (55 mg, 0.68 mmol). The resultant slurry was heated to reflux and stirred for 75 min, cooled and the solid was removed by filtration and the solvent was removed in vacuo. The crude oil was triturated with ethyl ether and the solid was collected by filtration to afford the cis/trans mixture 37a, b (17 mg, 15%): HPLC>99% ($t_R$=5.16, 5.45 min, 60 (A):40 (B): 0.02 (C); $t_R$=7.5, 7.92 min, 60 (A):40 (B): 0.009 (C)). The mother liquor was chromatographed on silica gel (EtOAc/Hex, 50/50) to afford the cis isomer 37a ($R_f$=0.21, 37 mg, 32%) as a white solid: mp=143-150° C. dec., $^1$H NMR (CD$_3$OD) δ 9.93 (m, 1H, H$_2$), 9.42 (m, 1H, H$_6$), 9.16 (m, 1H, H$_4$), 9.01 (s, 1H, HC=N), 8.46 (m, 1H, H$_5$), 8.02 (d, J=3.7 Hz, 1H, H$_3$'), 7.77 (d, J=3.7 Hz, 1H, H$_4$'); HPLC>99% ($t_R$=5.25 min, 60 (A):40 (B): 0.02 (C); $t_R$=8.67 min, 60 (A):40 (B) 0.009 (C)); and the trans isomer 37b ($R_f$=0.36, 44 mg, 38%) as a white semisolid: $^1$H NMR (CD$_3$OD) δ 9.91 (m, 1H, H$_2$), 9.94 (m, 1H, H$_6$), 9.14 (m, 1H, H$_4$), 8.50 (s, 1H, HC=N), 8.46 (m, 1H, H$_5$), 8.35 (d, J=3.7 Hz, 1H, H$_3$'), 8.07 (d, J=3.7 Hz, 1H, H$_4$'); HPLC>99% ($t_R$=4.07 min, 60 (A):40 (B): 0.05 (C); $t_R$=7.51 min, 60 (A):40 (B): 0.009 (C)); LRMS (ESI) m/z calcd for $C_{10}H_9N_2O_2$ (33a, b mixture) [M+H]$^+$189. found 189; HRMS (ESI) m/z calcd for $C_{10}H_9N_2O_2$ (33a, b mixture) [M+H]$^+$ 189.0664. found 189.0677.

(5-(Pyridin-3-yl)thiophen-2-yl)methanamine (38a) and bis((5-(pyridin-3-yl)thiophen-2-yl)methyl)amine (38b)

To a solution of 14 (122 mg, 0.68 mmol) in absolute methanol (4 mL) was added ammonium acetate (520 mg, 6.75 mmol) followed by sodium cyanoborohydride (30 mg, 0.47 mmol) and the resultant solution was stirred at room temperature under argon for 18 h. The reaction was quenched by the addition of glacial acetic acid (1 mL), stirred for 5 min and subsequently poured into a stirred solution of NaOH$_{(aq)}$ (1 N, 20 mL), extracted with ethyl acetate (3×25 mL), dried (MgSO$_4$) and filtered. The solvent was removed in vacuo and the residue was chromatographed on silica gel ($CH_3OH/CHCl_3$, 5/95, $R_f$=0.28) to afford the title compound 38b (34 mg, 27% yield) as an orange semi-solid: $^1$H NMR (CDCl$_3$) δ 8.86 (s, 1H), 8.50 (m, 1H), 7.84 (m, 1H), 7.29 (m, 1H), 7.23 (d, J=3.1 Hz, 1H), 6.96 (d, J=4.1 Hz, 1H), 4.07 (s, 2H), 1.84 (br s, 1H); LRMS (ESI) m/z calcd for $C_{20}H_{18}N_3S_2$ [M+H]$^+$ 364. found 364; HRMS (ESI) m/z calcd for $C_{20}H_{18}N_3S_2$ [M+H]$^+$ 364.0942. found 364.0978; HPLC>98% ($t_R$=28.16 min, 55 (A):45 (B): 0.032 (C); $t_R$=12.09 min, 55 (A):45 (B): 0.1 (C)).

Later fractions ($R_f$=0.08) afforded the title compound 38a (14 mg, 11% yield) as an orange solid: mp=170-172° C.; NMR (CDCl$_3$) δ 8.85 (s, 1H), 8.50 (m, 1H), 7.82 (m, 1H), 7.29 (m, 1H), 7.21 (d, J=3.1 Hz, 1H), 6.92 (d, J=4.1 Hz, 1H), 4.09 (s, 2H), 1.65 (br s, 2H); LRMS (ESI) m/z calcd for $C_{10}H_{11}N_2S$ [M+H]$^+$ 191. found 191; HRMS (ESI) m/z calcd for $C_{10}H_{11}N_2S$ [M+H]$^+$ 191.0643. found 191.0650; HPLC>98% ($t_R$=12.42 min, 55 (A):45 (B): 0.032 (C); $t_R$=3.26 min, 75 (A):25 (B): 0.05 (C)).

(5-(Pyridin-3-yl)furan-2-yl)methanamine,bis((5-(pyridin-3-yl)furan-2-yl)methyl)amine and tris((5-(pyridin-3-yl)furan-2-yl)methyl)amine (39a, b, c)

To a solution of 23 (106 mg, 0.61 mmol) in absolute methanol (5 mL) was added ammonium acetate (473 mg, 6.13 mmol) followed by sodium cyanoborohydride (27 mg, 0.43 mmol) and the resultant solution was stirred at room temperature under argon for 48 h. The solution was adjusted to pH 2 with conc. HCl and the solvent was removed in vacuo. The residue was dissolved in water and washed with Et$_2$O (2×20 mL). The aqueous portion was adjusted to pH 10 with 10 N NaOH and extracted with Et$_2$O (3×50 mL), dried (MgSO$_4$), filtered and the solvent was removed in vacuo. The crude material was chromatographed on silica gel ($CH_3OH/CHCl_3$, 10/90, $R_f$=0.45) to afford the title compound 39 (44 mg, 44% yield) as an off white solid: mp=170-172° C.; NMR (CDCl$_3$)

δ 8.92 (br s, 3H), 8.47 (m, 3H), 7.91 (m, 3H), 7.27 (m, 3H), 6.70 (d, J=3.2 Hz, 3H), 6.41 (d, J=3.3 Hz, 3H), 4.07 (s, 6H); LRMS (ESI) m/z calcd for $C_{30}H_{24}N_4O_3$ [M+H]$^+$ 489. found 489; HRMS (ESI) m/z calcd for $C_{30}H_{24}N_4O_3$ [M+H]$^+$ 489.1927. found 489.1956; HPLC>99% ($t_R$=8.82 min, 60 (A):40 (B): 0.05 (C); $t_R$=4.64 min, 80 (A):20 (B): 0.1 (C).

Later fractions ($R_f$=0.41) afforded the title compound 39b (29 mg, 28% yield) as an orange solid: mp=170-172° C.; NMR (CDCl$_3$) δ 8.90 (s, 2H), 8.47 (m, 2H), 7.90 (m, 2H), 7.28 (m, 2H), 6.68 (m, 2H), 6.34 (m, 2H), 3.92 (s, 4H), 2.09 (br s, 1H); LRMS (ESI) m/z calcd for $C_{20}H_{17}N_3O_2$ [M+H]$^+$ 332. found 332; HRMS (ESI) m/z calcd for $C_{10}H_{11}N_2S$ [M+H]$^+$ 332.1399. found 332.1418; HPLC>98% ($t_R$=5.69 min, 70 (A):30 (B): 0.05 (C); $t_R$=3.51 min, 80 (A):20(13): 0.1 (C)).

Later fractions ($R_f$=0.14) afforded the title compound 39a (23 mg, 22% yield) as a yellow oil which solidified upon cooling in a refrigerator: $^1$H NMR (CDCl$_3$) δ 8.90 (m, 1H), 8.47 (m, 1H), 7.90 (m, 1H), 7.29 (m, 1H), 6.67 (d, J=3.2 Hz, 1H), 6.26 (d, J=3.2 Hz, 1H), 3.91 (s, 2H), 1.66 (br s, 2H); LRMS (ESI) m/z calcd for $C_{10}H_{11}N_2O$ [M+H]$^+$ 175. found 175; HRMS (ESI) m/z calcd for $C_{10}H_{11}N_2O$ [M+H]$^+$ 175.0871. found 175.0872; HPLC>95% ($t_R$=7.60 min, 55 (A):45 (B): 0.009 (C); $t_R$=3.76 min, 75 (A):25 (B): 0.05 (C)).

N-Methyl(5-(pyridin-3-yl)thiophen-2-yl)methanamine (40)

To a solution 13 (90 mg, 0.48 mmol) was added a solution of methylamine (2.0 M, 1.43 mL, 2.85 mmol) in anhydrous CH$_3$OH, a solution of HCl (4.0 M, 0.24 mL, 0.95 mmol) in anhydrous 1,4-dioxane and sodium cyanoborohydride (30 mg, 0.48 mmol). The flask was purged with argon and stirred under an atmosphere of argon at room temperature for 24 h. The solution was adjusted to pH 2 with conc. HCl and the solvent was removed in vacuo. The residue was dissolved in water and washed with Et$_2$O (3×10 mL). The aqueous fraction was adjusted to pH 10 with NaOH$_{(aq)}$ (10 N), extracted with Et$_2$O (3×20 mL), dried (Na$_2$SO$_4$), filtered and the solvent was removed in vacuo. The crude material was chromatographed on silica gel (CH$_3$OH/CHCl$_3$, 10/90, $R_f$=0.13) to afford the title compound 40 (39 mg, 40% yield) as a yellow oil: $^1$H NMR (CDCl$_3$) δ 8.84 (m, 1H), 8.49 (m, 1H), 7.82 (m, 1H), 7.28 (m, 1H), 7.21 (d, J=3.6 Hz, 1H), 6.93 (d, J=3.5 Hz, 1H), 3.96 (s, 2H)$_{2.31}$ (s, 3H); LRMS (ESI) m/z calcd for $C_{11}H_{13}N_2S$ [M+H]$^+$ 205. found 205; m/z calcd for $C_{10}H_8NS$ [M-NH(CH$_3$)]$^+$ 174. found 174; HRMS (ESI) m/z calcd for $C_{11}H_{13}N_2S$ [M+H]$^+$ 205.0799. found 205.0781; HPLC>95%=4.34 min, 80 (A):20 (B): 0.05 (C); $t_R$=3.60 min, 60 (A):40 (B): 0.07 (C)).

N-Methyl(5-(pyridin-3-yl)furan-2-yl)methanamine (41)

To a solution 23 (104 mg, 0.60 mmol) was added a solution of methylamine (2.0 M, 1.8 mL, 3.6 mmol) in anhydrous CH$_3$OH, a solution of HCl (4.0 M, 0.3 mL, 1.2 mmol) in anhydrous 1,4-dioxane and sodium cyanoborohydride (38 mg, 0.6 mmol). The flask was purged with argon and stirred under an atmosphere of argon at room temperature for 48 h. The solution was adjusted to pH 2 with conc. HCl and the solvent was removed in vacuo. The residue was dissolved in water, washed with Et$_2$O (3×10 mL), adjusted to pH 10 with NaOH$_{(aq)}$ (10 N), extracted with Et$_2$O (3×20 mL), dried (Na$_2$SO$_4$), filtered and the solvent was removed in vacuo. The crude material was chromatographed on silica gel (CH$_3$OH/CHCl$_3$, 10/90, $R_f$=0.1) to afford the title compound 41 (94 mg, 84% yield) as a yellow oil: $^1$H NMR (CDCl$_3$) δ 8.89 (m, 1H), 8.46 (m, 1H), 7.91 (m, 1H), 7.28 (m, 1H), 6.67 (d, J=3.2 Hz, 1H), 6.31 (d, J=3.2 Hz, 1H), 3.82 (s, 2H), 2.49 (s, 3H), 2.14 (br s, 1H); LRMS (ESI) m/z calcd for $C_{11}H_{13}N_2O$ [M+H]$^+$ 189. found 189; m/z calcd for $C_{10}H_8NO$ [M-NH(CH$_3$)]$^+$ 158. found 158; HRMS (ESI) m/z calcd for $C_{11}H_{13}N_2O$ [M+H]$^+$ 189.1028. found 189.1041; HPLC>95% ($t_R$=8.74 min, 60 (A):40 (B): 0.02 (C); $t_R$=3.69 min, 60 (A):40 (B): 0.07 (C)).

N,N-Dimethyl(5-(pyridin-3-yl)thiophen-2-yl)methanamine (42)

To a solution of 13 (90 mg, 0.48 mmol) was added a solution of dimethylamine (2.9 M, 0.99 mL, 2.85 mmol) in anhydrous CH$_3$OH, a solution of HCl (4.0 M, 0.24 mL, 0.95 mmol) in anhydrous 1,4-dioxane and sodium cyanoborohydride (30 mg, 0.48 mmol). The flask was purged with argon and stirred under an atmosphere of argon at room temperature for 24 h. The solution was adjusted to pH 2 with conc. HCl and the solvent was removed in vacuo. The residue was dissolved in water, washed with Et$_2$O (3×10 mL), adjusted to pH 10 with NaOH$_{(aq)}$ (10 N), extracted with Et$_2$O (3×20 mL), dried (Na$_2$SO$_4$), filtered and the solvent was removed in vacuo. The crude material was chromatographed on silica gel (CH$_3$OH/CHCl$_3$, 2.5/97.5, $R_f$=0.15) to afford the title compound 42 (57 mg, 55% yield) as a yellow oil: $^1$H NMR (CDCl$_3$) δ 8.85 (br s, 1H), 8.48 (m, 1H), 7.82 (m, 1H), 7.28 (m, 1H), 7.21 (d, J=3.7 Hz, 1H), 6.91 (d, J=3.5 Hz, 1H), 3.65 (s, 2H) 2.31 (s, 6H); LRMS (ESI) m/z calcd for $C_{12}H_{15}N_2S$ [M+H]$^+$ 219. found 219; m/z calcd for $C_{10}H_8NS$ [M-N(CH$_3$)$_2$]$^+$ 174. found 174; HRMS (ESI) m/z calcd for $C_{12}H_{15}N_2S$ [M+H]$^+$ 219.0956. found 219.0955; HPLC>99% ($t_R$=8.90 min, 55 (A):45 (B): 0.009 (C); $t_R$=6.28 min, 55 (A):45 (B): 0.018 (C)).

N,N-Dimethyl(5-(pyridin-3-yl)furan-2-yl)methanamine (43)

To a solution of 23 (54 mg, 0.31 mmol) was added a solution of dimethylamine (2.9 M, 0.65 mL, 1.89 mmol) in anhydrous CH$_3$OH, a solution of HCl (4.0 M, 0.16 mL, 0.63 mmol) in anhydrous 1,4-dioxane and sodium cyanoborohydride (20 mg, 0.31 mmol). The flask was purged with argon and stirred under an atmosphere of argon at room temperature for 48 h. The solution was adjusted to pH 2 with conc. HCl and the solvent was removed in vacuo. The residue was dissolved in water, washed with Et$_2$O (3×10 mL), adjusted to pH 10 with NaOH$_{(aq)}$ (10 N), extracted with Et$_2$O (3×20 mL), dried (Na$_2$SO$_4$), filtered and the solvent was removed in vacuo. The crude material was chromatographed on silica gel (CH$_3$OH/CHCl$_3$, 5/95, $R_f$=0.2) to afford the title compound 43 (23 mg, 37% yield) as a yellow oil: $^1$H NMR (CDCl$_3$) δ 8.91 (m, 1H), 8.46 (m, 1H), 7.94 (m, 1H), 7.28 (m, 1H), 6.68 (d, J=3.3 Hz, 1H), 6.32 (d, J=3.4 Hz, 1H), 2.31 (s, 6H); LRMS (ESI) m/z calcd for $C_{12}H_{15}N_2O$ [M+H]$^+$ 203. found 203; m/z calcd for $C_{10}H_8NO$ [M-N(CH$_3$)$_2$]$^+$ 158. found 158; HRMS (ESI) m/z calcd for $C_{12}H_{15}N_2O$ [M+H]$^+$ 203.1184. found 203.1205; HPLC>99% ($t_R$=6.00 min, 60 (A):40 (B): 0.07 (C); $t_R$=5.10 min, 60 (A):40 (B): 0.1 (C)).

(5-(Pyridin-3-yl)thiophen-2-yl)methanol (44)

To a solution of 13 (116 mg, 0.61 mmol) in CH$_3$OH (5 mL) was added sodium borohydride (23 mg, 0.61 mmol) in one portion. The resultant solution was stirred at room temperature for 10 min, stopped by the addition of aqueous sodium bicarbonate (50:50 satd. soln./water, v:v) and the solvent was removed in vacuo. The residue was partitioned between water (50 mL) and EtOAc (50 mL). The organic layer was collected and the aqueous was extracted with EtOAc (2×50 mL). The combined organic extracts were dried (MgSO$_4$) and the solvent was removed in vacuo to afford the title compound 44 (116 mg, 99% yield) as an off white solid: mp=89-90° C.; $^1$H NMR (CDCl$_3$) δ 8.82 (m, 1H), 8.49 (m, 1H), 7.84 (m, 1H), 7.31 (m, 1H), 7.22 (d, J=4.1 Hz, 1H), 7.01 (d, J=4.1 Hz, 1H), 4.85 (s, 2H); LRMS (ESI) m/z calcd for C$_{11}$H$_{10}$NOS [M+H]$^+$ 192. found 192; HRMS (ESI) m/z calcd for C$_{10}$H$_{10}$NOS [M+H]$^+$ 192.0483. found 192.0476; HPLC>99% ($t_R$=10.18 min, 55 (A):45 (B) 0.009 (C); $t_R$=3.52 min, 55 (A):45 (B) 0.1 (C)).

(5-(Pyridin-3-yl)furan-2-yl)methanol (45)

To a slurry of 23 (54 mg, 0.31 mmol) in CH$_3$OH (5 mL) was added sodium borohydride (12 mg, 0.31 mmol) in one portion and the resultant solution was stirred at room temperature for 10 min. The reaction was stopped by the addition of aqueous sodium bicarbonate (50:50 satd. soln./water, v:v) and the CH$_3$OH was removed in vacuo. The residue was partitioned between water (20 mL) and ether (20 mL), the organic layer was collected and the aqueous fraction was re-extracted with ether (2×20 mL). The combined organic portions were washed with water (20 mL), dried (MgSO$_4$), filtered and concentrated in vacuo to afford the title compound 45 (50 mg, 92% yield) as an off white solid: mp=119-120° C.; $^1$H NMR (CDCl$_3$, 500 MHz) δ 8.88 (s, 1H), 8.42 (m, 1H), 7.88 (m, 1H), 7.27, (m, 1H), 6.65 (d, J=3.1 Hz, 1H), 6.38 (d, J=3.1 Hz, 1H), 4.66 (s, 2H); LRMS (ESI) m/z calcd for C$_{10}$H$_{10}$NO$_2$ [M+H]$^+$ 176. found 176; HRMS (ESI) m/z calcd for C$_{10}$H$_{10}$NO$_2$[M+H]$^+$ 176.0712. found 176.0694; HPLC>98% ($t_R$=4.60 min, 55 (A):45 (B): 0.032 (C); $t_R$=3.64 min, 55 (A):45 (B): 0.1 (C)).

tert-Butyl prop-2-ynylcarbamate (46)

To a solution of propargylamine (803 mg, 14.6 mmol) in CH$_2$Cl$_2$ (15 mL) at 0° C. was added a solution of di-tert-butyl dicarbonate (2.67 g, 15.3 mmol) in CH$_2$Cl$_2$ (20 mL) via dropping funnel over 25 min, the ice bath was removed and the resultant solution was stirred at ambient temperature for 30 min. The solvent was removed in vacuo and the crude material was chromatographed on silica gel (EtOAc/Hex, 10/90, R$_f$=0.28) to afford the title compound 46 (2.23 g, 98% yield) as a white solid: mp=39-40° C.; $^1$H NMR (CDCl$_3$) δ 4.79 (s, 1H), 3.90 (br s, 2H), 2.20 (m, 1H), 1.43 (s, 9H); LRMS (ESI) m/z calcd for C$_8$H$_{13}$NNaO$_2$ [M+Na]$^+$ 178. found 178.

tert-Butyl 3-(pyridin-3-yl)prop-2-ynylcarbamate (47)

To a pressure tube containing a magnetic stir bar was added 46 (202 mg, 1.3 mmol) and the vial was purged with argon. To the tube is added a solution of tetrakis(triphenylphosphine) palladium(0) (45 mg, 0.04 mmol) in ethanol/dimethoxyethane (1:1, 2 mL), sodium carbonate$_{(aq)}$ (2 M, 4 mL, 4 mmol), copper(I)iodide (46 mg, 0.24 mmol) and the vial was once again purged with argon. The resultant solution was stirred at room temperature for 5 min when 3-bromopyridine (483 μL, 5 mmol) was added as a neat oil. The tube was purged with argon, capped, heated to 90° C. and stirred for 1 h. The solution was cooled to room temperature and poured into a flask containing anhydrous sodium sulfate (5 g). The solution was dried for 10 min, filtered and the solvent was removed in vacuo. The crude material was chromatographed on silica gel (CH$_3$OH/CHCl$_3$, 5/95, R$_f$=0.43) to afford the title compound 47 (295 mg, 97% yield) as a brown solid: mp=74-78° C.; $^1$H NMR (CDCl$_3$) δ 8.63 (m, 1H), 8.51 (m, 1H), 7.67 (m, 1H), 7.22 (m, 1H), 5.05 (br s, 1H), 4.15 (m, 2H), 1.45 (s, 9H); LRMS (ESI) m/z calcd for C$_{13}$H$_{16}$N$_2$O$_2$ [M+H]$^+$ 233. found 233; m/z calcd for C$_9$H$_9$N$_2$O$_2$ [M+H−CH$_2$C(CH$_3$)$_2$]$^+$ 177. found 177; m/z calcd for C$_8$H$_9$N$_2$ [M+H−t-Boc]$^+$ 133. found 133.

3-(Pyridin-3-yl)prop-2-yn-1-amine (48)

To a solution of 47 (104 mg, 0.45 mmol) in CH$_2$Cl$_2$ (1 mL) was added TFA (2 mL, excess) and the resultant solution was stirred at room temperature for 1 h. The solvent and excess TFA were removed under a stream of nitrogen and the residue was partitioned between HCl$_{(aq)}$ (1.0 M, 2 mL) and EtOAc (10 mL). The aqueous fraction was collected and subsequently washed with EtOAc (2×10 mL). To the remaining aqueous fraction was added CH$_2$Cl$_2$ (20 mL) and water (20 mL) and the pH was adjusted to 10 with NaOH$_{(aq)}$ (10 N) while stirring. The organic fraction was collected and the remaining aqueous fraction was extracted with CH$_2$Cl$_2$ (2×15 mL). The combined organic fractions were dried (Na$_2$SO$_4$), filtered and the solvent was removed in vacuo to afford the title compound 48 (free base, 58 mg, 97% yield) as a brown oil. Due to the high potential of autooxidation, the dihydrochloride salt was made by dissolving the amine free base in Et$_2$O and precipitating with etherial HCl. The solvent and excess HCl were removed in vacuo, the solid dihydrochloride was triturated with Et$_2$O and collected by filtration to afford the title compound 48 (dihydrochloride, 91 mg, 99% yield) as a white solid: $^1$H NMR (D$_2$O) δ 8.94 (m, 1H), 8.79 (m, 1H), 8.65 (m, 1H), 8.06 (m, 1H), 4.15 (s, 2H); LRMS (ESI) m/z calcd for C$_8$H$_9$N$_2$ [M+H]$^+$ 133. found 133; HRMS (ESI) m/z calcd for C$_8$H$_9$N$_2$ [M+H]$^+$ 133.0766. found 133.0763; HPLC>98% ($t_R$=5.70 min, 60 (A):40 (B): 0.02 (C); $t_R$=3.05 min, 60 (A):40 (B): 0.07 (C)).

tert-Butyl N-methyl-3-(pyridin-3-yl)prop-2-ynylcarbamate (49)

To a solution of sodium hydride (60% dispersion in mineral oil, 30 mg, 0.95 mmol) in anhydrous THF (3 mL) at 0° C. was added a solution of 47 (109 mg, 0.47 mmol) in anhydrous THF (2 mL) dropwise over 15 min. To the resultant solution was added a solution of iodomethane (150 μL, 2.42 mmol) in THF (5 mL) over 10 min, the ice bath was removed and the solution was stirred at ambient temperature for 16 h. The reaction was stopped by the addition of water (5 mL) and the aqueous fraction was extracted with EtOAc (3×20 mL), washed with water, dried (Na$_2$SO$_4$), filtered and the solvent was removed in vacuo. The crude material was chromatographed on silica gel (EtOAc/Hex, 25/75, R$_f$=0.18) to afford the title compound 49 (69 mg, 60% yield) as a yellow oil: $^1$H NMR (CDCl$_3$) δ 8.65 (s, 1H), 8.52 (m, 1H), 7.69 (m, 1H), 7.24 (m, 1H), 4.29 (s, 2H), 2.97 (s, 3H), 2.97 (s, 9H); LRMS (ESI) m/z calcd for C$_{14}$H$_{19}$N$_2$O$_2$ [M H]$^+$ 247. found 247.

N-Methyl-3-(pyridin-3-yl)prop-2-yn-1-amine (50)

To a solution of 49 (43 mg, 0.17 mmol) in CH$_2$Cl$_2$ (0.8 mL) at 0° C. was added TFA (1.5 mL, excess), the ice bath was removed and the resultant solution was stirred at ambient temperature for 1 h. The solvent and excess TFA were removed under a stream of argon and the residue was dissolved in HCl$_{(aq)}$ (1.0 M, 1 mL) and washed with CH$_2$Cl$_2$ (3×10 mL). To the aqueous fraction was added $CH_2Cl_2$ (8 mL) and water (8 mL) and the pH was adjusted to 10 with $NaOH_{(aq)}$ (10 N) while stirring. The organic fraction was collected and the aqueous layer was extracted with $CH_2Cl_2$ (2×10 mL). The combined organic fractions were dried ($Na_2SO_4$), filtered and the solvent was removed in vacuo. The crude material was chromatographed on silica gel ($CH_3OH/CHCl_3$, 10/90, $R_f$=0.16) to afford the title compound 50 (13 mg, 53% yield) as an orange oil: $^1$H NMR ($CDCl_3$) δ 8.65 (m, 1H), 8.51 (m, 1H), 7.07 (m, 1H), 7.23 (m, 1H), 3.64 (br s, 2H), 2.50 (br s, 3H); LRMS (ESI) m/z calcd for $C_9H_{11}N_2$ $[M+H]^+$ 147. found 147; LRMS (ESI) m/z calcd for $C_8H_6N$ $[M-NH(CH_3)]^+$ 116. found 116; HRMS (ESI) m/z calcd for $C_9H_{11}N_2$ $[M+H]^+$ 147.0922. found 147.0921; HPLC>98% ($t_R$=7.25 min, 60 (A):40 (B): 0.02 (C); $t_R$=2.91 min, 60 (A):40 (B): 0.07 (C)).

N,N-Dimethyl-3-(pyridin-3-yl)prop-2-yn-1-amine (51)

To a pressure tube containing a magnetic stir bar was added N,N-dimethylpropargylamine (333 mg, 4 mmol) and the vial was purged with argon. To the tube is added a solution of tetrakis(triphenylphosphine)palladium(0) (139 mg, 0.12 mmol) in ethanol/dimethoxyethane (1:1, 2 mL), sodium carbonate$_{(aq)}$ (2 M, 4 mL, 4 mmol), copper(I)iodide (46 mg, 0.24 mmol) and the vial was once again purged with argon. The resultant solution was stirred at room temperature for 5 min when 3-bromopyridine (483 µL, 5 mmol) was added as a neat oil. The tube was purged with argon, capped, heated to 90° C. and stirred for 1 h. The solution was cooled to room temperature and poured into a flask containing anhydrous sodium sulfate (5 g). The solution was dried for 10 min, filtered and the solvent was removed in vacuo. The crude material was chromatographed on silica gel ($CH_3OH/CHCl_3$, 10/90, $R_f$=0.13) to afford the title compound 51 (26 mg, 4% yield) as a brown oil: $^1$H NMR ($CDCl_3$) δ 8.67 (br s, 1H), 8.52 (m, 1H), 7.72 (m, 1H), 7.24 (m, 1H), 3.49 (s, 2H), 2.37 (s, 6H); LRMS (ESI) m/z calcd for $C_{10}H_{12}N_2$ $[M+H]^+$ 161. found 161; LRMS (ESI) m/z calcd for $C_8H_6N$ $[M-N(CH_3)_2]^+$ 116. found 116; HRMS (ESI) m/z calcd for $C_{10}H_{12}N_2$ $[M+H]^+$ 161.1079. found 161.1090; HPLC>98% ($t_R$=9.38 min, 60 (A):40 (B): 0.02 (C); $t_R$=4.70 min, 60 (A):40 (B): 0.07 (C)).

4-(Pyridin-3-yl)benzaldehyde (52)

The general Suzuki coupling procedure was followed. The crude material was chromatographed on silica gel ($CH_3OH/CHCl_3$, 10/90, $R_f$=0.4) to afford the title compound 52 (677 mg, 71% yield) as a yellow solid: mp=53-54° C. $^1$H NMR ($CDCl_3$) δ 10.07 (s, 1H), 8.89 (s, 1H), 8.66 (m, 1H), 7.99 (d, J=8.1 Hz, 2H), 7.91 (m, 1H), 7.75 (d, J=8.1 Hz, 2H), 7.41 (m, 1H); LRMS (ESI) m/z calcd for $C_{12}H_{10}NO$ $[M+H]^+$ 184. found 184.

Cis/trans 4-(pyridin-3-yl)phenyl-1-carbaldehyde oximes (53)

To a solution of 52 (547 mg, 2.99 mmol) in 95% ethanol (6 mL) was added hydroxylamine hydrochloride (228 mg, 3.28 mmol), sodium acetate (269 mg, 3.28 mmol) and the resultant slurry was heated to reflux and stirred for 25 min. The solvent was removed in vacuo and the residue was triturated with $CH_2Cl_2$. The white solid (TLC: $CH_3OH/CHCl_3$, 5/95, $R_f$=0.22) was collected by filtration to afford the cis/trans mixture of the title compound 53 (580 mg, 98% yield) as a yellow solid: mp=160-165° C. dec.; $^1$H NMR. ($DMSO$-$D_6$) δ 11.39 (s, 1H), 8.98 (s, 1H), 8.63 (m, 1H), 8.21 (m, 2H), 7.79 (m, 2H) 7.72 (m, 2H), 7.57 (m, 1H), 7.57 (m, 1H); LRMS (ESI) m/z calcd for $C_{12}H_{11}N_2O$ $[M+H]^+$ 199. found 199.

(4-(Pyridin-3-yl)phenyl)methanamine (54)

To a solution of 53 (146 mg, 0.74 mmol) in anhydrous THF (6 mL) under argon at room temperature was added a solution of LAH (1.0 M in THF, 923 µL, 0.923 mmol) dropwise via syringe over 10 min. The resultant solution was heated to reflux, stirred for 5 h, the heat bath was removed and the solution was stirred at ambient temperature overnight. The reaction was stopped by the dropwise addition 1N HCl, diluted to 20 mL with 1N HCl, washed with EtOAc (20 mL), the pH was adjusted to 8 with $NaOH_{(aq)}$ (10 N), extracted with $CH_2Cl_2$ (3×40 mL), dried ($Na_2SO_4$) and the solvent was removed in vacuo. The residue was chromatographed on silica gel ($CH_3OH/CHCl_3$, 10/90, $R_f$=0.03-0.13) to afford the title compound 54 (47 mg, 34% yield) as a yellow oil that solidifies in a freezer: $^1$H NMR ($CDCl_3$) δ 8.84 (m, 1H), 8.58 (m, 1H) 7.87 (m, 1H), 7.56 (d, J=8.1 Hz, 2H), 7.43 (d, J=8.0 Hz, 2H), 7.35 (m, 1H), 3.94 (s, 2H), 1.60 (br s, 2H); LRMS (ESI) m/z calcd for $C_{12}H_{12}N_2$ $[M+H]^+$ 185. found 185; m/z calcd for $C_{12}H_{10}N$ $[M-NH_2]^+$ 168. found 168; HRMS (ESI) m/z calcd for $C_{12}H_{12}N_2$ $[M+H]^+$ 185.1079. found 185.1093; HPLC>99% ($t_R$=7.06 min, 60 (A):40 (B): 0.02 (C); $t_R$=3.19 min, 60 (A):40 (B): 0.07 (C)).

3-Methyl-5-(3-methylthiophen-2-yl)pyridine (55)

To a glass vial containing a magnetic stir bar is added a solution of 12 (108 mg, 0.42 mmol) in DME (1 mL) and the vial is purged with argon. To the vial is added a solution of tetrakis(triphenylphosphine)palladium(0) (15 mg, 0.013 mmol) in ethanol, tetramethyltin (294 µL, 2.13 mmol), sodium carbonate$_{(aq)}$(2 M, 0.4 mL, 0.9 mmol), the vial is purged with argon, capped, heated to 90° C. and stirred for 1 h. The solution is cooled to room temperature and poured into a flask containing anhydrous sodium sulfate (1 g). The solution is dried for 10 min, filtered and the solvent is removed in vacuo. The crude material was chromatographed on silica gel (EtOAc/Hex, 10/90, $R_f$=0.14) to afford the title compound 55 (29 mg, 36% yield) as a chalky oil: $^1$H NMR ($CDCl_3$) δ 8.53 (m, 1H), 8.39 (m, 1H), 7.56 (m, 1H), 7.27 (d, J=4.62 Hz, 1H), 6.96 (d, J=5.11 Hz, 1H), 2.39 (s, 3H), 2.33 (s, 3H); LRMS (ESI) m/z calcd for $C_{11}H_{12}NS$ $[M+H]^+$ 190. found 190; HRMS (ESI) m/z calcd for $C_{11}H_{12}NS$ $[M+H]^+$ 190.0690. found 190.0706; HPLC>99% ($t_R$=5.07 min, 55 (A):45 (B): 0.01 (C); $t_R$=3.69 min, 60 (A):40 (B): 0.07 (C)).

3-Methyl-5-(thiophen-3-yl)pyridine (56)

To a glass vial containing a magnetic stir bar is added a solution of the 19 (17 mg, 0.07 mmol) in DME (1 mL) and the vial is purged with argon. To the vial is added a solution of tetrakis(triphenylphosphine)palladium(0) (3 mg, 0.002 mmol) in ethanol, tetramethyltin (12 µL, 0.08 mmol), sodium carbonate$_{(aq)}$ (2 M, 1.3 mL, 2.6 mmol), the vial is purged with argon, capped, heated to 90° C. and stirred for 1 h. The solution is cooled to room temperature and poured into a flask containing anhydrous sodium sulfate (1 g). The solution is dried for 10 min, filtered and the solvent is removed in vacuo. The crude material was chromatographed on silica gel (preparative TLC, EtOAc/Hex, 25/75, $R_f$=0.22) to afford the title compound 56 (3 mg, 26% yield) as a clear oil::$^1$H NMR ($CDCl_3$) δ 8.67 (br s, 1H), 8.36 (br s, 1H), 7.67 (br s, 1H), 7.49 (m, 1H), 7.43 (m, 1H), 7.38 (m, 1H), 2.38 (s, 3H); LRMS (ESI) m/z calcd for $C_{10}H_{10}NS$ [M+H]$^+$ 176. found 176; HRMS (ESI) m/z calcd for $C_{10}H_{10}NS$ [M+l1]$^+$ 176.0534. found 176.0551; HPLC>99% ($t_R$=5.41 min, 55 (A):45 (B): 0.01 (C); $t_R$=2.89 min, 60 (A):40 (B): 0.07 (C)).

5-(Pyridin-3-yl)thiophen-2-amine (57)

To a solution of 12 (233 mg, 1.13 mmol) in $CH_3OH$/EtOAc (1:1, 10 mL) was added a slurry of 10% Pd/C (30 mg) in $CH_3OH$/EtOAc (1:1, 10 mL). The resultant solution was degassed and purged with hydrogen three times and then hydrogenated under double balloon pressure for 24 h. The catalyst was removed by filtration through a pad of celite, the solvent was removed in vacuo, the residue was dissolved in MeOH and absorbed to silica gel. The solvent was removed in vacuo and the material was chromatographed on silica gel (EtOAc/Hex, 50/50, $R_f$=0.21) to afford the title compound 57 (180 mg, 91% yield) as a yellow solid: mp=126° C. (dec); $^1$H NMR (CDCl$_3$) δ 8.72 (m, 1H), 8.39 (m, 1H), 7.69 (m, 1H), 7.23 (m, 1H), 6.98 (d, J=4.1 Hz, 1H), 6.18 (d, J=4.1 Hz, 1H), 3.75 (br s, 2H); LRMS (ESI) m/z calcd for $C_9H_9N_2S$ [M+H]$^+$ 177. found 177; HRMS (ESI) m/z calcd for $C_9H_9N_2S$ [M+H]$^+$ 177.0486. found 177.0472; HPLC>99% ($t_R$=5.57 min, 55 (A):45 (B): 0.018 (C); $t_R$=4.33 min, 60 (A):40 (B): 0.02 (C)).

3-(1-Methyl-1/1-imidazol-4-yl)pyridine and 3-(1-methyl-1H-imidazol-5-yl)pyridine (58a, b)

To a solution of 34 (37 mg, 0.26 mmol) in THF (4 mL) under argon was added sodium hydride (11 mg, 0.28 mmol) in one portion and the resultant slurry was stirred for 5 min. Iodomethane (190 µL, 0.31 mmol) was added and the resultant solution was stirred for 10 min. The reaction was stopped by the careful addition of aqueous hydrochloric acid (0.25 N, 6 mL) and washed with ethyl ether (3×10 ml). The aqueous fraction was adjusted to pH 9 with NaOH$_{(aq)}$ (10 N) and extracted with ethyl ether (3×30 mL), dried (Na$_2$SO$_4$), filtered and the solvent was removed in vacuo. The crude material was chromatographed on silica gel (CH$_3$OH/CHCl$_3$, 2.5/97.5, $R_f$=0.15) to afford the title compounds 58a, b as an inseparable mixture (27 mg, 66% yield) of an orange oil: 58a $^1$H NMR (CDCl$_3$) δ 8.95 (m, 1H), 8.47 (m, 1H), 8.11 (m, 1H), 7.52 (br s, 1H), 7.31 (m, 1H), 7.26 (br s, 1H) 3.75 (s, 3H); 58b $^1$H NMR (CDCl$_3$) δ 8.69 (m, 1H), 8.62 (m, 1H), 7.71 (m, 1H), 7.62 (br s, 1H), 7.39 (m, 1H), 7.19 (br s, 1H), 3.70 (s, 3H); LRMS (ESI) m/z calcd for $C_9H_{10}N_3$ [M+H]$^+$ 160. found 160; HRMS (ESI) m/z calcd for $C_9H_{10}N_3$ [M+H]$^+$ 160.0875. found 160.0866; HPLC>99% ($t_R$=19.80 min, 55 (A):45 (B): 0.032 (C); $t_R$=9.47 min, 55 (A):45 (B): 0.1 (C).

3-(1-Ethyl-1H-imidazol-4-yl)pyridine (59)

To a solution of 34 (36 mg, 0.25 mmol) in THF (5 mL) under argon was added sodium hydride (12 mg, 0.29 mmol) in one portion and the resultant slurry was stirred for 20 min. Iodoethane (26 µL, 0.32 mmol) was added and the resultant solution was stirred for 10 min. The reaction was stopped by the careful addition of aqueous hydrochloric acid (1 N, 2 mL), diluted with 13 mL of water and washed with ethyl acetate (3×15 ml). Dichloromethane was added (25 mL) and the aqueous was adjusted to pH 9 with NaOH$_{(aq)}$ (10 N). The organic fraction was collected and the aqueous fraction was extracted with dichloromethane (20 mL), the combined organic fractions were dried (Na$_2$SO$_4$), filtered and the solvent was removed in vacuo. The crude material was chromatographed on silica gel (CH$_3$OH/CHCl$_3$, 2.5/97.5, $R_f$=0.27) to afford the title compound 59 (34 mg, 79% yield) as a clear oil: $^1$H NMR (CDCl$_3$) δ 8.93 (m, 1H), 8.44 (m, 1H), 8.07 (m, 1H), 7.54 (br s, 1H), 7.28 (m, 2H), 4.02 (q, J=7.4 Hz, 2H), 1.49 (t, J=7.4 Hz, 3H); LRMS (ESI) m/z calcd for $C_{10}H_{11}N_3$ [M+H]$^+$ 174. found 174; HRMS (ESI) m/z calcd for $C_{10}H_{11}N_3$ [M+H]$^+$ 174.1031. found 174.1042; HPLC>97% ($t_R$=13.28 min, 60 (A):40 (B): 0.02 (C); $t_R$=3.67 min, 80 (A):20 (B): 0.1 (C).

3-(1-benzyl-1H-imidazol-4-yl)pyridine (60)

To a solution of 34 (35 mg, 0.25 mmol) in THF (5 mL) under argon was added sodium hydride (12 mg, 0.29 mmol) in one portion and the resultant slurry was stirred for 20 min. Benzyl bromide (26 µL, 0.32 mmol) was added and the resultant solution was stirred for 10 min. The reaction was quenched by the slow addition of HCl$_{(aq)}$ (1 N, 2 mL), diluted with 13 mL of water and washed with ethyl acetate (3×15 ml). Dichloromethane was added (25 mL) and the aqueous fraction was adjusted to pH 9 with NaOH$_{(aq)}$ (10 N). The organic fraction was collected and the aqueous was extracted with dichloromethane (20 mL), the combined organic fractions were dried (Na$_2$SO$_4$), filtered and the solvent was removed in vacuo. The crude material was chromatographed on silica gel (CH$_3$OH/CHCl$_3$, 2.5/97.5, $R_f$=0.26) to afford the title compound 60 (43 mg, 74% yield) as a white semisolid: $^1$H NMR (CDCl$_3$) δ 8.95 (br s, 1H), 8.47 (br s, 1H), 8.10 (m, 1H) 7.64 (m, 1H) 7.42-7.17 (m, 7H) 5.17 (s, 2H); LRMS (ESI) m/z calcd for $C_{15}H_{14}N_3$ [M+H]$^+$ 236. found 236; HRMS (ESI) m/z calcd for $C_{15}H_{14}N_3$ [M+H]$^+$ 236.1188. found 236.1198; HPLC>99% ($t_R$=10 min, 60 (A):40 (B): 0.02 (C); $t_R$=6.12 min, 60 (A):40 (B): 0.07 (C)).

3-(4-Methyl-1H-imidazol-1-yl)pyridine and 3-(5-methyl-1H-imidazol-1-yl)pyridine (61)

To a solution of 4-methylimidazole (251 mg, 3.06 mmol) in DMF (5 mL) was added NaH (60% dispersion in mineral oil, 133 mg, 3.33 mmol) and the resultant solution was stirred at room temperature for 30 min under argon. To the solution was added a solution of 3-fluoropyridine (88 µL, 1.01 mmol) in DMF (1 mL) and the resultant solution was heated to 100° C. and stirred overnight. The solution was cooled to rt, poured into aqueous saturated sodium bicarbonate (50 mL), extracted with ethyl acetate (3×50 mL), washed with brine, dried (Na$_2$SO$_4$), filtered and the solvent was removed in vacuo. The crude material was chromatographed on silica gel (CH$_3$OH/CHCl$_3$, 2/98, $R_f$=0.27) to afford the title compound 61 (67 mg, 41% yield), as a regioisomeric mixture in a 3:1 ratio as determined by $^1$H NMR, as a yellow semi-solid that solidified upon standing in a freezer: $^1$H NMR (CDCl$_3$) δ 8.72 (m, 1H), 8.62 (m, 1H), 7.78 (s, 0.66H), 7.69 (M, 0.66H), 7.65 (m, 0.33H), 7.59 (s, 0.33H), 7.47 (m, 0.33H) 7.42 (m, 0.66H), 7.02 (s, 0.66H), 6.96 (s, 0.33H), 2.31 (s, 2.25H), 2.20 (s, 0.75H); LRMS (ESI) m/z calcd for $C_9H_{10}N_3$ [M+H]$^+$ 160. found 160; HRMS (ESI) m/z calcd for $C_9H_{10}N_3$ [M+H]$^+$ 160.0875. found 160.0884; HPLC>99% ($t_R$=14.91 min, 10.39 min, 55 (A):45 (B): 0.032 (C); $t_R$=6.74 min, 8.61 min, 60 (A):40 (B): 0.05 (C)).

3-(2-Methyl-1H-imidazol-1-yl)pyridine (62)

To a solution of 2-methylimidazole (256 mg, 3.13 mmol) in DMF (5 mL) was added NaH (60% dispersion in mineral oil, 180 mg, 4.50 mmol) and the resultant solution was stirred at room temperature for 30 min under argon. To the solution was added a solution of 3-fluoropyridine (88 µL, 1.01 mmol) in DMF (1 mL), the resultant solution was heated to 100° C. and stirred overnight. The solution was cooled to rt, poured into aqueous saturated sodium bicarbonate (50 mL), extracted with ethyl acetate (3×50 mL), washed with brine, dried (Na$_2$SO$_4$), filtered and the solvent was removed in vacuo. The crude material was chromatographed on silica gel (CH$_3$OH/ CHCl$_3$, 5/95, R$_f$=0.12) to afford the title compound 62 (48 mg, 30% yield) as a yellow oil: $^1$H NMR (CDCl$_3$) δ 8.69 (m, 1H), 8.63 (m, 1H), 7.64 (m, 1H), 7.45 (m, 1H), 7.07 (m, 1H), 7.02 (m, 1H), 2.38 (s, 3H); LRMS (ESI) m/z calcd for C$_9$H$_{10}$N$_3$ [M+H]$^+$ 160. found 160; HRMS (ESI) m/z calcd for C$_9$H$_{10}$N$_3$ [M+H]$^+$ 160.0875. found 160.0866; HPLC>99% (t$_R$=7.75 min, 55 (A):45 (B): 0.032 (C); t$_R$=5.45 min, 55 (A):45 (B): 0.01 (C)).

3-(1H-imidazol-1-yl)pyridine (63)

To a solution of imidazole (420 mg, 6.3 mmol) in DMF (6 mL) was added NaH (60% dispersion in mineral oil, 250 mg, 6.3 mmol) and the resultant solution was stirred at room temperature for 30 min under argon. To the solution was added a solution of 3-fluoropyridine (183 µL, 2.1 mmol) in DMF (2 mL) and the resultant solution was heated to 100° C. and stirred overnight. The solution was cooled to rt, poured into aqueous saturated sodium bicarbonate (50 mL), extracted with ethyl acetate (3×50 mL), washed with brine, dried (Na$_2$SO$_4$), filtered and the solvent was removed in vacuo. The crude material was chromatographed on silica gel (CH$_3$OH/CH$_2$Cl$_2$, 5/95, R$_f$=0.12) to afford the title compound 63 (176 mg, 59% yield) as a yellow oil: $^1$H NMR (CDCl$_3$) δ 8.75 (m, 1H), 8.63 (m, 1H), 7.87 (s, 1H), 7.73 (m, 1H), 7.44 (m, 1H), 7.30 (s, 1H), 7.26 (s, 1H); LRMS (ESI) m/z calcd for C$_8$H$_8$N$_3$ [M+H]$^+$ 146. found 146; HRMS (ESI) m/z calcd for C$_8$H$_8$N$_3$ [M+H]$^+$ 146.0718. found 146.0730; HPLC>99% (t$_R$=7.18 min, 55 (A):45 (B): 0.032 (C); 5.06 min, 55 (A):45 (B): 0.1 (C)).

3-(1H-tetrazol-5-yl)pyridine (64)

To a solution of 3-cyanopyridine (1.1 g, 10.6 mmol) in DMF (15 mL) was added ammonium chloride (718 mg, 13.4 mmol) and sodium azide (824 mg, 12.7 mmol) and the resultant slurry was vigorously stirred at 90° C. for 15 h. The DMF was removed in vacuo, the residue was dissolved in aqueous potassium hydroxide (1 M, 20 mL), washed with EtOAc (2×25 mL), the aqueous layer was adjusted to pH ~3 with aqueous HCl (6 N) and the solid was collected by filtration to afford the title compound 64 (904 mg, 46% yield) as a white solid: mp=239-241° C. dec.; $^1$H NMR (CDCl$_3$) δ 9.21 (m, 1H), 8.76 (m, 1H), 8.39 (m, 1H), 7.64 (m, 1H); LRMS (ESI) m/z calcd for C$_6$H$_6$N$_5$ [M+H]$^+$ 148. found 148; HRMS (ESI) m/z calcd for C$_6$H$_6$N$_5$ [M+H]$^+$ 148.0623. found 148.0624; HPLC>99% (t$_R$=4.88 min, 60 (A):40 (B): 0.009 (C); t$_R$=3.74 min, 60 (A):40 (B): 0.02 (C)).

3-Tetrazol-1-yl-pyridine (65)

To a solution of 3-aminopyridine (1.3 g, 13.4 mmol) in HOAc (20 mL) was added sodium azide (1.3 g, 20.1 mmol) and trimethyl orthoformate (2.36 mL, 21.6 mmol) and the resultant slurry was stirred at room temperature overnight and subsequently refluxed for 6 h. The reaction was cooled to room temperature and stopped by pouring into 50 mL of ice water. EtOAc (50 mL) was added, collected and subsequently washed with aqueous sodium hydroxide (1 N). The organic layer was collected, dried (MgSO$_4$) and concentrated in vacuo to afford the title compound 65 (1.0 g, 52%) as a white solid: mp=74-76° C.; $^1$H NMR (CDCl$_3$) δ 10.37 (s, 1H), 9.36 (m, 1H), 8.98 (m, 1H), 8.56 (m, 1H), 7.88 (m, 1H); LRMS (ESI) m/z calcd for C$_6$H$_6$N$_3$ [M+H—N$_2$]$^+$ 120. found 120; HRMS (ESI) m/z calcd for C$_6$H$_6$N$_5$ [M+H]$^+$ 148.0623. found 148.0636; HPLC>99% (t$_R$=3.44 min, 60 (A):40 (B): 0.009 (C); t$_R$=2.71 min, 60 (A):40 (B): 0.02 (C)).

TABLE 10

Synthetic compounds obtained by Suzuki coupling (Scheme 2) examined for inhibition of coumarin 7-hydroxylation.

| compd | X | Y | HetAr |
|---|---|---|---|
| 7 | H | H | 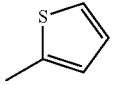 |
| 8 | H | H | 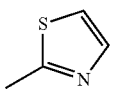 |
| 9 | H | H | 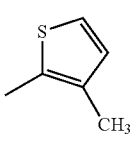 |
| 10 | F | H | 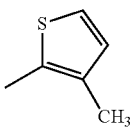 |
| 11 | OCH$_3$ | H | 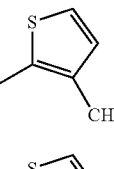 |
| 12 | H | Br | 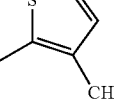 |
| 13 | H | H | 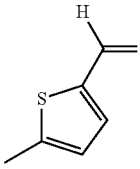 |
| 14 | H | H | 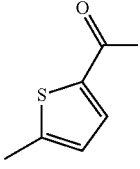 |
| 15 | H | H | 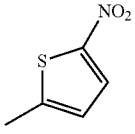 |
| 16 | H | H | 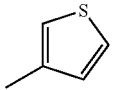 |

TABLE 10-continued

Synthetic compounds obtained by Suzuki coupling (Scheme 2) examined for inhibition of coumarin 7-hydroxylation.

| compd | X | Y | HetAr |
|---|---|---|---|
| 17 | F | H |  |
| 18 | OCH$_3$ | H |  |
| 19 | H | Br |  |
| 20 | H | H | 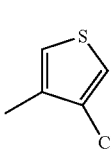 |
| 21 | F | H | 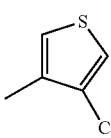 |
| 22 | OCH$_3$ | H | 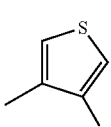 |
| 23 | H | H | 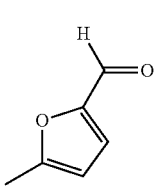 |
| 24 | H | H | 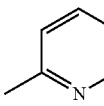 |
| 25 | H | H | 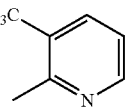 |
| 26 | H | H | 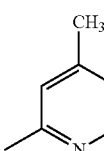 |
| 27 | H | H | 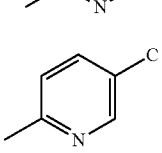 |
| 28 | H | H | 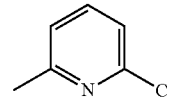 |
| 29 | H | H | 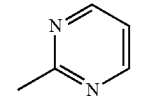 |
| 30 | H | H | 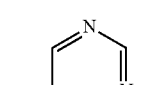 |
| 31 | H | H | 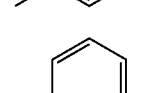 |
| 32 | Cl | H | 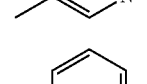 |
| 33 | H | H | 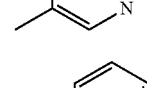 |
| 34 | H | H | 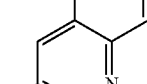 |
| 35 | H | H | 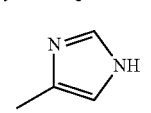 |

TABLE 11

Effect of nicotine and synthetic heteroaromatic nicotine analogues on coumarin 7-hydroxylation by human cytochrome P-450 2A6.[a]

| cpd | K$_i$ (μM) ± SD |
|---|---|
| Nicotine | 4.4 ± 0.6 |
| 7 | 1.2 ± 0.6 |
| 8 | 3.2 ± 0.6 |
| 9 | 0.10 ± 0.02 |
| 10 | 0.21 ± 0.02 |
| 11 | ≥67[c] |
| 12 | 1.5 ± 0.2 |
| 13 | 0.79 ± 0.12 |
| 14 | 1.4 ± 0.2 |
| 15 | 19.7 ± 2.3 |
| 16 | 0.22 ± 0.04 |
| 17 | 0.97 ± 0.20 |
| 18 | 9.7 ± 2.1 |
| 19 | 4.5 ± 0.8 |
| 20 | 0.25 ± 0.04 |
| 21 | 2.6 ± 0.5 |

TABLE 11-continued

Effect of nicotine and synthetic heteroaromatic nicotine analogues on coumarin 7-hydroxylation by human cytochrome P-450 2A6.[a]

| cpd | $K_i$ (µM) ± SD |
|---|---|
| 22 | 6.6 ± 0.8 |
| 23 | ≥67[c] |
| 24 | 7.7 ± 1.2 |
| 25 | 43.7[b] ± 11.5 |
| 26 | 5.1 ± 0.8 |
| 27 | 2.7 ± 0.6 |
| 28 | 9.8 ± 2 |
| 29 | 1.8 ± 0.36 |
| 30 | 27.4 ± 4.2 |
| 31 | 1.1 ± 0.1 |
| 32 | 6.3 ± 2.5 |
| 33 | 44.5[b] ± 41 |
| 34 | 0.25 ± 0.05 |
| 35 | 6.2 ± 1 |
| 36 | 0.24 ± 0.04 |
| 37a | 0.71 ± 0.08 |
| 37b | 13.7 ± 1.2 |
| 38a | 0.02 ± 0.003 |
| 38b | 1.2 ± 0.2 |
| 39a | 0.04 ± 0.004 |
| 39b | 1.5 ± 0.3 |
| 39c | 2.8 ± 0.8 |
| 40 | 0.18 ± 0.02 |
| 41 | 0.28 ± 0.06 |
| 42 | 22.2 ± 3.3 |
| 43 | 47.2 ± 3.1 |
| 44 | 5.6 ± 0.7 |
| 45 | 35.2[b] ± 16.7 |
| 48 | 0.09 ± 0.01 |
| 50 | 0.89 ± 0.1 |
| 51 | 22.7 ± 7.8 |
| 54 | 1.4 ± 0.3 |
| 55 | 11 ± 1.5 |
| 56 | 0.17 ± 0.05 |
| 57 | 0.59 ± 0.05 |
| 58 | 0.13 ± 0.02 |
| 59 | 0.52 ± 0.05 |
| 60 | 0.23 ± 0.03 |
| 61 | 0.17 ± 0.04 |
| 62 | 0.25 ± 0.06 |
| 63 | 0.62 ± 0.13 |
| 64 | 64.8 ± 11.3 |
| 65 | ≥67[c] |

[a]$K_i$ values were determined by increasing the concentration of inhibitors added to the assay mixture containing insect cell microsomes expressing CYP2A6 in 0.1M Tris buffer, pH 7.5, an NADPH-generating system, DETAPAC and 3 mM MgCl$_2$. Each value is the mean of at least 3 determinations ± SD. The experimental details are described in the Experimental Section.
[b]This compound has a high fluorescence background that increases the standard deviation.
[c]No inhibition was observed at 400 µM.

TABLE 12

Selective functional inhibition of CYP3A4, 2E1, 2B6, 2C9, 2C19 and 2D6 by synthetic heteroaromatic nicotine analogues.[a]

| cpd | IC$_{50}$ ± SD | | | | | | |
|---|---|---|---|---|---|---|---|
| | 2A6[b] | 3A4[c] | 2E1[b] | 2B6[b] | 2C9[b] | 2C19[b] | 2D6[b] |
| 7 | 7.8 ± 3.7 | 57.0 ± 21.3 | 4.1 ± 0.82 | 70.8 ± 3.6 | 99.2 ± 12.0 | 178 ± 13 | >400 |
| 9 | 0.62 ± 0.10 | 6.0 ± 1.3 | 6.9 ± 2.1 | 3.9 ± 0.8 | 93.1 ± 8.8 | 20.1 ± 2.2 | 92.5 ± 10.8 |
| 13 | 4.8 ± 0.7 | 23.9 ± 7.3 | 34.3 ± 7.1 | 21.6 ± 2.5 | 55.2 ± 7.0 | 65.2 ± 5.8 | >400 |
| 14 | 8.6 ± 1.3 | 27.0 ± 9.2 | >400 | 217 ± 17 | 98.2 ± 11.3 | 62.7 ± 7.5 | 387 ± 62 |
| 16 | 1.4 ± 0.2 | 56.9 ± 19.2 | >400 | 59.1 ± 3.9 | 96.3 ± 9.5 | 111.2 ± 6 | 248 ± 35 |
| 17 | 5.8 ± 1.2 | 114 ± 25 | 7.2 ± 1.6 | 72.1 ± 8.6 | >400 | 182 ± 29 | 199 ± 16 |
| 20 | 1.5 ± 0.2 | 80.9 ± 13.2 | 6.3 ± 1.9 | 6.3 ± 0.7 | 123 ± 11 | 24.9 ± 1.4 | 193 ± 28 |
| 21 | 1.3 ± 0.1 | 39.1 ± 12.8 | 368 ± 79 | 11.8 ± 1.7 | >400 | 40.9 ± 2.1 | 296 ± 66 |
| 31 | 6.6 ± 0.7 | 64.7 ± 13.7 | >300 | 145 ± 11 | >300 | >300 | >300 |
| 34 | 1.5 ± 0.3 | 139.9 ± 14.0 | 25.5 ± 3.9 | 103 ± 9 | 41.8 ± 5.2 | 53.5 ± 4.8 | 98.0 ± 7.7 |
| 36 | 1.4 ± 0.3 | 13.0 ± 3.3 | 4.2 ± 1.1 | 214 ± 25 | 223 ± 28 | 37.2 ± 3.4 | 191 ± 30 |
| 37b | 4.2 ± 0.5 | >400 | >400 | 128 ± 22 | 398 ± 49 | 279 ± 21 | >400 |
| 37a, b | 9.8 ± 0.9 | 51.9 ± 8.2 | >400 | 206 ± 33 | 141 ± 18 | 175 ± 22 | >400 |
| 37a | 82.3 ± 7.3 | >400 | >400 | 372 ± 16 | 86.2 ± 13.8 | 118 ± 7 | >400 |
| 38a | 0.17 ± 0.02 | 58.7 ± 15.3 | 40.2 ± 18.1 | 52.2 ± 7.6 | 8.9 ± 1.5 | 2.0 ± 0.22 | 168 ± 16 |
| 38 | 3.7 ± 0.78 | 77.5 ± 14.6 | 77.5 ± 14.6 | 256 ± 29 | 208 ± 21 | 233 ± 21 | 197 ± 21 |
| 38b | 7.4 ± 1.3 | >400 | 0.86 ± 0.24 | 9.0 ± 0.8 | 0.71 ± 0.75 | 0.21 ± 0.03 | 12.9 ± 1.9 |
| 39a | 0.27 ± 0.02 | 47.1 ± 18.1 | 172 ± 52 | 191 ± 24 | 11.7 ± 2.2 | 22.0 ± 1.6 | 11.3 ± 2.6 |
| 57 | 3.5 ± 0.3 | 6.3 ± 1.4 | 31.1 ± 5.7 | 6.8 ± 0.8 | 2.1 ± 0.2 | 3.2 ± 0.2 | 14.4 ± 0.9 |
| 58 | 0.75 ± 0.1 | 262 ± 63 | 4.1 ± 0.7 | 146 ± 20 | 79.5 ± 8.9 | 122.1 ± 12.2 | 217 ± 20 |
| 59 | 3.1 ± 0.3 | 79.2 ± 27.7 | 80.0 ± 10.2 | 83.1 ± 4.7 | 75.2 ± 8.2 | 46.4 ± 4.2 | 344 ± 43 |
| 60 | 1.4 ± 0.2 | 75.1 ± 13.9 | 0.58 ± 0.10 | 5.3 ± 0.9 | 26.9 ± 2.9 | 12.1 ± 0.6 | 36.3 ± 4.4 |
| 61 | 1.0 ± 0.2 | 109 ± 46 | 57.9 ± 12.5 | >300 | >300 | >300 | 297 ± 31 |
| 62 | 1.5 ± 0.4 | 152 ± 70 | 109 ± 11 | >300 | >300 | >300 | 277 ± 40 |

[a]Compounds that were determined to have CYP2A6 IC$_{50}$ values below 10 µM and the cis/trans oxime isomers were tested for inhibitory potency and regioselectivity (33a, 33b, 33a, b) in the presence of CYP isoforms. IC$_{50}$ values were determined by increasing the concentration of potential inhibitors added to the assay mixture containing
[b]insect cell microsomes expressing the specific CYP isoform in 0.1M Tris buffer (CYP2A6) or 0.2M potassium phosphate buffer (CYP2E1, CYP2B6, CYP2C9, CYP2C19 and CYP2D6) or
[c]human liver microsomes in 0.05M potassium phosphate buffer, pH 7.5, an NADPH-generating system, DETAPAC and 3 mM MgCl$_2$. Each value is the mean of at least 3 determinations ± SD. The experimental details are described in the Experimental Section.

TABLE 13

Selectivity ratio (IC$_{50}$ CYPX/IC$_{50}$ CYP2A6)$^a$ of heteroaromatic nicotine analogues for human CYPs 3A4, 2E1, 2B6, 2C9, 2C19 and 2D6 versus human CYP2A6.$^b$

| compd | 3A4/2A6 | 2E1/2A6 | 2B6/2A6 | 2C9/2A6 | 2C19/2A6 | 2D6/2A6 |
|---|---|---|---|---|---|---|
| 7 | 7.3 | 0.53 | 9.1 | 13 | 23 | >51 |
| 9 | 10 | 11 | 6.3 | 150 | 39 | 149 |
| 13 | 5.0 | 7.1 | 4.5 | 12 | 14 | >100 |
| 14 | 3.1 | >46 | 25 | 11 | 7 | 45 |
| 16 | 400 | >286 | 42 | 69 | 81 | 177 |
| 17 | 20 | 1.2 | 12 | >69 | 31 | 34 |
| 20 | 53 | 4.2 | 4.2 | 45 | 17 | 128 |
| 21 | 2 | 284 | 9.1 | >308 | 32 | 227 |
| 31 | 10 | 45 | 22 | >45 | >45 | >45 |
| 34 | 93 | 17 | 69 | 28 | 35 | 65 |
| 36 | 9.3 | 3 | 153 | 159 | 27 | 136 |
| 37b | >95 | >95 | 30 | 94 | 66 | >95 |
| 37a, b | 5.3 | >41 | 21 | 15 | 18 | >41 |
| 37a | >5 | 5 | 5 | 1 | 1.4 | >4.9 |
| 38a | 345 | 236 | 307 | 52 | 12 | 988 |
| 38 | 21 | 21 | 69 | 56 | 62 | 53 |
| 38b | >54 | 0.12 | 1.2 | .10 | 0.03 | 1.7 |
| 39a | 174 | 637 | 707 | 41 | 82 | 41 |
| 57 | 2 | 8.9 | 1.9 | 0.6 | 0.9 | 4.1 |
| 58 | 349 | 5 | 195 | 106 | 163 | 289 |
| 59 | 26 | 26 | 26 | 24 | 15 | 111 |
| 60 | >54 | 0.4 | 4 | 19 | 9 | 26 |
| 61 | 109 | 58 | 363 | >400 | >294 | 297 |
| 62 | 101 | 73 | >200 | 260 | >200 | 185 |

$^a$Each IC$_{50}$ value was determined from a full dose range concentration of inhibitors as described in the Experimental section.
$^b$Data taken from Table 3.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating nicotine addiction in a subject comprising: administering to a subject suffering from nicotine addiction an effective amount of a compound of Formula II, or a pharmaceutically acceptable salt:

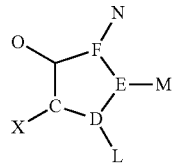

(II)

wherein

C, D, E and F constitute a 5-membered ring containing carbon and nitrogen, wherein the 5-membered ring system is imidazolyl;

X is selected from the group consisting of substituted or unsubstituted phenyl, (CH$_2$)phenyl, (CH$_2$)$_2$phenyl, substituted or unsubstituted cyclohexyl, substituted or unsubstituted (CH$_2$)cyclohexyl, and substituted or unsubstituted (CH$_2$)$_2$cyclohexyl; and L, M, N, and O are hydrogen.

2. The method of claim 1, wherein X is selected from (CH$_2$)phenyl, (CH$_2$)$_2$phenyl, substituted cycloalkyl, substituted or unsubstituted (CH$_2$)cyclohexyl, and substituted or unsubstituted (CH$_2$)$_2$cyclohexyl.

3. The method of claim 1, wherein the compound of Formula II is:

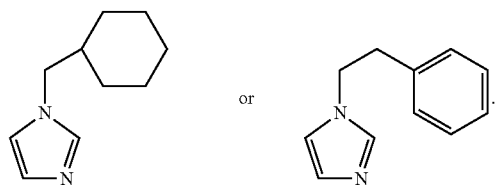 [SMILES: c1cn(CC2CCCCC2)cn1 ; c1ccc(CCn2ccnc2)cc1]

* * * * *